US008303966B2

(12) United States Patent
Lin et al.

(10) Patent No.: US 8,303,966 B2
(45) Date of Patent: *Nov. 6, 2012

(54) IMMUNOGENIC SUBSTANCES COMPRISING A POLYINOSINIC ACID—POLYCYTIDILIC ACID BASED ADJUVANT

(75) Inventors: Haixiang Lin, Beijing (CN); Lie Tao Victor Li, Singapore (SG)

(73) Assignee: Yisheng Biopharma (Singapore) Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 13/032,543

(22) Filed: Feb. 22, 2011

(65) Prior Publication Data

US 2011/0212123 A1    Sep. 1, 2011

Related U.S. Application Data

(63) Continuation of application No. 12/160,583, filed as application No. PCT/SG2006/000176 on Jun. 27, 2006, now abandoned, which is a continuation-in-part of application No. 11/331,575, filed on Jan. 13, 2006, now abandoned.

(51) Int. Cl.
*A61K 47/00* (2006.01)
*C07H 21/00* (2006.01)

(52) U.S. Cl. ................................... 424/278.1; 536/23.1

(58) Field of Classification Search .................. None
See application file for complete search history.

(56) References Cited

U.S. PATENT DOCUMENTS

| | | | |
|---|---|---|---|
| 3,666,646 A | 5/1972 | Lampson et al. |
| 3,692,899 A | 9/1972 | Levy |
| 3,906,092 A | 9/1975 | Hilleman et al. |
| 3,952,097 A | 4/1976 | Levy |
| 4,024,241 A | 5/1977 | Levy |
| 4,082,735 A | 4/1978 | Jones et al. |
| 4,082,736 A | 4/1978 | Jones et al. |
| 4,094,971 A | 6/1978 | Chedid et al. |
| 4,101,536 A | 7/1978 | Yamamura et al. |
| 4,124,702 A | 11/1978 | Lampson et al. |
| 4,140,761 A | 2/1979 | Gerin et al. |
| 4,153,684 A | 5/1979 | Audibert et al. |
| 4,185,089 A | 1/1980 | Derrien et al. |
| 4,186,194 A | 1/1980 | Adam et al. |
| 4,235,771 A | 11/1980 | Adam et al. |
| 4,314,998 A | 2/1982 | Yamamura et al. |
| 4,323,559 A | 4/1982 | Audibert et al. |
| 4,327,085 A | 4/1982 | Audibert et al. |
| 4,349,538 A | 9/1982 | Levy |
| 4,369,178 A | 1/1983 | Yamamura et al. |
| 4,389,395 A | 6/1983 | Lerner et al. |
| 4,857,315 A | 8/1989 | Dennis |
| 4,954,298 A | 9/1990 | Yamamoto et al. |
| 6,096,291 A | 8/2000 | Betbeder et al. |
| 6,468,558 B2 | 10/2002 | Wong |
| 6,514,948 B1 | 2/2003 | Raz et al. |
| 7,838,017 B2 | 11/2010 | Haixiang |
| 2007/0160632 A1 | 7/2007 | Haixiang |
| 2007/0166230 A1 | 7/2007 | Brice et al. |
| 2007/0166239 A1 | 7/2007 | Lin et al. |
| 2007/0166800 A1 | 7/2007 | Lin et al. |
| 2009/0175902 A1 | 7/2009 | Lin et al. |
| 2009/0311334 A1 | 12/2009 | Lin et al. |

FOREIGN PATENT DOCUMENTS

| | | |
|---|---|---|
| CN | 1095951 | 12/1994 |
| CN | 93105862.7 | 9/2000 |
| EP | 0025766 | 3/1981 |
| FR | 2476488 | 8/1991 |
| FR | 2476488 A2 | 8/1991 |
| JP | 57002220 | 1/1982 |
| JP | 01093540 | 4/1989 |
| JP | 01093540 A2 | 4/1989 |
| JP | 1186818 | 7/1989 |
| WO | 2005/014038 | 2/2005 |

OTHER PUBLICATIONS

E De Clercq et al. J. Gene Virol. 1978, vol. 40, pp. 203-212.*
Ichinohe; et al., "Synthetic Double-Stranded RNA Poly(I:C) Combined with Mucosal Vaccine Protects against Influenza Virus Infection", Journal of Virology (2005), 79(5):2910-2919.
Akira; et al., "Pathogen Recognition and Innate Immunity", Cell (2006), 124:783-801.
Champney, et al.,"Modified polyriboinosinic-polyribocytidylic acid complex: sustained interferonemia and its physiological associates in humans", Infect Immun. (1979), 25(3): 831-837.
De Clercq, "Degradation of Poly(inosinic acid) . poly(cytidylic acid) [((I)n. (Cn)] by Human Plasma", European Journal of Biochemistry (2008), 93(1):165-172.
Ellouz, et al., "Minimal structure requirements for adjuvant activity of bacterial peptidoglycan derivatives", Biochem. Biophys. Res. Comm. (1974), 59(4):1317-25.
Gatmaitan, et al., "Modified Polyriboinosiniic-Polyribocytidylic Acid Complex: Induction of Serum Interferon, Fever, and Hypotension in. Rabbits", Antimicrobial agents and chemotherapy (1980), 17(1):49-54.

(Continued)

*Primary Examiner* — Bao Li
(74) *Attorney, Agent, or Firm* — Bozicevic, Field & Francis LLP; Carol L. Francis; Elizabeth A. Alcamo

(57) ABSTRACT

The present invention provides a polynucleotide adjuvant (PICKCa) composition and methods of use in eliciting an immune response, in particular a mucosal immune response. The polynucleotide adjuvant comprises of a polyriboinosinic-polyribocytidylic acid (PIC), at least one antibiotic and at least one positive ion. The present invention also provides an immunogenic composition comprising the polynucleotide adjuvant composition together with other immunogenic compositions such as an antigen (e.g., as in a vaccine) selected from viral, bacterial, fungal, parasitic and/or cancer antigens. The present invention further contemplates methods of use of such adjuvant compositions, particularly in eliciting an immune response, in particular a mucosal immune response to an antigenic compound.

19 Claims, 19 Drawing Sheets

OTHER PUBLICATIONS

Gupta et al., "Adjuvants—a balance between toxicity and adjuvancity", Vaccine (1993), 11:293-306.
Gupta, et al., "Adjuvants for human vaccines—current status, problems and future prospects", Vaccine (1995), 13 (14):1263-78.
Houston et al., "Modified polyriboinosinic-polyribocytidylic acid, an immunological adjuvant. Infection and Immunity", American Society for Microbiology (1976), 14:318-9.
Hu, "Basic research on poly I:C.", Chinese Medical and Pharmaceutical Industry Journal (1983), 12(6):31-4.
Hu, "Tianjin poly I:C laboratory research and clinical application", Fujian Medical Journal (1983), 12(6):31-4.
Iwasaki; et al., "Toll-like receptor control of the adaptive immune responses", Nature Immunology (2004), 5 (10):987-995.
Kanzler et al., "Therapeutic targeting of innate immunity with toll-like receptor agonists and antagonists", Nature Medicine (2007), 13(5):552-9.
Kende et al., "Enhanced therapeutic efficacy of poly(ICLC) and ribavirin combinations against rift valley fever virus infection in mice", Antimicrobial agents and chemotherapy, American Society for Microbiology (1987), 31(7):986-90.
Kenney, "Meeting report: 2nd meeting on novel adjuvants currently in/close to human clinical testing", Vaccine (2002), 20:2155-63.
Lake et al., "Involvement of protein kinase C in macrophages activation by poly (C)", American Journal of Physiology (1994), 226:C134-42.
Levy, et al., "Immune modulating effects of poly ICLC", Annals New York Academy of Sciences (1980), 33-41.
Levy, et al., "Interferon induction in primates by stabilized polyriboinosinic acid-polyribocytidylic acid: effect of component size", Infect Immun. (1981), 34(2):416-421.
Lin, "Experimental Study on Rabies Vaccine Plus Pika Adjuvant", Chinese Journal of Biologicals (1998), 11:137-40.
Lin, et al., "A new immunostimulatory complex (PICKCa) in experimental rabies: antiviral and adjuvant effects", Archives of Virology (1993), 131:307-19.
Machida, et al., "Relationship between the molecular size of poly I-poly C and its biological activity", Japan J. Microbiol. (1976), 20(2):71-76.
Morahan, et al., "Antiviral activity and side effects of polyriboisinic-cytidylic acid complexes as affected by molecular size", PNAS (1972), 69(4):842-6.
Norlund, et al., "Inhibition of biologic activity of Poly I: Poly C by human plasma (34492)", Proc. Soc. Exp. Biol. Med. (1970), 133:439-44.
Phillips, et al., "Systemic toxicity of polyinosinic acid: polycytidylic acid in rodents and dogs", Toxicology and Applied Pharmacology (1971), 18:220-30.
Pulendran; et al., "Translating Innate Immunity into Immunological Memory: Implications for Vaccine Development", Cell (2006), 124:849-863.
Sela, "Antigenicity: some molecular aspects", Science (1969), 166:1365-74.
Shu; et al., "Biological functions and application of Poly I:C", Shanxi Journal of Medicine (1989), 18(10):40-42.
Smorodintsev, et al., "Comparative study of the toxicity of poly G-poly C and poly I-poly C in different objects", Vopr Virusol. (1978), (2):201-206.
Stern, "A nuclease from animal serum which hydrolyzes double-stranded RNA", Biochem. Biophys. Res. Comm. (1970), 41(3):608-14.
Stringfellow, et al., "Interferon induction by and toxicity of polyriboinosinic acid [poly(rl)].polyribocytidylic acid [poly (rC)], mismatched analog poly (rl).poly[r(C12Uracil)n], and poly(rl).poly(rC) L-lysine complexed with carboxymethylcellulose", Antimicrob Agents Chernother. (1980), 17(6):988-992.
Ts'o, et al., "An Integrated and Comparative Study of the Antiviral Effects and Other Biological Properties of the Polyinosinic Acid-Polycytidylic Acid and Its Mismatched Analogues", Molecular Pharmacology, 12:299-312, Copyright 1976 by the American Society for Pharmacology and Experimental Therapeutics.
Wright, et al., "The adjuvant effects of mycoviral dsRNA and polyinosinic:polycytidylic acid on the murine immune response", Biochem. Biophys. Res. Comm. (1985), 131(2):949-55.
Zong; et al., "Study on Determining the Molecular Weight of PICKCa and PI. PC with the Method of Polyacrylamide Gel Electrophoresis", Chinese Journal of Pharmaceutical Analysis (1993), 13(4):219-22.
Levy; et al., "A Modified Polyriboinosinic-Polyribocytidylic Acid Complex That Induces Interferon in Primates", The Journal of Infectious Diseases (1975), 132(4):434-439.
US 6,008,200, 12/1999, Krieg (withdrawn)

* cited by examiner

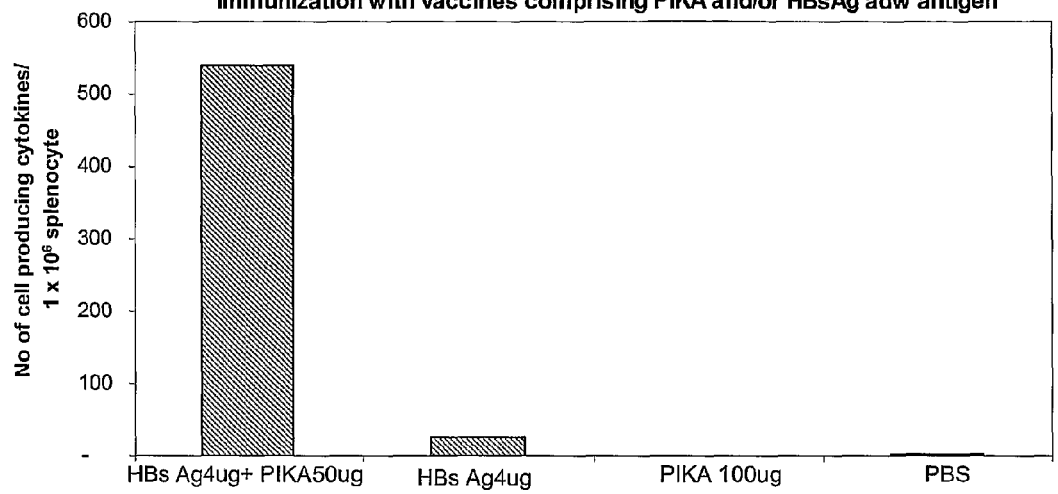
Fig.1: ELISPOT detection of murine splenocytes producing IFN-gamma after immunization with vaccines comprising PIKA and/or HBsAg adw antigen
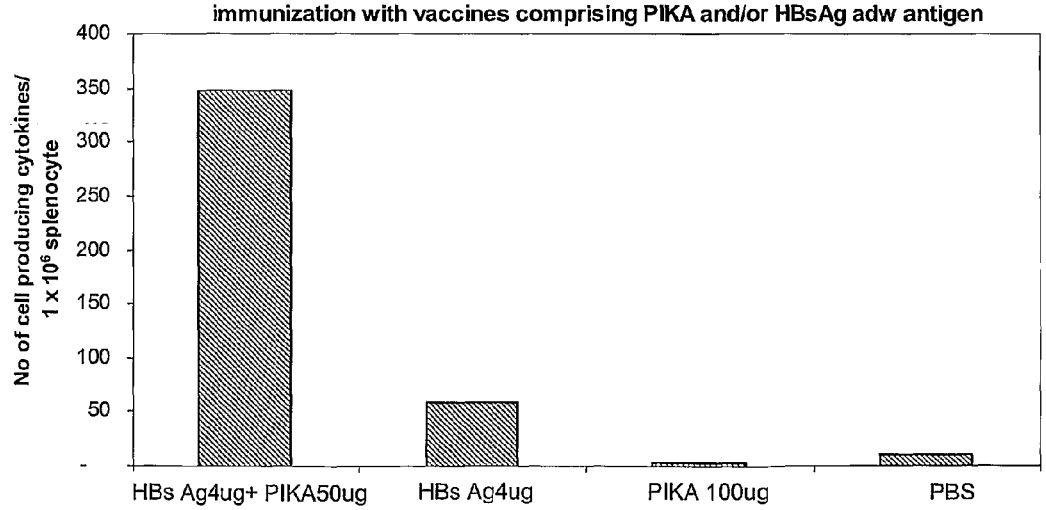
Fig. 2: ELISPOT detection of murine splenocytes producing IL-2 after immunization with vaccines comprising PIKA and/or HBsAg adw antigen

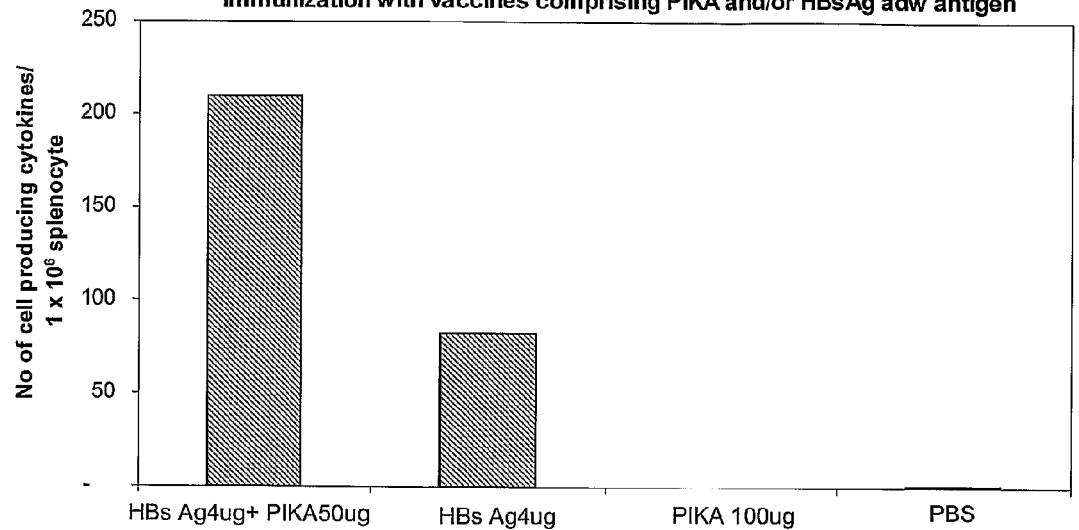
Fig. 3: ELISPOT detection of murine splenocytes producing IL-4 after immunization with vaccines comprising PIKA and/or HBsAg adw antigen
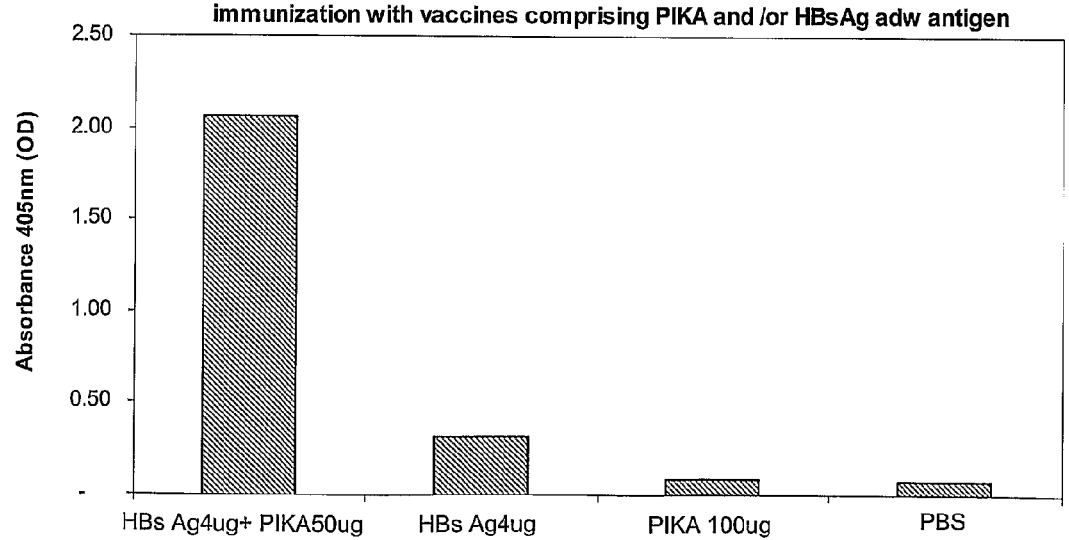
Fig. 4: ELISA detection of specific IgG titers from murine serum (diluted 400x) after immunization with vaccines comprising PIKA and/or HBsAg adw antigen

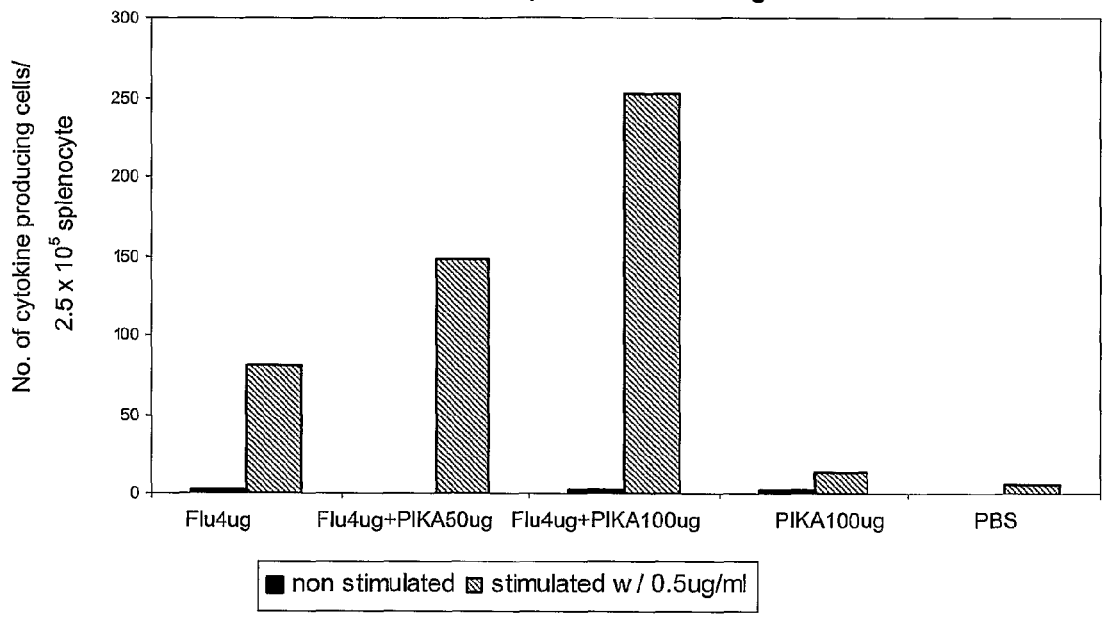
Fig. 5: ELISPOT detection of murine splenocytes producing IFN-gamma after immunization with vaccines comprising PIKA and/or incativated split influenza antigens
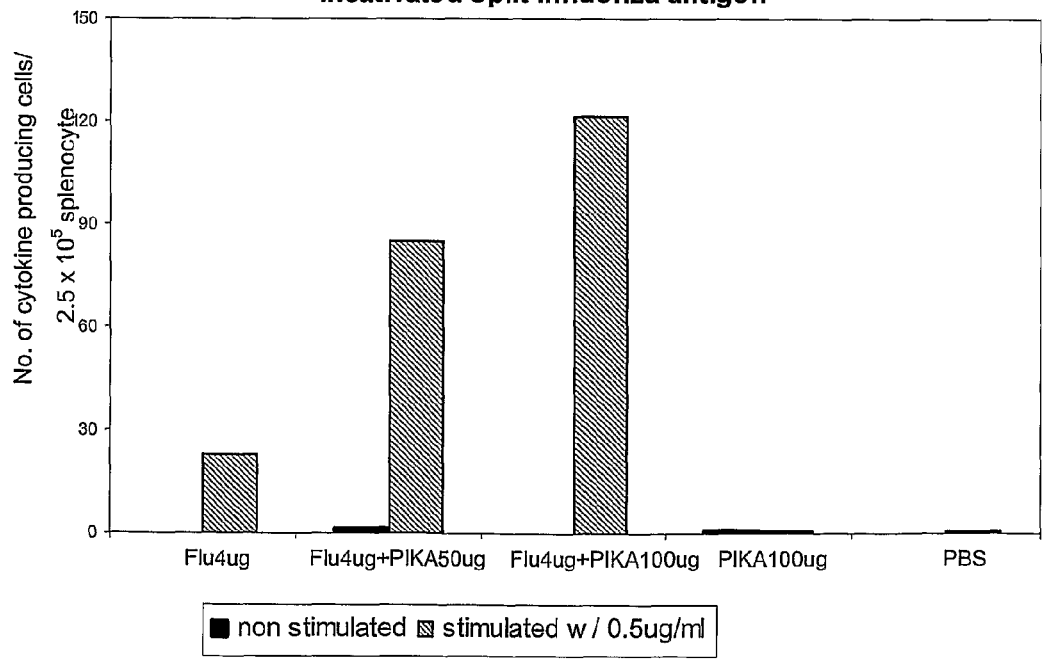
Fig. 6: ELISPOT detection of murine splenocytes producing IL-2 after immunization with vaccines comprising PIKA and/or incativated split influenza antigen

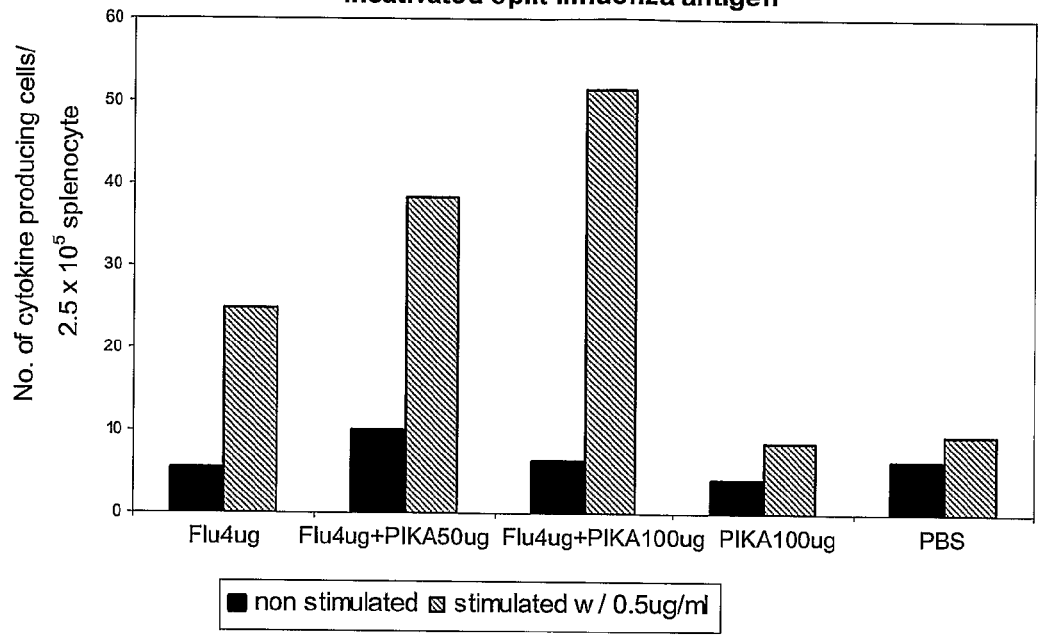
Fig. 7: ELISPOT detection of murine splenocytes producing IL-4 after immunization with vaccines comprising PIKA and/or incativated split influenza antigen
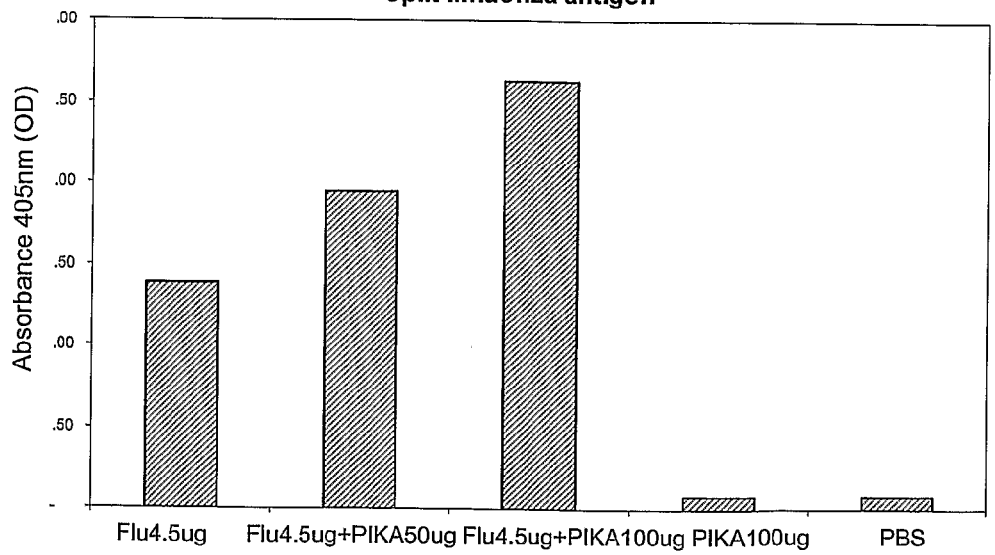
Fig. 8: ELISA detection of specific IgG in murine serum (diluted 900x) after immunization with vaccines comprising PIKA and/or inactivated split influenza antigen

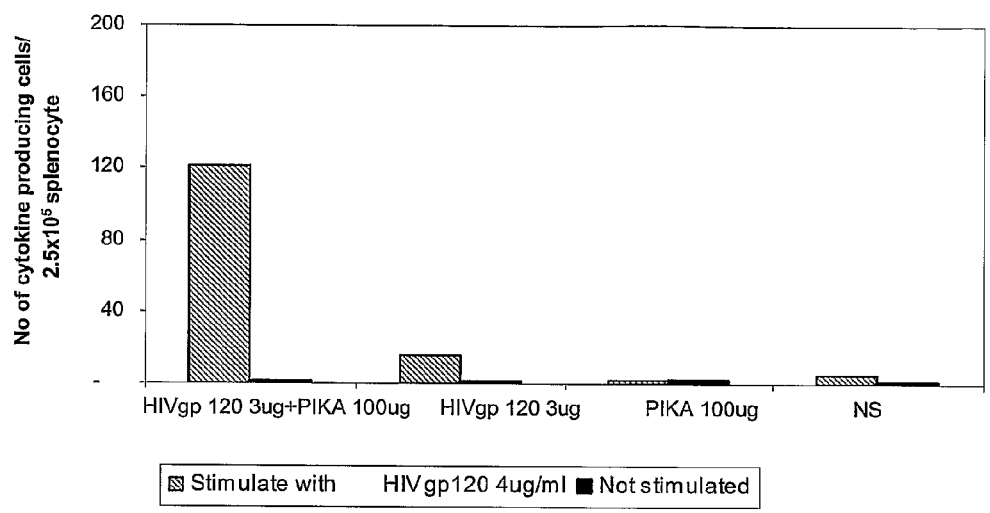
Fig 9: ELISPOT detection of murine splenocytes producing IFN-gamma after immunization with vaccines comprising PIKA and/or HIV gp120 antigen
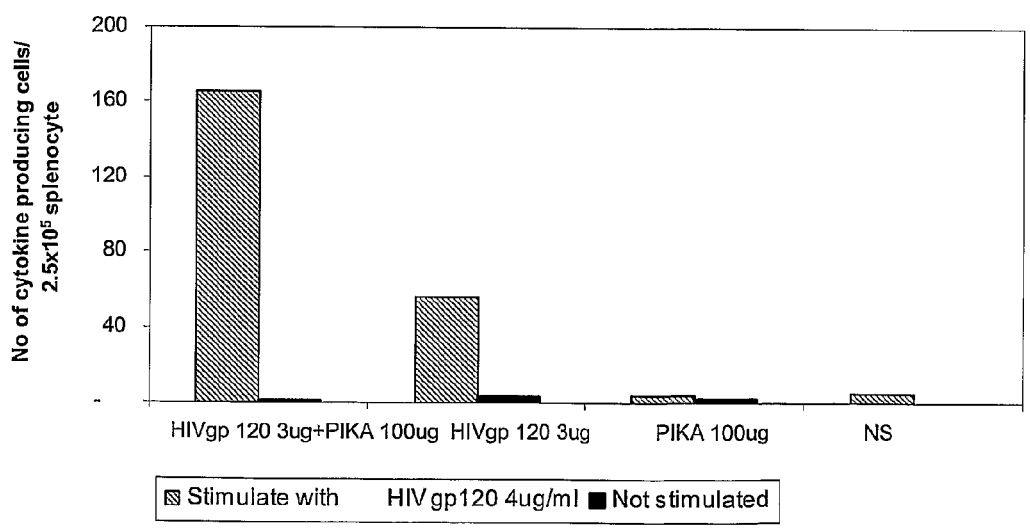
Fig. 10: ELISPOT detection of murine splenocytes producing Il-2 after immunization with vaccines comprising PIKA and/or HIV gp120 antigen

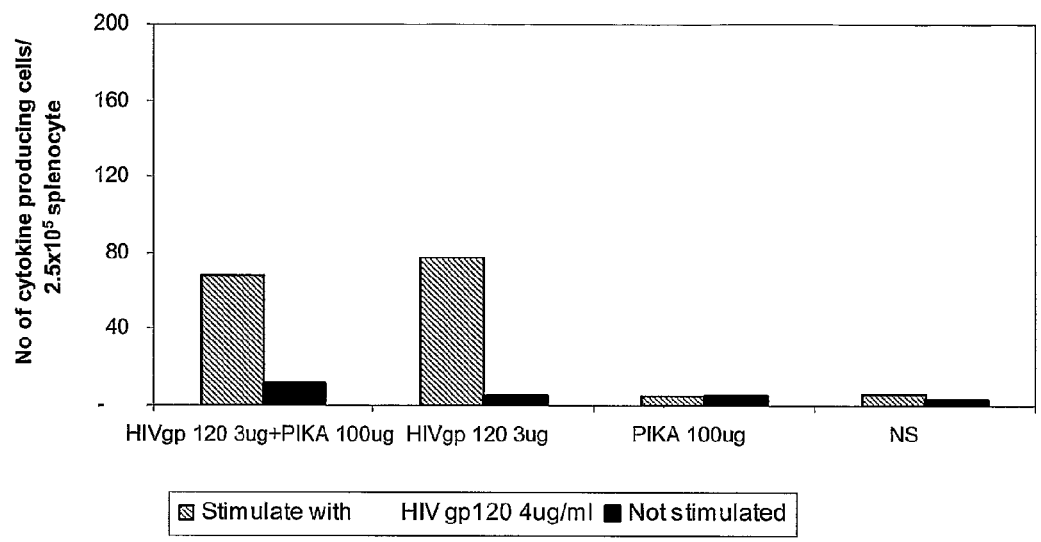
Fig. 11: ELISPOT detection of murine splenocytes producing Il-4 after immunization with vaccines comprising PIKA and/or HIV gp120 antigen
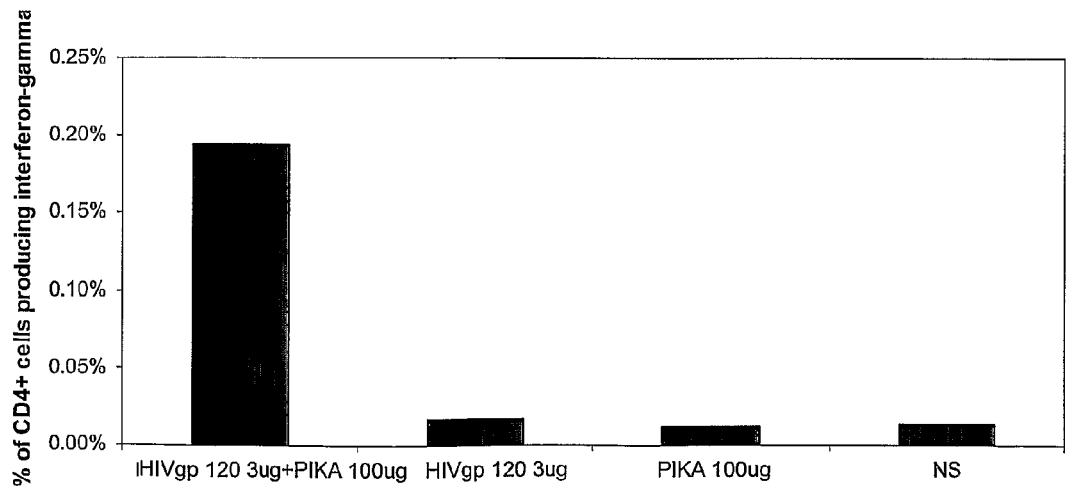
Fig. 12: FACS analysis of CD4+ murine splenocytes producing interferon-gamma after immunization with vaccines comprising PIKA and/or HIV gp120 antigen

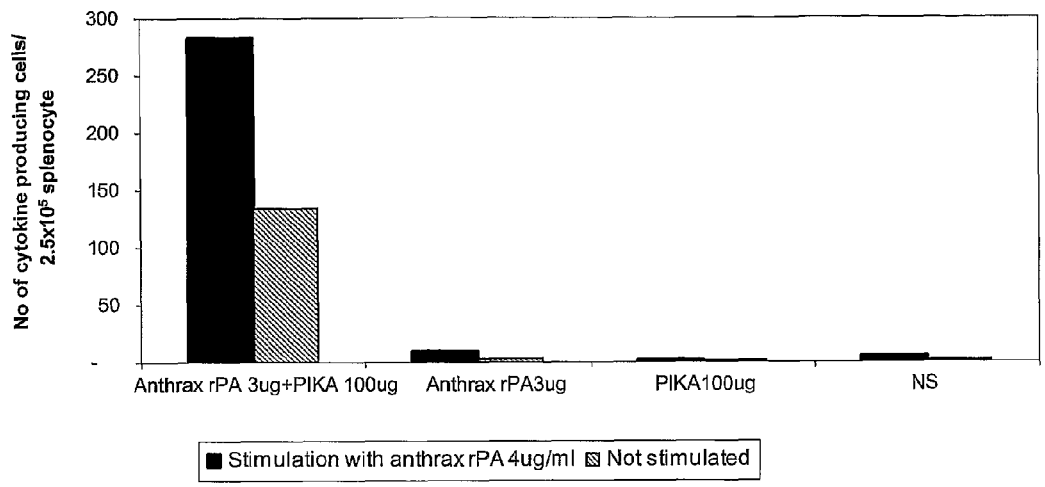
Fig. 13: ELISPOT detection of murine splenocytes producing IFN-gamma after immunization with vaccines comprising PIKA and/or anthrax rPA antigen
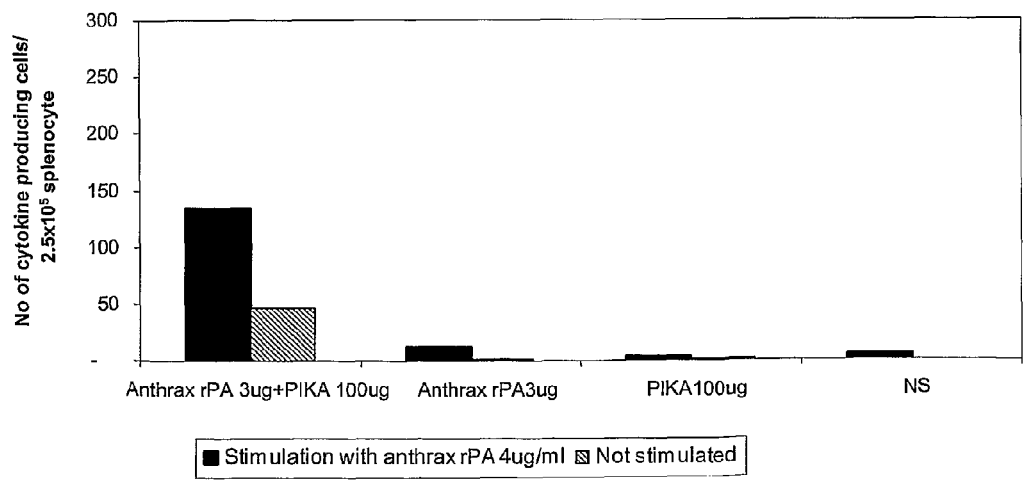
Fig. 14: ELISPOT detection of murine splenocytes producing IL-2 after immunization with vaccines comprising PIKA and/or anthrax rPA antigen Fig. 15: ELISPOT detection of murine splenocytes producing IL-4 after immunization with vaccines comprising PIKA and/or anthrax rPA antigen Fig. 16: FACS analysis of CD4+ murine splenocytes producing interferon-gamma after immunization with vaccines comprising anthrax and/or anthrax rPA antigen Fig. 17. ELISA detection of specific IgG titers from murine serum (diluted 400x) 4 weeks after immunization vaccines comprising PIKA and/or anthrax rPA antigen Fig. 18. ELISA detection of specific IgG titers from murine serum (diluted 300x) 16 weeks after immunization vaccines comprising PIKA and/or anthrax rPA antigen

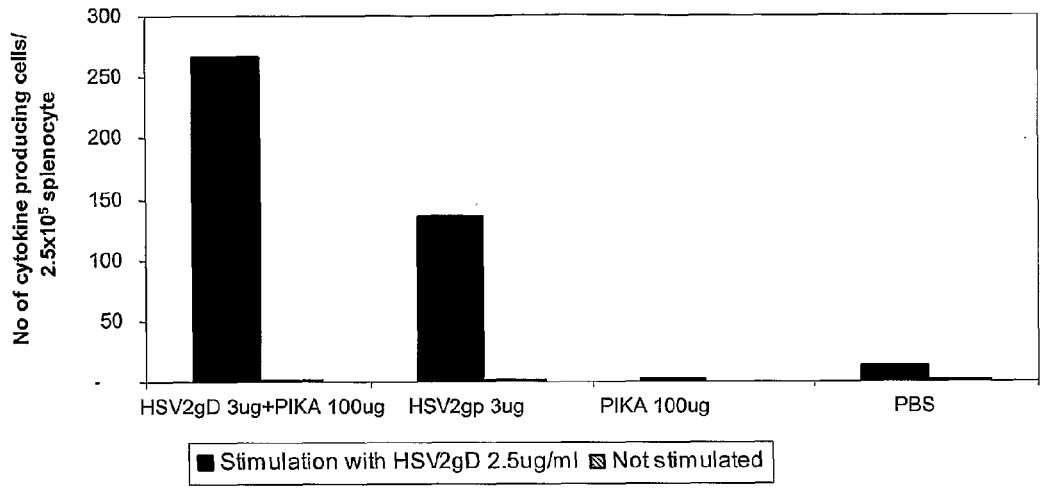
Fig. 19: ELISPOT detection of murine splenocytes producing IFN-gamma after immunization with vaccines comprising PIKA and/or HSV2 gD antigen
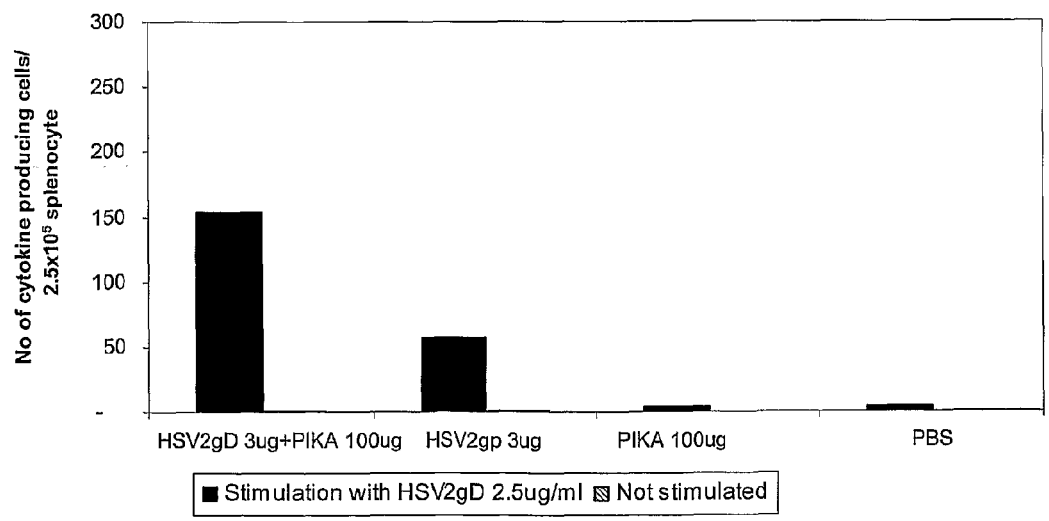
Fig. 20: ELISPOT detection of murine splenocytes producing IL-2 after Immunization with vaccines comprising PIKA and/or HSV2gD antigen

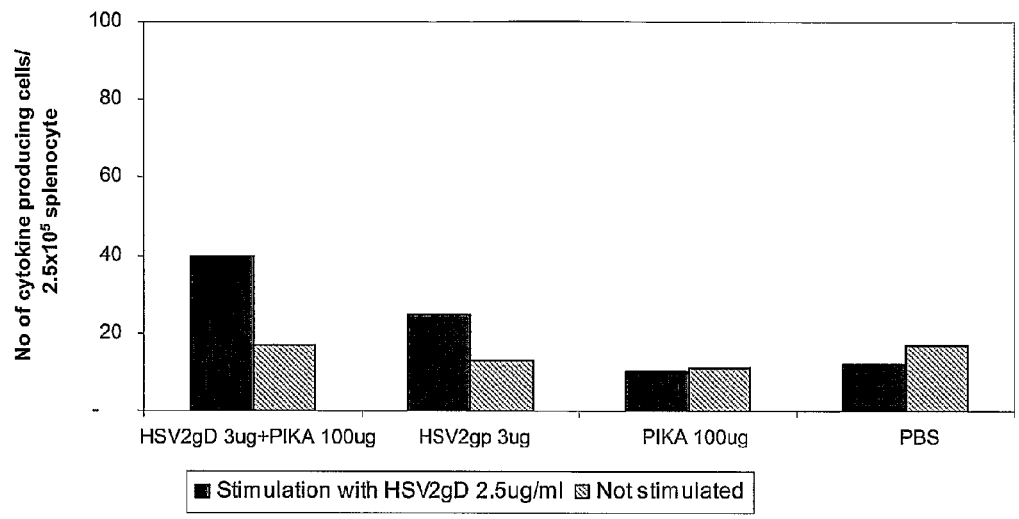
Fig. 21: ELISPOT detection of murine splenocytes producing IL-4 after immunization with vaccines comprising PIKA and/or HSV2gp antigen
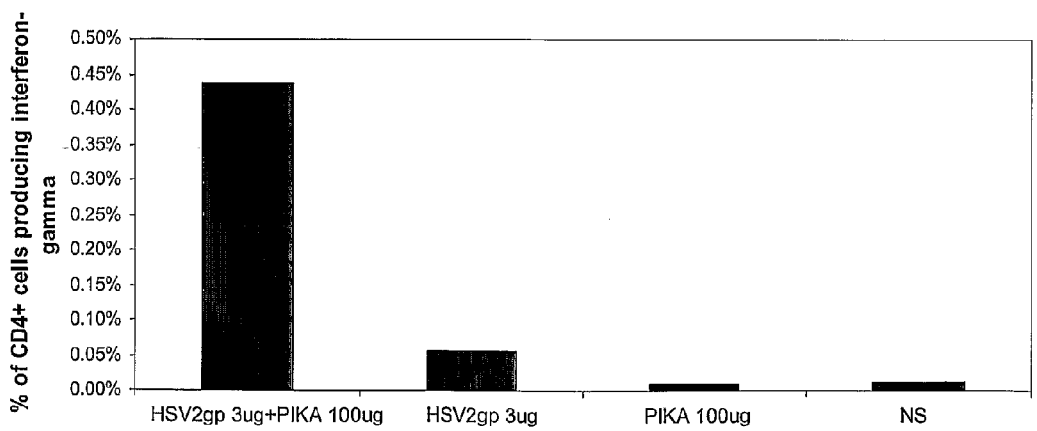
Fig. 22: FACS analysis of CD4+ murine splenocytes producing interferon-gamma after immunization with vaccines comprising anthrax and/or HSV 2gD antigen

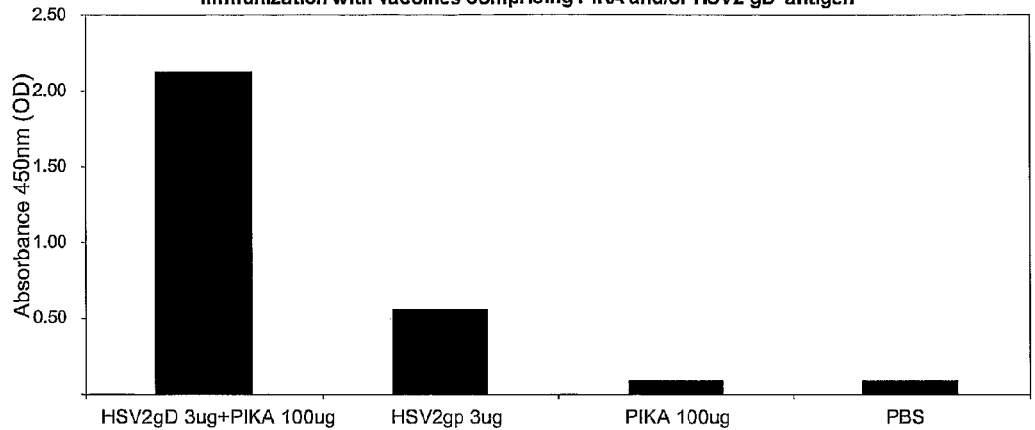
Fig. 23: ELISA detection of specific IgG titers in murine serum (2,700x dilution) after immunization with vaccines comprising PIKA and/or HSV2 gD antigen
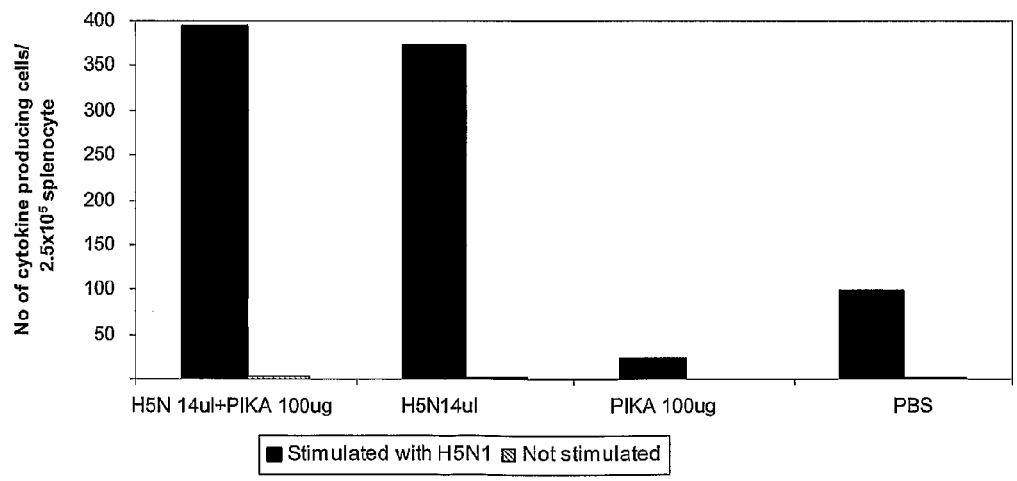
Fig. 24: ELISPOT detection of murine splenocytes producing IFN-gamma after immunization with vaccines comprising PIKA and/or inactivated H5N1 antigen Fig. 25: ELISPOT detection of murine splenocytes producing IL-2 after immunization with vaccines comprising PIKA and/or inactivated H5N1 antigen ■ Stimulated with H5N1  ▨ Not stimulated Fig. 26: ELISPOT detection of murine splenocytes producing IL-4 after immunization with vaccines comprising PIKA and/or inactivated H5N1 antigen ■ Stimulated with H5N1  ▨ Not stimulated Fig. 27: FACS analysis of CD4+ murine splenocytes producing interferon-gamma after immunization with vaccines comprising anthrax and/or inactivated H5N1 antigen Fig. 28: ELISA detection of specific IgG titers from murine serum (900x dilution) after immunization with vaccines comprising PIKA and/or inactivated H5N1 antigen Fig. 29: ELISA detection of specific IgG titers from murine serum (16,000x dilution) after immunization with vaccines comprising PIKA and/or inactivated SARS antigen Fig. 30: ELISA detection of specific H5 antibody titers from chicken serum after immunization with vaccines comprising PIKA and/or inactivated H5N1 antigen

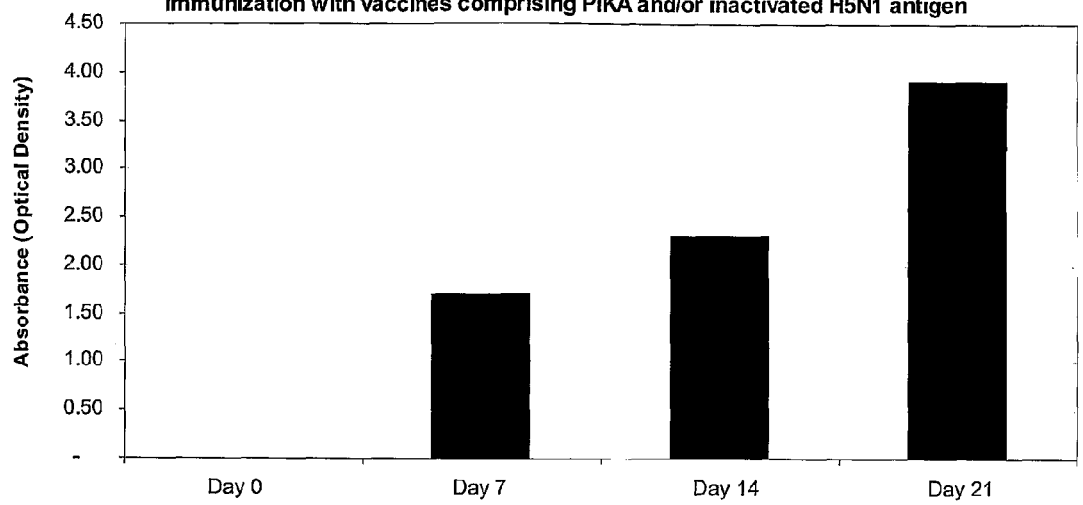
Fig. 31: ELISA detection of specific H9 titers from chicken serum after immunization with vaccines comprising PIKA and/or inactivated H

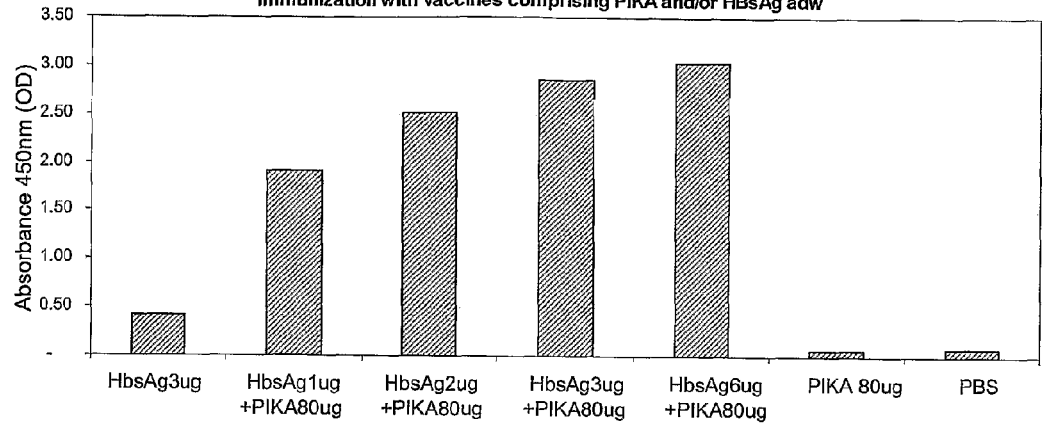
Fig. 33: ELISA detection of specific IgG titers from murine serum (12,800x dilution) after immunization with vaccines comprising PIKA and/or HBsAg adw
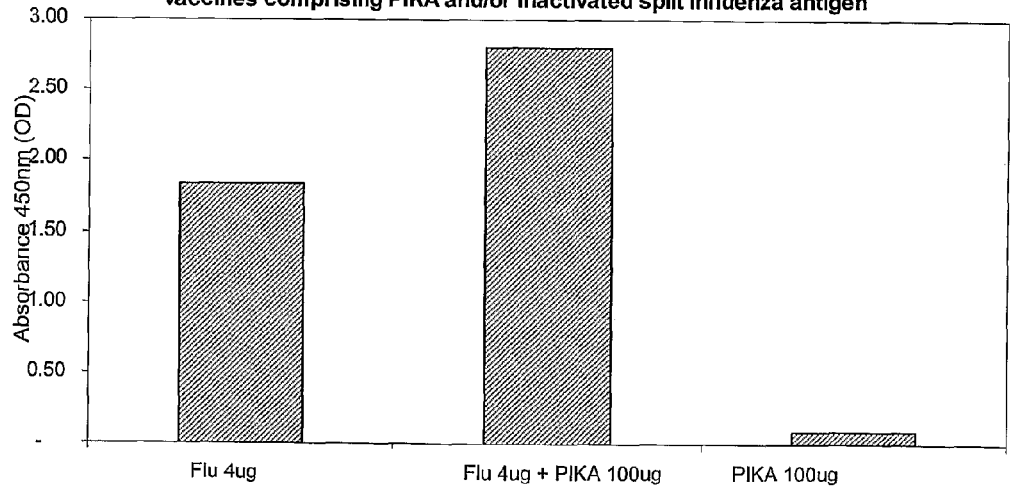
Fig. 34: ELISA detection of specific IgG titers from murine serum after immunization vaccines comprising PIKA and/or inactivated split influenza antigen

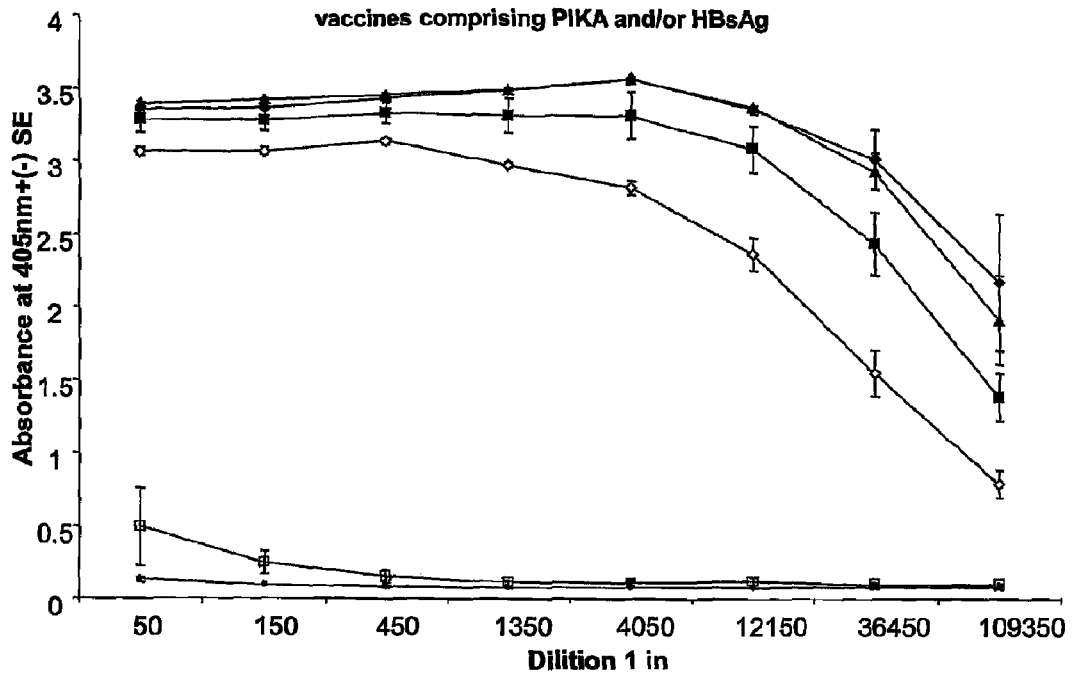
Fig. 35: ELISA detection of specific IgG1 titers from murine serum after immunization with vaccines comprising PIKA and/or HBsAg
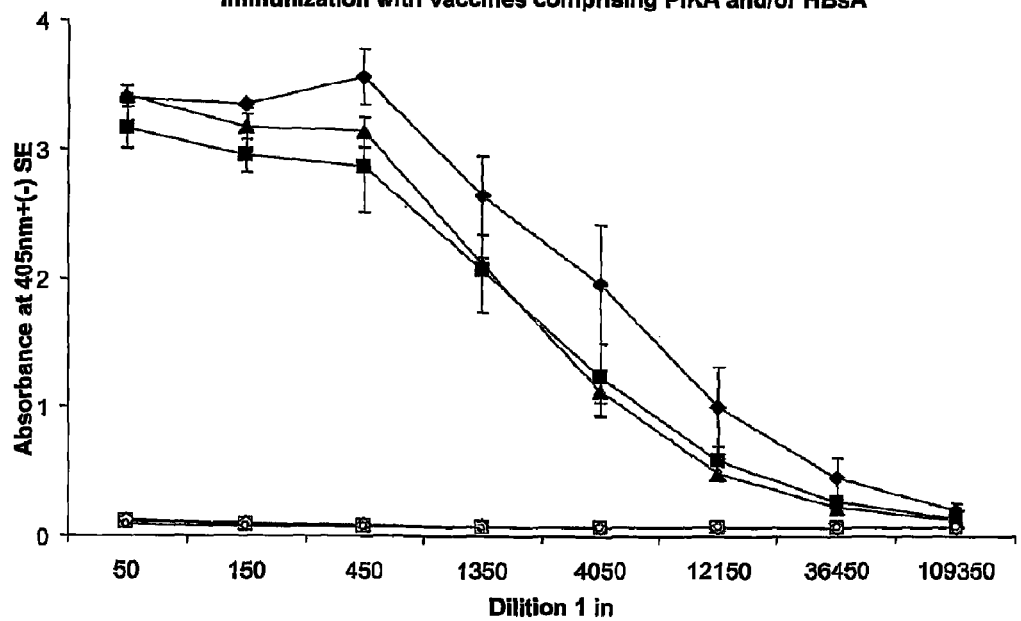
Fig.36: ELISA detection of specific IgG2a titers in murine serum after immunization with vaccines comprising PIKA and/or HBsA
—◇— HBsAg 3ug —■— PIKA 50ug+HBsAg 3ug —▲— PIKA 100ug+HBsAg 3ug
—◆— PIKA 200ug+HBsAg 3ug —□— PIKA 100ug —•— PBS 100ul Fig. 37 ELISPOT detection of murine splenocytes producing INF-gamma after immunization with vaccine comprising PIKA and/or HBsAg
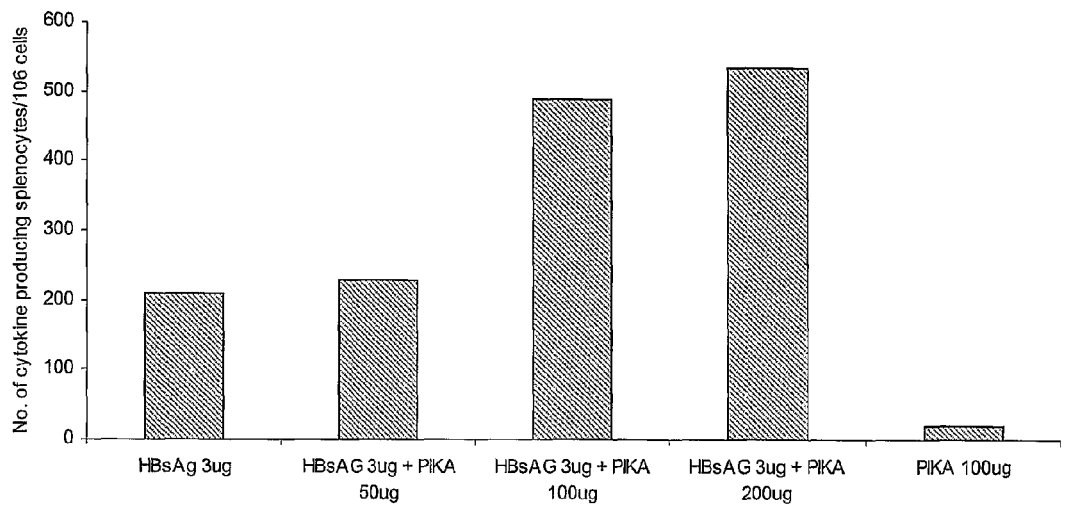
Fig. 38 ELISPOT detection of murine splenocytes (post restimulation for 6 days with 2ug/ml IPQ peptide) producing INF-gamma after immunization with vaccine comprising PIKA and/or HBsAg after
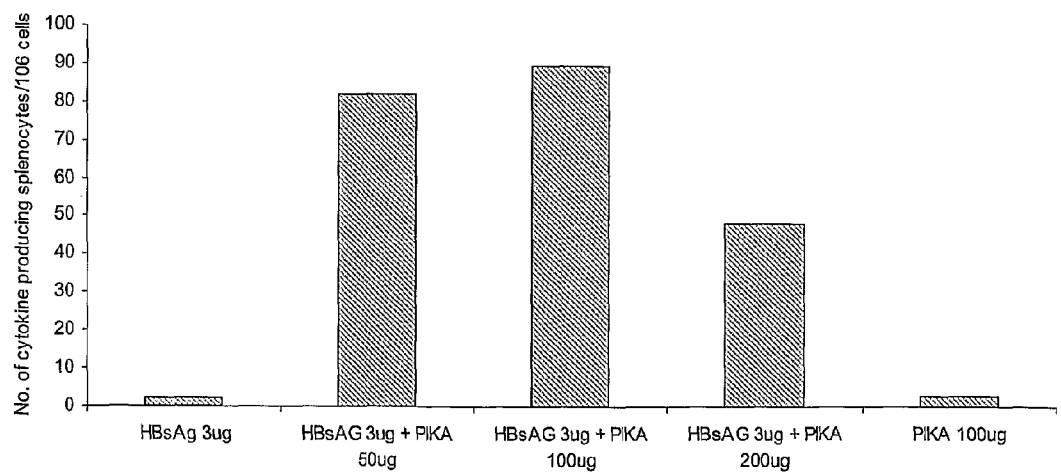

IMMUNOGENIC SUBSTANCES COMPRISING A POLYINOSINIC ACID—POLYCYTIDILIC ACID BASED ADJUVANT

CROSS REFERENCE TO RELATED APPLICATIONS

This application is a Continuation of U.S. application Ser. No. 12/160,583 filed Nov. 18, 2008, which application claims priority to PCT application serial no. SG2006/000176, filed Jun. 27, 2006, which application is a Continuation-In-Part of U.S. application Ser. No. 11/331,575, filed Jan. 13, 2006, the disclosures of which applications are incorporated in their entirety herein.

FIELD OF INVENTION

The invention generally relates to immunogenic compositions and methods of their use. More specifically the invention relates to an immunogenic composition comprising a polynucleotide adjuvant in combination with one or more antigenic substances to be used to elicit disease specific immune response in a host.

BACKGROUND OF INVENTION

The immune system may exhibit both specific and nonspecific immunity. Nonspecific immunity encompasses various cells and mechanisms such as phagocytosis (the engulfing of foreign particles or antigens) by macrophages or granulocytes, and natural killer (NK) cell activity, among others. Nonspecific immunity relies on mechanisms less evolutionarily advanced and does not display the acquired nature of specificity and memory, which are exemplary hallmarks of a specific immune response. The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

Generally, B and T lymphocytes, which display specific receptors on their cell surface for a given antigen, produce specific immunity. The specific immune system may respond to different antigens in two ways: 1) humoral-mediated immunity, which includes B cell stimulation and production of antibodies or immunoglobulins, antigen and helper T cells (predominantly Th2), and 2) cell-mediated immunity, which generally involves T cells including cytotoxic T lymphocytes (CTLs), although other cells are also involved in the generation of a CTL response (e.g., antigen presenting cells and Th1 cells).

In the continual pursuit for safer and more effective vaccines, new technologies, including recombinant, purification and synthetic methods, have been used to improve the quality and specificity of antigens used. Purified, sub-unit and synthesized antigens demonstrate increased safety but diminished immunogenicity which has been one driver for the identification of effective adjuvant. Thus an effective adjuvant is increasingly an essential component of modern vaccines. Adjuvants are generally compounds, that when administered with an antigen (either in conjunction with, or given prior to the administration of the antigen) enhances and/or modifies the immune response to that particular antigen.

Exemplary adjuvants that have been used to enhance an immune response include aluminum compounds (all generally referred to as "Alum"), oil-in-water emulsions (complete Freund's adjuvant (CFA) is an oil-in-water emulsion containing dried, heat-killed *Mycobacterium tuberculosis* organisms), Saponin (isolated from the bark of Quillaja Saponoria, the adjuvant active component known as Quile A), CpG ODN (synthetic oligodeoxynucleotide containing unmethylated CpG dinucleotides), monophosphoryl lipid A (MPL) derived from the lipopolysaccharide of *Salmonella minnesota* Re595, Liposomes (usually made up of biodegradable materials such as phospholipids) and biodegradable polymer microspheres (made from a variety of polymers such as, polyphosphazene and polyanhydrides). The adjuvant properties of these compounds have been evaluated with each adjuvant showing advantages and disadvantages.

Polynucleotide complexes have been investigated for their various applications including acting as adjuvants. Double-stranded RNAs (dsRNAs) are very potent biologic modifiers that can exert a profound influence on cells at nanomolar concentrations. The modulating effects of dsRNA include a broad spectrum of actions at the molecular and cellular levels.

At the molecular level, dsRNAs can elicit biological effects such as interferon synthesis, induction of protein kinase, enhancement of histocompatibility antigen and inhibition of metabolism. And at the cellular level, dsRNA can elicit biological effects such as pyrogenicity, mitogenicity, macrophage activation, activation of humoral immunity, activation of cell-mediated immunity and induction of antiviral state. Immunomodulating effects of dsRNAs has been disclosed. U.S. Pat. No. 4,124,702 disclosed that double stranded polynucleotides induced interferon induction in living animal cells. U.S. Pat. No. 3,906,092 disclosed that the antibody response to an adjuvant type vaccine was augmented by incorporation in the vaccine of a polynucleotide or a complex of polynucleotides. Houston et al. established PICLC (polyinosinic acid polycytidylic acid poly-L-lysinecarboxy-methylcellulose complex) as a potent adjuvant by increasing primary antibody response without the aid of an additional adjuvant.

Polyinosinic acid-polycytidylic acid (PIC), one of most studied polynucleotide complexes, was not effective when used in monkeys and humans due to its instability in the body after administration. Thus, PIC has been modified in many ways to overcome one or another deficiency. For example, a complex of polyriboinosinic-polyribocytidylic acid with poly-L-lysine hydrobromide is about 5 to 15 times as resistant to hydrolysis by pancreatic ribonuclease as the parent PIC.

Lin et al. described that an antiviral drug comprising polyinosinic polycytidylic acid, kanamycin and calcium can be used as an adjuvant (Lin, et al., A new immunostimulatory complex (PICKCa) in experimental rabies: antiviral and adjuvant effects, Arch Virol, 131: 307-19, 1993; and Chinese Patent No. 93105862.7). The Chinese Patent No. 93105862.7 provides for the use of the general composition of Poly I:C, kanamycin and calcium (PICKCa) as an adjuvant in a vaccine for human and mammalian application. However, Lin found that that the form of PICKCa originally identified does not provide the optimal efficacy/safety profile for use as an adjuvant and also induces unacceptable adverse side effects under certain conditions.

The present invention provides novel immunogenic compositions that exhibit improved safety and efficacy profiles; and methods of use of such compositions. Subject immunogenic compositions include a polynucleotide adjuvant and an antigen.

LITERATURE

The following references may be of interest:
JP 1093540A2;
U.S. Pat. No. 4,124,702
U.S. Pat. No. 3,692,899
U.S. Pat. No. 3,906,092
U.S. Pat. No. 4,389,395
U.S. Pat. No. 4,349,538
U.S. Pat. No. 4,024,241
U.S. Pat. No. 3,952,097
Houston et al., Infection and Immunity, 14: 318-9, 1976C
Wright and Adler-Moore, Biochemical and Biophysical Research Communications, 131: 949-45, 1985
Lin, et al., A new immunostimulatory complex (PICKCa) in experimental rabies: antiviral and adjuvant effects, Arch Virol, 131: 307-19, 1993
Chinese Patent 93105862.7
Gupta R. K. et al., Adjuvants—a balance between toxicity and adjuvanticity, Vaccine, 11:293-306, 1993
Arnon, R. (Ed.) Synthetic Vaccines 1:83-92, CRC Press, Inc., Boca Raton, Fla., 1987
Sela, M., Science 166:1365-1374 (1969)
U.S. Pat. No. 6,008,200
Ellouz et al., Biochem. & Biophy. Res. Comm., 59:1317, 1974
U.S. Pat. No. 4,094,971
U.S. Pat. No. 4,101,536
U.S. Pat. No. 4,153,684
U.S. Pat. No. 4,235,771
U.S. Pat. No. 4,323,559
U.S. Pat. No. 4,327,085
U.S. Pat. No. 4,185,089
U.S. Pat. No. 4,082,736
U.S. Pat. No. 4,369,178
U.S. Pat. No. 4,314,998
U.S. Pat. No. 4,082,735
U.S. Pat. No. 4,186,194
U.S. Pat. No. 6,468,558
New Trends and Developments in Vaccines, edited by Voller et al., University Park Press, Baltimore, Md., USA, 1978
Klein, J., et al., Immunology (2nd), Blackwell Science Inc., Boston (1997)
Gupa R. K. and Siber G. R., Adjuvants for human vaccines—current status, problems and future prospects, Vaccine, 13 (14): 1263-1276, 1995
Richard T Kenney et al. Meeting Report—$2^{nd}$ meeting on novel adjuvants currently in/close to human clinical testing, Vaccine 20 2155-2163, 2002
Laboratory Techniques in Rabies Edited by F X Meslin, M M Kaplan, H Koprowski $4^{th}$, 1996, Edition ISBN 92 4 1544 1

SUMMARY OF THE INVENTION

In general, the present invention relates to novel immunogenic compositions comprising a polynucleotide adjuvant composition together with an immunogenic or antigenic substance, and methods of use in eliciting an immune response.

Accordingly, there is provided an immunogenic composition comprising: (a) a polynucleotide adjuvant comprising: a polyriboinosinic-polyribocytidylic acid (PIC), at least one an antibiotic, and at least one positive ion; and (b) at least one antigen; wherein the composition is formulated for sustained release administration.

The immunogenic composition according to the invention may comprise a polynucleotide adjuvant composition molecules heterogeneous for molecular weight, wherein the molecular weight is at least 66,000 Daltons.

BRIEF DESCRIPTION OF THE DRAWINGS

FIG. 1—ELISPOT detection of murine splenocytes producing interferon-γ after immunization with vaccines comprising PIKA and/or HBsAg adw FIG. 2—ELISPOT detection of murine splenocytes producing IL-2 after immunization with vaccines comprising PIKA and/or HBsAg adw FIG. 3—ELISPOT detection of IL-4 produced by murine splenocytes after immunization with vaccines comprising PIKA and/or HBsAg adw FIG. 4—ELISA detection of specific IgG titers from murine serum (diluted 400×) after immunization with vaccines comprising PIKA and/or HBsAg adw FIG. 5—ELISPOT detection of murine splenocytes producing interferon-gamma (γ) after immunization with vaccines comprising PIKA and/or inactivated split influenza antigen FIG. 6—ELISPOT detection of murine splenocytes producing IL-2 after immunization with vaccines comprising PIKA and/or inactivated split influenza antigen FIG. 7—ELISPOT detection of murine splenocytes producing IL-4 after immunization with vaccines comprising PIKA and/or inactivated split influenza antigen FIG. 8—ELISA detection of specific IgG titers from murine serum (diluted 900×) after immunization with vaccines comprising PIKA and/or inactivated split influenza antigen FIG. 9—ELISPOT detection of murine splenocytes producing interferon-γ after immunization with vaccines comprising PIKA and/or HIV gp120 antigen FIG. 10—ELISPOT detection of murine splenocytes producing IL-2 after immunization with vaccines comprising PIKA and/or HIV gp120 antigen FIG. 11—ELISPOT detection of murine splenocytes producing IL-4 after immunization with vaccines comprising PIKA and/or HIV gp120 antigen FIG. 12—FACS analysis of murine splenocytes after immunization with vaccines comprising PIKA and/or HIV gp120 antigen, percentage of CD4+ve cells expressing interferon-γ

FIG. 13—ELISPOT detection of murine splenocytes producing interferon-γ after immunization with vaccines comprising PIKA and/or anthrax rPA antigen FIG. 14—ELISPOT detection of murine splenocytes producing IL-2 after immunization with vaccines comprising PIKA and/or anthrax rPA antigen FIG. 15—ELISPOT detection of murine splenocytes producing IL-4 after immunization with vaccines comprising PIKA and/or anthrax rPA antigen FIG. 16—FACS analysis of murine splenocytes after immunization with vaccines comprising PIKA and/or anthrax rPA antigen, percentage of CD4+ve cells expressing interferon-γ

FIG. 17—ELISA detection of specific IgG titers from murine serum (diluted 400×) after immunization with vaccines comprising PIKA and/or anthrax rPA antigen FIG. 18—ELISA detection of specific IgG titers from murine serum 16 weeks after immunization with vaccines comprising PIKA and/or anthrax rPA antigen FIG. 19—ELISPOT detection of murine splenocytes producing interferon-γ after immunization with vaccines comprising PIKA and/or HSV 2gD antigen FIG. 20—ELISPOT detection of murine splenocytes producing IL-2 after immunization with vaccines comprising PIKA and/or HSV 2gD antigen FIG. 21—ELISPOT detection of murine splenocytes producing IL-4 after immunization with vaccines comprising PIKA and/or HSV 2gD antigen FIG. 22—FACS analysis of murine splenocytes after immunization with vaccines comprising PIKA and/or HSV 2gD antigen, percentage of CD4+ve cells expressing interferon-γ

FIG. 23—ELISA detection of specific IgG titers from murine serum (diluted 2,700×) after immunization with vaccines comprising PIKA and/or HSV 2 gD antigen FIG. 24—ELISPOT detection of murine splenocytes producing interferon-γ after immunization with vaccines comprising PIKA and/or inactivated H5N1 antigen FIG. 25—ELISPOT detection of murine splenocytes producing IL-2 after immunization with vaccines comprising PIKA and/or inactivated H5N1 antigen FIG. 26—ELISPOT detection of murine splenocytes producing IL-4 after immunization with vaccines comprising PIKA and/or inactivated H5N1 antigen FIG. 27—FACS analysis of murine splenocytes after immunization with vaccines comprising PIKA and/or inactivated H5N1 antigen, percentage of CD4+ve cells expressing interferon-γ

FIG. 28—ELISA detection of specific IgG titers from murine serum (diluted 900×) after immunization with vaccines comprising PIKA and/or inactivated H5N1 antigen FIG. 29—ELISA detection of specific IgG titers from murine serum (diluted 16,000) after immunization with vaccines comprising PIKA and/or whole inactivated SARS antigen FIG. 30—ELISA detection of specific antibody H5 titers from chicken serum after immunization with vaccines comprising PIKA and/or inactivated H5N1 antigen FIG. 31—ELISA detection of specific H9 antibody titers from chicken serum after immunization with vaccines comprising PIKA and/or inactivated H5N1 antigen FIG. 32—Survival rate of mice exposed to wild rabies virus and subsequent treatment with rabies vaccine FIG. 33—ELISA detection of specific antibody titers from murine serum after immunization with vaccines comprising PIKA and/or HBsAg adw FIG. 34—ELISA detection of specific antibody titers from murine serum after immunization with vaccines comprising PIKA and/or inactivated split influenza antigen FIG. 35—ELISA detection of specific IgG1 titers from murine serum after immunization with vaccines comprising PIKA and/or HBsAg FIG. 36—ELISA detection of specific IgG2a titers from murine serum after immunization with vaccines comprising PIKA and/or HBsAg FIG. 37—ELISPOT detection of murine splenocytes producing interferon-γ after immunization with vaccines comprising PIKA and/or HBsAg FIG. 38—ELISPOT detection of murine splenocytes (post restimulation 6 days with 2 ug/ml IPQ peptide) producing interferon-γ after immunization with vaccines comprising PIKA and/or HBsAg Table 1 provides a table of exemplary viral pathogens which can serve as a source of antigen and diseases associated with these organisms.

Table 2 provides a table of exemplary bacterial pathogens which can serve as a source of antigen and diseases associated with these organisms.

Table 3 provides a table of exemplary fungal pathogens which can serve as a source of antigen and diseases associated with these organisms.

Table 4 provides a table of exemplary parasites which can serve as a source of antigen and diseases associated with these organisms.

Table 5 provides a table of exemplary cancers (e.g., by tissue type) which serve as a source of antigen.

DETAILED DESCRIPTION OF EXEMPLARY EMBODIMENTS OF THE INVENTION

The present invention may be understood more readily by reference to the following detailed description of certain embodiments of the invention and the Examples included herein.

Throughout this application, where publications are referenced, the disclosures of these publications are hereby incorporated by reference, in their entireties, into this application in order to describe more fully the state of art to which this invention pertains.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an immunogenic composition" includes a plurality of such compositions and reference to "the antigen" includes reference to one or more antigens and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

DEFINITIONS OF TERMS

Prior to setting forth details of the present invention it may be useful to an understanding thereof to set forth definitions of several terms that are used herein.

The term "adjuvant," as used herein, refers to any substance or mixture of substances that increases or diversifies the immune response of a host to an antigenic compound. Specifically:
1. The term "PICKCa" generally refers to a composition of poly I:C, kanamycin and calcium irrespective of particular physical and immunogenic properties.
2. "Av-PICKCa" refers to a form of PICKCa used commercially as an antiviral drug.

3. "PIKA" refers to a composition of the invention comprising poly I:C, an antibiotic (e.g., kanamycin), and a positive ion (e.g., calcium), where the PIKA is characterized by physical characteristics (e.g., molecular weight, size, and the like) such that upon administration, PIKA exhibits characteristics of an adjuvant with reduced adverse side effects (e.g., reduced toxicity) relative to, for example, PICKCa and greater potency (e.g., stimulates an enhanced immune response) relative to, for example, Av-PICKCa.

The term "Poly I:C" or "PIC" refers to a composition comprising polyriboinosinic and polyribocytidylic nucleic acids, which may also be referred to as polyinosinic acid-polycytidylic acid, respectively.

"PIC-containing molecule" or "PIC-containing compound" refers to, without limitation, PIC, which may be optionally complexed or otherwise combined with at least one or both of an antibiotic (e.g., kanamycin) and a positive ion (e.g., calcium) present in a composition comprising the PIC-containing molecule. In one embodiment, the PIC-containing molecule does not include poly-L-lysine or a derivative thereof in the complex.

"Heterogeneous" as used herein in the context of the adjuvant compositions of the invention indicates that components of the composition, e.g., the PIC-containing molecules, are not uniform with respect to a physical characteristic of molecular weight, size, or both. Where a composition is described as heterogenous for a given physical characteristic, and is further described by a range of values for that physical characteristic, the composition is said to be composed substantially of molecules characterized by molecules having a physical characteristic that is distributed within and across the recited range. While the composition may not contain a molecule representative of every physical characteristic value within the upper and lower limits of a recited range, the composition will generally include at least one molecule having the physical characteristic of the upper value and of the lower value. The composition in certain embodiments may include molecules outside the stated range of physical characteristics used to describe the composition. The molecules that are present in the composition outside the prescribed range do not materially affect the basic and novel characteristics of the composition.

The term "individual," used interchangeably herein with "host," "subject," and "animal," includes humans and all domestic, e.g. livestock and pets, and wild mammals and fowl, including, without limitation, cattle, horses, cows, swine, sheep, goats, dogs, cats, rabbits, deer, mink, chickens, ducks, geese, turkeys, game hens, and the like.

The term "antibody" includes polyclonal and monoclonal antibodies, as well as antigenic compound binding fragments of such antibodies including Fab, F(ab')2, Fd, Fv fragments, and single chain derivatives of the same. In addition, the term "antibody" includes naturally occurring antibodies as well as non-naturally occurring antibodies, including, for example, chimeric, bifunctional and humanized antibodies, and related synthetic isoforms. The term "antibody" is used interchangeably with "immunoglobulin."

As used herein, the term "antigenic compound" refers to any substance that can be recognized by the immune system (e.g., bound by an antibody or processed so as to elicit a cellular immune response) under appropriate conditions.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; viruses; viral extracts; bacteria; bacterial extracts; fungi; fungal extracts; multicellular organisms such as parasites; and allergens. Antigens may be exogenous (e.g., from a source other than the individual to whom the antigen is administered, e.g., from a different species) or endogenous (e.g., originating from within the host, e.g., a diseased element of body, a cancer antigen, a virus infected cell producing antigen, and the like). Antigens may be native (e.g., naturally-occurring); synthetic; or recombinant. Antigens include crude extracts; whole cells; and purified antigens, where "purified" indicates that the antigen is in a form that is enriched relative to the environment in which the antigen normally occurs and/or relative to the crude extract, for example, a cultured form of the antigen.

An "immunogenic composition" as used here in refers to a combination of two or more substances (e.g., an antigen and an adjuvant) that together elicit an immune response when administered to a host.

The term "polypeptide," "peptide," "oligopeptide," and "protein," are used interchangeably herein, and refer to a polymeric form of amino acids of any length, which can include coded and non-coded amino acids, chemically or biochemically modified or derivatized amino acids, and polypeptides having modified peptide backbones.

An "effective amount of an antigenic compound" refers to an amount of antigenic compound which, in optional combination with an adjuvant, will cause the subject to produce a specific immunological response to the antigenic compound.

The term "immune response" refers to any response to an antigenic or immunogenic compound by the immune system of a vertebrate subject. Exemplary immune responses include, but are not limited to local and systemic cellular as well as humoral immunity, such as cytotoxic T lymphocytes (CTL) responses, including antigen-specific induction of $CD8^+$ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is stimulated, initiated, or induced.

The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of antigenic compound sufficient to stimulate an immune response, when administered with a subject immunogenic composition, as compared with the immune response elicited by the antigen in the absence of the polynucleotide adjuvant.

The term "immunopotentiating amount" refers to the amount of the adjuvant needed to effect an increase in antibody titer and/or cell-mediated immunity when administered with an antigenic compound in a composition of the invention, as compared with the increase in antibody and/or cell mediated immunity level observed in the absence of the polynucleotide adjuvant.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, e.g., arresting its development; or relieving the disease symptom, i.e., causing regression of the disease or symptom (c) reduction of a level of a product produced by the infectious agent of a disease (e.g., a toxin, an antigen, and the like); and (d) reducing an undesired physiological response to the infectious agent of a disease (e.g., fever, tissue edema, and the like).

As used herein, the term "mixing" includes any method to combine the components of the composition; such methods include, but are not limited to, blending, dispensing, dissolving, emulsifying, coagulating, suspending, or otherwise physically combining the components of the composition.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "unit dosage form" as used herein refers to physically discrete units suitable as unitary dosages for human and animal subjects, each unit containing a predetermined quantity of compounds of the present invention calculated in an amount sufficient to produce the desired effect in association with a pharmaceutically/physiologically acceptable diluent, carrier or vehicle.

EXEMPLARY EMBODIMENTS OF THE INVENTION

The present invention is directed to immunogenic compositions and methods useful for the induction and/or enhancement of an immune response, which may be humoral and/or cell-mediated, in a human, a non-human animal, or cell culture. In general, a subject immunogenic composition comprises an antigen (an "antigenic composition") and an adjuvant. The presence of the adjuvant enhances or modifies the immune response to the antigen. The adjuvant may alter the quality of the immune response by affecting the subclasses (isotypes) of immunoglobulins, chemokines, and/or cytokines produced. As a result the innate immunity, humoral and/or cell-mediated immune responses are more effective with the presence of the adjuvant.

A particular advantage is the effectiveness of the PIMA adjuvant in combination with an antigenic substance in inducing a specific humoral immune response thereby enhancing protective immunity.

A further important advantage is that the PIKA adjuvant in combination with an antigen can induce a specific cell mediated immune response that is essential for a therapeutic vaccine for limiting and treating intracellular viral, bacterial and parasite infections as well as for chronic diseases therapies such as the treatment of cancers or auto-immune disease.

Accordingly, included in the invention are compositions having the unique product attributes that make them most suitable for use as vaccines to be administered to animals and/or humans that address the need for a safe adjuvant, which elicits a beneficial immune response.

Accordingly, the present invention provides an adjuvant and immunogenic compositions that can be used safely in humans and animals.

Accordingly, there is provided an immunogenic composition comprising: (a) a polynucleotide adjuvant comprising: a polyriboinosinic-polyribocytidylic acid (PIC), at least one an antibiotic, and at least one positive ion; and (b) at least one antigen; wherein the composition is formulated for sustained release administration.

The immunogenic composition according to the invention may comprise a polynucleotide adjuvant composition molecules heterogeneous for molecular weight, wherein the molecular weight is at least 66,000 Daltons. The value of 66,000 Daltons corresponds to the size of about 6.4 Svedbergs. Accordingly, a molecular weight range of 66,000 to 1,200,000 Daltons corresponds to the size from about 6.4 to 24.0 Svedbergs.

In some embodiments, a PIKA adjuvant composition comprising a polynucleotide, an antibiotic and a positive ion, wherein the polynucleotide may be polyriboinosinic-polyribocytidylic acid (PIC); the antibiotic may be kanamycin, and the ion may be calcium.

In one aspect of particular interest, the invention provides for an immunogenic composition for enhancing the antigenicity of an antigenic compound comprising the polynucleotide adjuvant composition that is capable of eliciting an antigen specific cell mediated immune response.

In one aspect of particular interest, the invention provides for an immunogenic composition for enhancing the antigenicity of an antigenic compound comprising the polynucleotide adjuvant composition that is capable of eliciting an antigen specific humoral immune response.

In one aspect of particular interest, the invention provides for an immunogenic composition for enhancing the antigenicity of an antigenic compound comprising the polynucleotide adjuvant composition that is capable of eliciting a combined specific cell mediated and humoral immune response.

In one aspect of particular interest, the invention provides for an adjuvant composition or immunogenic composition comprising an adjuvant composition wherein the adjuvant composition or the immunogenic composition is freeze-dried.

In one aspect of particular interest, the invention provides for the use of a polynucleotide adjuvant composition for the preparation of a medicament for enhancing the immunogenic response of a host.

Polynucleotide Adjuvant

A subject immunogenic composition comprises a PIC-containing polynucleotide adjuvant, e.g., a PIKA composition, is generally composed of polyinosinic acid, polycytidylic acid, an antibiotic (e.g., kanamycin), and a divalent cation (e.g., calcium). It will be understood that reference to PIKA herein is exemplary of such PIC-containing adjuvants.

PIC-containing adjuvants of interest can be manufactured using methods available in the art. The PIC-containing adjuvant composition can be manufactured through any appropriate process. For example the polynucleotide adjuvant composition can be manufactured by mixing of polyinosinic acid, polycytidylic acid, an antibiotic and the source of a positive ion in a sodium chloride/phosphate buffer solution that has a pH between pH6 and pH8. The polyinosinic acid and polycytidylic acid are generally provided at a concentration of 0.1 to 10 mg/ml, usually 0.5 to 5 mg/ml and more usually 0.5 to 2.5 mg/ml. The hyperchromicity value should be greater than 10%, greater than 15%, greater than 20%, or greater than 50%. The preparation of the PIC and the combination with the antibiotic (e.g., kanamycin) and the positive ion (e.g., calcium) is generally conducted under quality standards consistent with international Good Manufacturing Process.

In certain embodiments of the present invention, the antibiotic component of the adjuvant is kanamycin. Where the antibiotic is kanamycin, in some embodiments, the kanamycin in the polynucleotide adjuvant composition is used together with or substituted by one or more antibiotics selected from the group including tobramycin, anthracyclines, butirosin sulfate, gentamicins, hygromycin, amikacin, dibekacin, nebramycin, metrzamide, neomycin, puromycin, streptomycin and streptozocin. The antibiotic (e.g., Kanamycin or the like) in the polynucleotide adjuvant composition of the invention is generally provided at a concentration of from about 10 units/ml to 100,000 units/ml, from about 100 units/ml to 10,000 units/ml, or from about 500 units/ml to 5,000 units/ml.

In certain embodiments of the present invention, the polynucleotide adjuvant composition further comprises a positive ion (cation), usually a divalent cation, normally a cation of an alkali metal. The positive ion is generally provided in the composition of the invention as a source of positive ions such as a salt or complex, e.g., an organic or inorganic salt or complex, usually an inorganic salt or organic complex. Exemplary positive ions include, but are not necessarily limited to, calcium, cadmium, lithium, magnesium, cerium, cesium, chromium, cobalt, deuterium, gallium, iodine, iron, or zinc.

The positive ion can be provided in the form of any suitable salt or organic complex, including, but not necessarily limited to chloride, fluoride, hydroxide, phosphate, or sulfate salts. For example, where the positive ion is calcium, the ion can be in the form of calcium carbonate, calcium chloride, calcium fluoride, calcium hydroxide, calcium phosphates, or calcium sulfate.

The positive ion (e.g. calcium) can be provided in the composition of the invention at a concentration in the range of from about 10 umol to 10 mmol/ml, usually from about 50 umol to 5 mmol/ml, and more usually from about 100 umol to 1 mmol/ml. The term "umol" is used throughout to refer to micromole.

Where the positive ion in the adjuvant composition of the invention is calcium, it can be in combination with or substituted by other positive ions, including cadmium, lithium, magnesium, cerium, cesium, chromium, cobalt, deuterium, gallium, iodine, iron, and zinc, wherein the ions can be in the form of inorganic salts or organic complexes.

The resulting composition is a PIC-containing adjuvant that further contains an antibiotic and a positive ion. In a particular embodiment, where the antibiotic is kanamycin and the ion is calcium the product may be described as PICKCa. In a related embodiment the PICKCa composition may contain molecules without restriction of different physical characteristics.

PIKA Adjuvant Composition

In a particular exemplary embodiments, the PIC-containing adjuvant is PIKA. PIKA may be produced in a variety of ways, with production from PICKCa being of particular interest. PIKA can be produced from PICKCa through additional manufacturing processes that involve the isolation and/or concentration of molecules of a defined molecular size and/or weight. The separation and concentration of polynucleotide molecules of particular characteristics using filtration, chromatography, thermal treatment, centrifugal separation, electrophoresis, and similar methods that are standard processes and are known to those skilled in the art.

In embodiments of particular interest, the invention features an adjuvant generally referred to as PIKA comprising a polyriboinosinic-polyribocytidylic acid (PIC), an antibiotic (e.g., kanamycin), and a positively charged ion (e.g., a calcium ion), wherein the composition contains molecules of the adjuvant heterogeneous for molecular weight having a molecular weight of from about 66,000 to 1,200,000 Daltons. That is, the adjuvant composition comprises molecules with a weight distribution in the range of from about 66,000 to 1,200,000 Daltons.

In related embodiments, the PIKA polynucleotide adjuvant composition molecules in the composition are heterogeneous, that is the weight of the adjuvant molecules are distributed within a range of molecular weight, where the molecular weight is from about 300,000 to 1,200,000 Daltons, or from about 66,000 to 660,000 Daltons, or from about 300,000 to 660,000 Daltons, or from about 300,000 to 2,000,000 Daltons, or from about 66,000 Daltons to about 100,000 Daltons, 100,000 to 200,000 Daltons, from about 300,000 Daltons to about 4,000,000 Daltons, or from about 500,000 Daltons to 1,000,000 Daltons, or from about 1,000,000 Daltons to 1,500,000 Daltons, or from about 1,500,000 Daltons to 2,000,000 Daltons, or from about 2,000,000 Daltons to 2,500,000 Daltons, or from about 2,500,000 Daltons to 3,000,000 Daltons, or from about 3,000,000 Daltons to 3,500,000 Daltons, or from about 3,500,000 Daltons to 4,000,000 Daltons, or from about 4,000,000 Daltons to 4,500,000 Daltons, or from about 4,500,000 Daltons to 5,000,000 Daltons.

In related embodiments, the PIKA polynucleotide adjuvant composition molecules in the composition have an average molecular weight equal or equal to or greater than 66,000 Daltons, greater than 150,000 Daltons, or equal to or greater than 250,000 Daltons, or equal to or greater than 350,000 Daltons, or equal to or greater than 500,000 Daltons, or equal to or greater than 650,000 Daltons, or equal to or greater than 750,000 Daltons, or equal to or greater than 1,000,000 Daltons, or equal to or greater than 1,200,000 Daltons, or equal to or greater than 1,500,000 Daltons, or equal to or greater than 2,000,000 Daltons.

In embodiments of particular interest, the invention features an adjuvant generally referred to as PIKA comprising a polyriboinosinic-polyribocytidylic acid (PIC), an antibiotic, and a positive ion wherein the composition contains molecules of the adjuvant heterogeneous, that is the size of the adjuvant molecules are distributed within a range of molecular size, for molecular size having a sediment co-efficient Svedbergs (S) of from about 6.43 S to 24.03 S.

In related embodiments, the PIKA polynucleotide adjuvant composition molecules in the composition are heterogeneous, that is the size of the adjuvant molecules are distributed within a range of molecular size, where the molecular size is from about 12.8 S to 24.03 S, or from about 3 S to 12 S or from about 6.43 to 18.31 S, or from about 12.8 to 18.31 S, or from about 12.8 S to 30.31 S, or from about 12.8 S to 41.54 S, or from about 13.5 S, to 18.31 S, or from about 13.5 S to 24.03 S, or from about 16.14 to 22.12 S, or from about 22.12 S to 26.6 S, or from about 26.6 S to 30.31 S, or from about 30.31 S to 33.55 S, or from about 33.55 S to 36.45 S, or from about 36.45 S to 39.1 S, or from about 39.1 S to 41.54 S, or from about 41.54 S to 43.83 S, or from about 43.83 S to 45.95 S.

In further related embodiments, the PIKA polynucleotide adjuvant composition has an average sedimentation co-efficient (Svedbergs) greater than 9, or greater than 12, or greater than 13.5, or greater than 15, or greater than 16, or greater than 17, or greater than 18, or greater than 19, or greater than 20, or greater than 21, or greater than 22 or greater than 25, or greater than 30.

Immunogenic Properties

An immunogenic composition, including PIKA and an antigen, can generally induce an antigen-specific immune response in at least two ways: i) humoral-mediated immunity, which includes B cell stimulation and production of antibodies or immunoglobulins (other cells are also involved in the generation of an antibody response, e.g. antigen-presenting cells, including macrophages and helper T cells (Th1 and Th2), and ii) cell-mediated immunity, which generally involves T cells including cytotoxic T lymphocytes, although other cells are also involved in the generation of a cytotoxic T lymphocyte response (e.g., Th1 and/or Th2 cells and antigen presenting cells).

Furthermore, the polynucleotide adjuvant composition may alter the quality of the immune response by affecting the subclasses (isotypes) of immunoglobulins produced, as well as their affinities.

The degree and nature of the immunogenic response induced by a subject immunogenic composition may be thus assessed by measuring the presence of molecules including cytokines, chemokines and antibodies produced by cells of the immune system.

Interleukin-4 is mainly produced by activated Th2 cells. The production of Interleukin-4 (IL-4) induces the activation of B cells and thereby the production of IgG1 and IgE immunoglobulins (antibodies) which may be measured in the samples of blood serum. IL-4 is considered as an indictor and typical cytokine of Th2 immune response. Th2 cells tend to promote antibody response.

Interleukin-2 (IL-2) is mainly produced by activated Th1 cell as well as NK and lymphokine-activated killer (LAK) cells. IL-2 is instrumental in the proliferation and maturing of T cells an essential stage in an effective cell mediated adaptive immune response.

Interferon-γ (INF-γ), which may be produced by a variety of cells including natural killer cells as well as both $CD4^+$ and $CD8^+$ T cells, plays an essential part in the adaptive immune response including the activation of macrophages to become highly microbicidal. Further, INF-γ is an influencing factor in directing the development of specifically Th1 T cells thereby up-regulating a cell mediated adaptive immune response.

The invention contemplates methods of use of the polynucleotide adjuvant of the invention with an antigen, for example, to elicit an antigen specific humoral response and/or specific cellular (e.g., T cell) response in a subject. The immune response elicited may be a response to an antigen in a naïve subject, or may serve to enhance an existing immune response (e.g., as in a booster). It has been found that immunogenic compositions according to the invention comprising PIKA have particularly advantageous properties as described herein.

A variety of different antigens were tested in vivo for their ability to induce an immune response with and without the PIKA adjuvant. The antigens tested include: a recombinant protein hepatitis B surface antigen type adw, an inactivated split influenza vaccine (VAXIGRIP from Sanofi Pasteur), a synthesized HIV peptide antigen, a recombinant protein herpes simplex virus type 2 gD antigen, recombinant protective anthrax protein antigen, inactivated whole virus avian influenza antigen strain H5N1 and an inactivated whole virus Severe Acute Respiratory Syndrome (SARS) inactivated antigen.

In each case presence of the PIKA adjuvant together with the antigen enhanced the expression of cytokines when compared with the antigen or PIKA alone. In particular the enhanced expressions of the cytokines INF-γ, IL-2 and IL-4 (see Examples 1.1, 1.2, 1.3, 1.4, 1.5 and 1.6) indicates the stimulation of a specific adaptive immunity was greater with the presence of the PIKA adjuvant and more specifically the enhanced expressions of the cytokines INF-γ, IL-2 indicates the predominant Th1 cell immunity was significantly improved with the presence of the PIKA adjuvant. The activity of a cell mediated immune response is a key feature essential for treating intracellular viral, bacterial and parasite infection and particularly important factor for developing a therapeutic vaccine.

Further the composition containing PIKA stimulated INF-γ production by CD4+ T cells (Examples 1.3, 1.4, 1.5 and 1.6). This feature validates that PIKA is enhancing the adaptive immune response of the host.

The observed proliferation of antibodies in the blood serum demonstrates that the PIKA adjuvant induces a beneficial humoral response. Increased specific antibody IgG titers were observed with the addition of PIKA to an immunogenic composition (see Examples 1.1, 1.2, 1.4, 1.5, 1.6, 2, 3, 5 and 6).

The PIKA adjuvant enhances the immune response in a host when combined with a inactivated antigen (Examples 1.2, 1.6, 2, 3, 4 and 6), a peptide antigen (Example 1.3) and a recombinant antigen (Examples 1.1, 1.4, 1.5, 5 and 7).

A particular feature of the PIKA adjuvant is to provide adequate protection to both limit and/or eradicate infection in a host, and/or to reduce the risk of symptoms of a disease that could result from infection by a pathogen. VAXIGRIP (Sanofi Pasteur) used as an antigen in Examples 1.2 and 6 is itself a human influenza vaccine that elicits a degree of immune activity considered sufficient to provide protection against an actual influenza infection. The addition of PIKA to VAXIGRIP further enhanced the immune response as demonstrated by the degree of beneficial cytokines (IL-2, INF-γ and IL-4) and specific IgG expressed by the immune system.

In a further demonstration of PIKA's protective properties, 24 ten-day old chickens were inoculated with a composition comprising PIKA and inactivated avian influenza antigens including strains H5N1 and H9N2 (Example 3). The chickens were subsequently challenged with the live H5N1 virus and observed for a two week period. At the end of the program the survival rate for the chickens inoculated with the PIKA/antigen composition was 83% as compared with only 17% for a control group of 24 chickens that were exposed to the live virus without prior inoculation with the PIKA/antigen composition.

In a related experiment to demonstrate the therapeutic enhancing properties of the PIKA adjuvant, Balb/c mice were challenged with a strain of wild rabies virus (Example 4). Post infection the three different groups of animals were inoculated with a regime of treatments with different rabies vaccines. The survival rate of the group of mice inoculated with a combination of an inactivated purified hamster kidney cell rabies antigen plus PIKA attained 80%. The survival rate of the second group of mice administered with a hamster kidney cell purified rabies antigen with an alum adjuvant was 15%. Further the third group of mice administered with the Sanofi-Aventis' "Verorab"—vero cell inactivated rabies vaccine had a survival rate of 20%.

In a further demonstration of the properties of the PIKA adjuvant, Example 7 demonstrates that the presence of PIKA in conjunction with HBsAg type adw enhances the production of specific IgG1 (Table 26 FIG. 35) and more significantly IgG2a (Table 27 FIG. 36) titers in murine serum. The conclusion from this observation is that PIKA enhances a therapeutic immune response in particular a Th1 biased immune response.

In a related experiment (Example 7) the presence of PIKA in vaccine formulations comprising HBsAG type adw was shown to enhance the production of interferon-γ by splenocytes stimulated with a CD8 T cell peptide epitope. This result demonstrates that PIKA induces a CD8+ T cell immune response (Table 28 FIG. 37).

Further, (Example 7) the presence of PIKA in vaccine formulations comprising HBsAg was shown to enhance the production of interferon-γ by splenocytes cultured ex-vivo for six days with 2 ug/ml of the CD8 T cell peptide epitope. This result demonstrates that PIKA induces a central memory T cell response.

Additional Features

In a further embodiment, a subject immunogenic composition is further defined by the relative presence of the PIKA adjuvant and the antigen or antigens where the presence is measured in terms of one or more characteristics of quantity, concentration, volume, number of molecules or other recognized metric.

In related embodiments, a subject immunogenic composition comprises a polynucleotide adjuvant composition and an antigen or antigens where the presence of the adjuvant and the antigen in terms of weight or number of molecules is in a ratio of less than 1 to 1,000, of less than 1 to 900, of less than 1 to 800, of less than 1 to 700, of less than 1 to 500, of less than 1 to 400, of less than 1 to 300, of less than 1 to 200, of less than 1 to 100, of less than 1 to 50, of less than 1 to 10, of less than 1 to 5, of less than 1 to 2, of about 1 to 1, of greater than 2 to 1, of greater than 5 to 1, of greater than 10 to 1, of greater than 50 to 1, of greater than 100 to 1, of greater than 200 to 1, of greater than 300 to 1, of greater than 400 to 1, of greater than 500 to 1, of greater than 600 to 1, of greater than 700 to 1, of greater than 800 to 1, of greater than 900 to 1, of greater than 1,000 to 1

In a further related embodiment a subject immunogenic composition is defined in terms of dose; that is the quantity of vaccine that is to be administered to induce the optimal beneficial immune response or alternatively the range of dose that may be administered from the minimum required to elicit an immune response to the maximum dose beyond which the incremental beneficial response is not medically justified in the context of the potential inducement of adverse side effects.

In certain embodiments of particular interest the immunogenic composition comprises the polynucleotide adjuvant composition and antigen where the presence of the antigen in a unit dose is provided in a quantity, that is more than 0.1 ug, is more than 0.5 ug, is more than 0.001 mg is more than 0.005 mg, is more than 0.01 mg, is more than 0.025 mg, is more than 0.05 mg, is more than 0.075 mg, 0.1 mg is more than 0.25 mg, is more than 0.5 mg, is more than 1.2 mg, is more than 1.4 mg, is more than 1.6 mg, is more than 1.8 mg, is more than 2.0 mg is more than 2.5 mg, is more than 3 mg, is more than 3.5 mg, is more than 4 mg, is more than 5 mg, is more than 6 mg, is more than 7 mg, is more than 8 mg, is more than 9 mg, is more than 10 mg, is more than 15 mg, is more than 20 mg, is more than 25 mg, or is more than 50 mg.

An optimal amount of antigen and the optimal ratio of antigen to PIKA adjuvant can be ascertained by standard studies involving observations of antibody titers and other immunogenic responses in the host.

Antigens

In an embodiment of particular interest the invention provides for a polynucleotide adjuvant composition together with an antigen or vaccine where the source of the antigen is a human antigen, a animal antigen, a plant antigen, one or more agents from infectious agents from any virus, bacteria including mycobacterium, fungus or parasite, cancer antigen, allergenic agents and other antigens, such as for developing autoimmune diseases.

In certain embodiments, the antigens may be derived from a natural source either crude or purified and used in its original live form or after having been killed, or inactivated, or truncated, or attenuated, or transformed into a nonreverting form, or detoxified, or mutated into a nontoxic form, or filtered or purified.

In some embodiments, the antigen is an isolated microorganism antigen for example, a viral antigen, a bacterial antigen, a fungal antigen, an allergy antigen, a cancer antigen or an autoimmune antigen. In other embodiments, the antigen is a whole, inactivated antigen. Methods of inactivating a whole antigens are well known in the art; any known method can be used to inactivate an antigen and can be selected appropriately for the type of antigen of interest. Such methods of inactivating an antigen include for example, use of photoreactive compounds; oxidizing agents; irradiation (e.g., UV irradiation; γ-irradiation); combinations of riboflavin and UV irradiation; solvent-detergent treatment (e.g., treatment with organic solvent tri-N-butyl-phosphate with a detergent such as Tween 80); polyethylene glycol treatment; pasteurization (heat treatment); and low pH treatment; mild enzymatic treatment with pepsin or trypsin; Methylene blue (MB) phototreatment; treatment with Dimethylmethylene blue (DMMB) and visible light; treatment with S-59, a psoralen derivative and UVA illumination; and the like.

In a related embodiment of particular interest the antigen may be synthesized by means of solid phase synthesis, or may be obtained by means of recombinant genetics, or may be otherwise manufactured artificially so as to imitate the immunogenic properties of a pathogen.

Polypeptide antigens may be isolated from natural sources using standard methods of protein purification known in the art, including, but not limited to, liquid chromatography (e.g., high performance liquid chromatography, fast protein liquid chromatography, etc.), size exclusion chromatography, gel electrophoresis (including one-dimensional gel electrophoresis, two-dimensional gel electrophoresis), affinity chromatography, or other purification technique. One may employ solid phase peptide synthesis techniques, where such techniques are known to those of skill in the art. See Jones, *The Chemical Synthesis of Peptides* (Clarendon Press, Oxford) (1994). Generally, in such methods a peptide is produced through the sequential additional of activated monomeric units to a solid phase bound growing peptide chain. Well-established recombinant DNA techniques can be employed for production of polypeptides, such methods include, but are not limited to, for example, an expression construct comprising a nucleotide sequence encoding a polypeptide is introduced into an appropriate host cell (e.g., a eukaryotic host cell grown as a unicellular entity in in vitro cell culture, e.g., a yeast cell, an insect cell, a mammalian cell, etc.) or a prokaryotic cell (e.g., grown in in vitro cell culture), generating a genetically modified host cell; under appropriate culture conditions, the protein is produced by the genetically modified host cell.

In some embodiments, the antigen is a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

The antigen may be acellular, capsular, infectious clone, replicon, vectored, micro encapsulated, monovalent, bivalent or multivalent.

The polynucleotide adjuvant composition of the present invention can also be utilized to enhance the immune response against antigens produced by the use of DNA vaccines and/or DNA expressed proteins. The DNA sequences in these vaccines coding for the antigen can be either "naked" or contained in a delivery system, such as liposomes.

In one aspect of particular interest a subject immunogenic composition may be defined by the selection of antigen or antigens that are used in combination with the PIKA adjuvant.

More specifically, the present invention provides for an immunogenic composition and method of use where the immunogenic composition comprises a PIKA adjuvant together with a viral antigen, wherein exemplary antigens include but are not limited to antigens of one or more of the viruses described in Table 1.

TABLE 1

| | Viral pathogens and diseases | |
|---|---|---|
| | Viral Taxonomy | Disease |
| 1 | Adenoviridae | |
| 2 | Mastadenovirus | |
| 3 | Human adenovirus A to F | Common cold |
| 4 | Arenaviridae | |
| 5 | Old world arenaviruses | |
| 6 | Ippy virus | |
| 7 | Lassa virus | Lassa fever |
| 8 | Lymphocytic choriomeningitis virus | Lymphocytic choriomeningitis disease |
| 9 | Astroviridae | |
| 10 | Mamastrovirus | |
| 11 | Human astrovirus | Gastroenteritis |
| 12 | Bunyaviridae | |
| 13 | Hantavirus | |
| 14 | Hantaan virus | Korean hemorrhagic fever |
| 15 | Nairovirus | |
| 16 | Crimean-Congo hemorrhagic fever virus | Hemorrhagic Fevers |
| 17 | Orthobunyavirus | |
| 18 | California encephalitis virus | La Crosse Encephalitis |
| 19 | Phlebovirus | |
| 20 | Rift Valley fever virus | Rift Valley Fever |
| 21 | Caliciviridae | |
| 22 | Norovirus | |
| 23 | Norwalk virus | Diarrhea |
| 24 | Flaviviridae | |
| 25 | Flavivirus | |
| 26 | Dengue virus group | Dengue |
| 27 | Japanese encephalitis virus group | |
| 28 | Japanese encephalitis virus | Japanese encephilitis |
| 29 | St. Louis encephalitis virus | St. Louis encephalitis disease |
| 30 | West Nile virus | West Nile virus disease |
| 31 | tick-borne encephalitis virus group | Tick-borne encephalitis |
| 32 | Yellow fever virus group | Yellow fever |
| 33 | Hepacivirus | |
| 34 | Hepatitis C virus | Hepatitis C |
| 35 | Hepatitis G virus | Hepatitis G |
| 36 | Hepadnaviridae | |
| 37 | Orthohepadnavirus | |
| 38 | Hepatitis B virus | Hepatitis B |
| 39 | Hepatitis delta virus | Hepatitis D |
| 40 | Hepeviridae | |
| 41 | Hepevirus | |
| 42 | Hepatitis E virus | Hepatitis E |
| 43 | Herpesviridae | |

TABLE 1-continued

Viral pathogens and diseases

| | Viral Taxonomy | Disease |
|---|---|---|
| 44 | Alphaherpesvirinae | |
| 45 | Simplexvirus | |
| 46 | Cercopithecine herpesvirus 1 | B Virus Infection |
| 47 | Human herpesvirus 1 | Herpes simplex type 1 |
| 48 | Human herpesvirus 2 | Herpes simplex type 2 |
| 49 | Varicellovirus | |
| 50 | Human herpesvirus 3 (Varicella zoster virus) | Chicken pox, Shingels |
| 51 | Betaherpesvirinae | |
| 52 | Cytomegalovirus | |
| 53 | Human herpesvirus 5 | Cytomegalovirus (CMV) |
| 54 | Roseolovirus | |
| 55 | Human herpesvirus 6 | Herpes |
| 56 | Human herpesvirus 7 | Herpes |
| 57 | Gammaherpesvirinae | |
| 58 | Lymphocryptovirus | |
| 59 | Human herpesvirus 4 | Epstein-Barr virus Infection |
| 60 | Rhadinovirus | |
| 61 | Human herpesvirus 8 | Herpes |
| 62 | Mononegavirales | |
| 63 | Filoviridae | |
| 64 | Ebola-like viruses | |
| 65 | Ebola virus | Ebola disease |
| 66 | Marburgvirus | Marburg hemorrhagic fever |
| 67 | Paramyxoviridae | |
| 68 | Paramyxovirinae | |
| 69 | Henipavirus | |
| 70 | Hendra virus | Hendra virus disease |
| 71 | Morbillivirus | |
| 72 | Measles virus | Measles |
| 73 | Respirovirus | |
| 74 | Human parainfluenza virus 1 | Human parainfluenza virus |
| 75 | Human parainfluenza virus 3 | Human parainfluenza virus |
| 76 | Rubulavirus | |
| 77 | Human parainfluenza virus 2 | Human parainfluenza virus |
| 78 | Human parainfluenza virus 4 | Human parainfluenza virus |
| 79 | Mumps virus | Mumps |
| 80 | Pneumovirinae | |
| 81 | Metapneumovirus | |
| 82 | Human metapneumovirus | Human metapneumovirus |
| 83 | Pneumovirus | |
| 84 | Human respiratory syncytial virus | Human respiratory syncytial disease |
| 85 | Rhabdoviridae | |
| 86 | Lyssavirus | |
| 87 | Rabies virus | Rabies |
| 88 | Nidovirales | |
| 89 | Coronaviridae | |
| 90 | Coronavirus | |
| 91 | Group 2 species | |
| 92 | Human coronavirus | Coronovirus |
| 93 | SARS coronavirus | SARS |
| 94 | Torovirus | |
| 95 | Human torovirus | Torovirus disease |
| 96 | Picornaviridae | |
| 97 | Aphthovirus | |
| 98 | Equine rhinitis A virus | |
| 99 | Foot-and-mouth disease virus | Foot-and-mouth disease virus |
| 100 | Enterovirus | |
| 101 | Human enterovirus A | |
| 102 | Human coxsackievirus | Human coxsackievirus |
| 103 | Human enterovirus | Human enterovirus |
| 104 | Human enterovirus B | |
| 105 | Enterovirus | Human enterovirus |
| 106 | Human coxsackievirus | Human coxsackievirus |
| 107 | Human echovirus | Human echovirus |
| 108 | Human enterovirus C | |
| 109 | Human coxsackievirus | Human coxsackievirus |
| 110 | Human enterovirus D | |
| 111 | Human enterovirus | Human enterovirus |
| 112 | Poliovirus | |
| 113 | Human poliovirus | Polio |
| 114 | Human enterovirus sp. | Human enterovirus |
| 115 | unclassified Enteroviruses | |
| 116 | Human enterovirus sp. | Human enterovirus |
| 117 | Hepatovirus | |
| 118 | Hepatitis A virus | Hepatitis A virus |

TABLE 1-continued

Viral pathogens and diseases

| | Viral Taxonomy | Disease |
|---|---|---|
| 119 | Parechovirus | |
| 120 |   Human parechovirus | Human parechovirus |
| 121 |     Human parechovirus | |
| 122 | Rhinovirus (common cold viruses) | |
| 123 |   Human rhinovirus A | |
| 124 |     Human rhinovirus | Common cold |
| 125 |   Human rhinovirus B | |
| 126 |     Human rhinovirus | Common cold |
| 127 |   unclassified Rhinovirus | |
| 128 |     Human rhinovirus | Common cold |
| 129 | Orthomyxoviridae | |
| 130 |   Influenzavirus A | |
| 131 |     Influenza A virus | Influenza |
| 132 |   Influenzavirus B | |
| 133 |     Influenza B virus | Influenza |
| 134 |   Influenzavirus C | |
| 135 |     Influenza C virus | Influenza |
| 136 | Paramyxoviridae | |
| 137 |   Paramyxovirinae | |
| 138 |     Henipavirus | |
| 139 |       Hendra virus | Hendra virus |
| 140 | Papillomaviridae | |
| 141 |   Alphapapillomavirus | |
| 142 |     Human papillomavirus | Human papillomavirus |
| 143 |   Betapapillomavirus | |
| 144 |     Human papillomavirus | Human papillomavirus |
| 145 |   Gammapapillomavirus | |
| 146 |     Human papillomavirus | Human papillomavirus |
| 147 |   Mupapillomavirus | |
| 148 |     Human papillomavirus | Human papillomavirus |
| 149 |   unclassified Papillomaviridae | |
| 150 |     Human papillomavirus types | Human papillomavirus |
| 151 | Parvoviridae | |
| 152 |   Parvovirinae | |
| 153 |   Erythrovirus | |
| 154 |     Human parvovirus | |
| 155 |     unclassified Erythrovirus | |
| 156 |       Human erythrovirus | Human erythrovirus |
| 157 | Polyomaviridae | |
| 158 |   Polyomavirus | |
| 159 |     JC polyomavirus | Progressive multifocal leukencephalopathy |
| 160 | Poxviridae | |
| 161 |   Chordopoxvirinae | |
| 162 |     Orthopoxvirus | |
| 163 |       Monkeypox virus | Monkey pox |
| 164 |       Variola virus | Smallpox |
| 165 | Reoviridae | |
| 166 |   Rotavirus | |
| 167 |     Rotavirus A | Diarrhea |
| 168 |     Rotavirus B | Diarrhea |
| 169 |     Rotavirus C | Diarrhea |
| 170 | Retroviridae | |
| 171 |   Orthoretrovirinae | |
| 172 |     Deltaretrovirus | |
| 173 |       Primate T-lymphotropic virus 1 | |
| 174 |         Human T-lymphotropic virus 1 | Human T-lymphotropic virus |
| 175 |       Primate T-lymphotropic virus 2 | |
| 176 |         Human T-lymphotropic virus 2 | Human T-lymphotropic virus |
| 177 |       Primate T-lymphotropic virus 3 | |
| 178 |         Human T-lymphotropic virus 3 | Human T-lymphotropic virus |
| 179 |     Lentivirus | |
| 180 |       Primate lentivirus group | |
| 181 |         Human immunodeficiency virus type 1 and type 2 | HIV |
| 182 |   unclassified Retroviridae | |
| 183 |     Aids-associated retrovirus | |
| 184 |     Human endogenous retroviruses | |
| 185 | Togaviridae | |
| 186 |   Alphavirus | |
| 187 |     EEEV complex | |
| 188 |       Eastern equine encephalitis virus | Eastern equine encephalitis |
| 189 |     SFV complex | |
| 190 |       Chikungunya virus | Chikungunya fever |
| 191 |     VEEV complex | |
| 192 |       Venezuelan equine encephalitis virus | Venezuelan equine encephalitis |
| 193 |     WEEV complex | |

TABLE 1-continued

| | Viral pathogens and diseases | |
|---|---|---|
| | Viral Taxonomy | Disease |
| 194 | Western equine encephalomyelitis virus | Western equine encephaalitis |
| 195 | Rubivirus | |
| 196 | Rubella virus | Rubella, German Measels |

More specifically, the present invention provides for an immunogenic composition and method of use where the immunogenic composition comprises a PIKA adjuvant together with a bacterial antigen, wherein exemplary antigens include but are not limited to antigens of one or more of the bacteria described in Table 2.

TABLE 2

| | Bacterial pathogens and diseases | |
|---|---|---|
| | Bacterial Taxonomy | Disease |
| 1 | Actinobacteria | |
| 2 | Actinobacteria (class) (high G + C Gram-positive bacteria) | |
| 3 | Acidimicrobidae | |
| 4 | Actinobacteridae | |
| 5 | Actinomycetales | |
| 6 | Corynebacterineae | |
| 7 | Corynebacteriaceae | |
| 8 | *Corynebacterium* | |
| 9 | *Corynebacterium diptheriae* | Diphtheria |
| 10 | Actinobacteridae | |
| 11 | Actinomycetales | |
| 12 | Corynebacterineae | |
| 13 | Mycobacteriaceae | |
| 14 | *Mycobacterium* | |
| 15 | *Mycobacterium abscessus* | *Mycobacterium abscessus* infection |
| 16 | *Mycobacterium avium* complex | *Mycobacterium abscessus* infection |
| 17 | *Mycobacterium leprae* | Leprosy/Hansen's Disease |
| 18 | *Mycobacterium tuberculosis* | *Mycobacterium tuberculosis* Infection |
| 19 | Nocardiadeae | |
| 20 | *Nocardia* | |
| 21 | *Nocardia asteroides* | Nocardiosis |
| 22 | *Nocardia farcinica* | Nocardiosis |
| 23 | *Nocardia nova* | Nocardiosis |
| 24 | *Nocardia transvalensis* | Nocardiosis |
| 25 | *Nocardia brasiliensis* | Nocardiosis |
| 26 | *Nocardia pseudobrasiliensis* | Nocardiosis |
| 27 | | |
| 28 | Chlamydiae/Verrucomicrobia group | |
| 29 | Chlamydiae | |
| 30 | Chlamydiae (class) | |
| 31 | Chlamydiales | |
| 32 | Chlamydiaceae | |
| 33 | *Chlamydia* | |
| 34 | *Chlamydia trachomatis* | *Chlamydia* |
| 35 | *Chlamydia pneumoniae* | Pneumonia |
| 36 | *Chlamydia psittaci* | Psittacosis |
| 37 | *Chlamydia trachomatis*, serovars A, B, Ba, and C | *Trachoma* |
| 38 | *Chlamydophila pneumoniae* | Pneumonia |
| 39 | Firmicutes (Gram-positive bacteria) | |
| 40 | Bacilli | |
| 41 | Bacillales | |
| 42 | Bacillaceae | |
| 43 | *Bacillus* | |
| 44 | *Bacillus cereus* group | |
| 45 | *Bacillus anthracis* | Anthrax |
| 46 | Listeriaceae | |
| 47 | *Listeria* | |
| 48 | *Listeria monocytogenes* | Listeriosis |
| 49 | Staphylococcaceae | |
| 50 | *Staphylococcus* | |
| 51 | *Staphylococcus aureus* | Toxic Shock Syndrome |
| 52 | *Staphylococcus aureus* | Methicillin Resistant *Staphylococcus aureus* (MRSA) |
| 53 | *Staphylococcus aureus* VISA and VRSA | *Staphylococcus aureus* (VISA/VRSA) Infections |
| 54 | Lactobacillales | |
| 55 | Streptococcaceae | |

TABLE 2-continued

Bacterial pathogens and diseases

| | Bacterial Taxonomy | Disease |
|---|---|---|
| 56 | *Streptococcus* | Streptococcal Diseases |
| 57 | Group A *streptococcus* | Scarlet Fever |
| 58 | Group B *streptococcus* | Meningitis |
| 59 | *Streptococcus pneumoniae* | Pneumonia |
| 60 | Clostridia | |
| 61 | Clostridiales | |
| 62 | Clostridaceae | |
| 63 | *Clostridium* | |
| 64 | *Clostridium botulinum* | Botulism |
| 65 | *Clostridium difficile* | Diarrhea |
| 66 | *Clostridium tetani* | Tetanus Disease |
| 67 | Mollicutes | |
| 68 | Mycoplasmatales | |
| 69 | Mycoplasmataceae | |
| 70 | *Mycoplasma* | |
| 71 | *Mycoplasma* pneumonia | *Mycoplasma pneumoniae* Infection |
| 72 | Proteobacteria (purple bacteria and relatives) | |
| 73 | Alphaproteobacteria | |
| 74 | Rhizobiales (rhizobacteria) | |
| 75 | Bartonellaceae | |
| 76 | *Bartonella* | |
| 77 | *Bartonella henselae* | Cat Scratch Disease |
| 78 | Brucellaceae | |
| 79 | *Brucella* | Brucellosis |
| 80 | | |
| 81 | Rickettsiales (rickettsias) | |
| 82 | Anaplasmataceae | |
| 83 | Anaplasma | Typhus Fevers |
| 84 | Ehrlichia | Typhus Fevers |
| 85 | Rickettsiaceae | |
| 86 | Rickettsieae | |
| 87 | *Orientia* | |
| 88 | *Orientia tsutsugamushi* | Typhus Fevers |
| 89 | *Rickettsia* | |
| 90 | Spotted fever group | |
| 91 | *Rickettsia rickettsii* | *Rickettsia rickettsii* Infection |
| 92 | *Rickettsia prowazekii* | Typhus Fevers |
| 93 | *Rickettsia typhi* | Typhus Fevers |
| 94 | | |
| 95 | Betaproteobacteria | |
| 96 | Burkholderiales | |
| 97 | Alcaligenaceae | |
| 98 | *Bordetella* | |
| 99 | *Bordetella pertussis* | *Pertussis* |
| 100 | Burkholderiaceae | |
| 101 | *Burkholderia* | |
| 102 | *Burkholderia cepacia* complex | |
| 103 | *Burkholderia cepacia* | *Burkholderia cepacia* Infection |
| 104 | *Burkholderia pseudomallei* | Melioidosis |
| 105 | Neisseriales | |
| 106 | Neisseriaceae | |
| 107 | *Neisseria* | |
| 108 | *Neisseria gonorrhoeae* | Gonorrhea |
| 109 | *Neisseria meningitidis, meningococcus* | Meningitis |
| 110 | delta/epsilon subdivisions | |
| 111 | Epsilonproteobacteria | |
| 112 | Camplobacterales | |
| 113 | Campylobacteraceae | |
| 114 | *Campylobacter* | *Campylobacter* Infection |
| 115 | *Campylobacter jejuni* | Diarrhea |
| 116 | Helicobacteraceae | |
| 117 | *Heliobacter* | |
| 118 | *Heliobacter pylori* | *Helicobacter pylori* Infection |
| 119 | Gammaproteobacteria | |
| 120 | Enterobacteriales | |
| 121 | Entrobacteriaceae | |
| 122 | *Escherichia* | |
| 123 | *Escherichia coli* | Dysentery |
| 124 | *Salmonella* | Salmonellosis |
| 125 | *Salmonella typhi* | *Salmonella typhi* Infection/Typhoid |
| 126 | *Shigella* | |
| 127 | *Shigella dysenteriae* | Dysentery |
| 128 | *Shigella flexneri* | Diarrhea |
| 129 | *Shigella sonnei* | Shigellosis |
| 130 | *Yersinia* | Yersiniosis |
| 131 | *Yersinia pestis* | Plague |

TABLE 2-continued

Bacterial pathogens and diseases

| | Bacterial Taxonomy | Disease |
|---|---|---|
| 132 | Legionellales | |
| 133 | Coxiellaceae | |
| 134 | *Coxiella* | |
| 135 | *Coxiella burnetii* | Q Fever |
| 136 | Legionellaceae | |
| 137 | *Legionella* | |
| 138 | *Legionella pneumophila* | Legionellosis/Legionnaire's Disease |
| 139 | *Legionella pneumophila* | Pontiac Fever |
| 140 | Pasteurellales | |
| 141 | Pasteurellaceae | |
| 142 | *Haemophilus* | |
| 143 | *Haemophilus ducreyi* | *Haemophilus ducreyi* Infection |
| 144 | *Haemophilus influenzae* serotype b | *Haemophilus influenzae* Serotype b (Hib) Infection |
| 145 | Pseudomonadales | |
| 146 | Pseudomonadaceae | |
| 147 | *Pseudomonas* | |
| 148 | *Pseudomonas aeruginosa* group | |
| 149 | *Pseudomonas aeruginosa* | *Pseudomonas aeruginosa* infection |
| 150 | Moraxellaceae | |
| 151 | *Acinobacter* | *Acinetobacter* Infection |
| 152 | Thiotrichales | |
| 153 | Francisellaceae | |
| 154 | *Francisella* | |
| 155 | *Francisella tularenis* | *Francisella tularensis* Infection |
| 156 | Vibrionales | |
| 157 | Vibrionaceae | |
| 158 | *Vibrio* | |
| 159 | *Vibrio parahaemolyticus* | *Vibrio parahaemolyticus* Infection |
| 160 | *Vibrio vulnificus* | *Vibrio vulnificus* Infection |
| 161 | *Vibrio cholerae* | Cholera |
| 162 | Spirochaetes | |
| 163 | Spirochaetes (class) | |
| 164 | Spirochaetales | |
| 165 | Leptospiraceae | |
| 166 | *Leptospira* | Leptospirosis |
| 167 | Spirochaetaceae | |
| 168 | *Borrelia* | |
| 169 | *Borrelia burgdorferi* Group | |
| 170 | *Borrelia burgdorferi* | Lyme Disease |
| 171 | *Treponema* | |
| 172 | *Treponema pallidum* | Syphilis |

More specifically, the present invention provides for an immunogenic composition and method of use where the immunogenic composition comprises a PIKA adjuvant together with a fungal antigen, wherein exemplary antigens include but are not limited to antigens of one or more of the fungi described in Table 3.

TABLE 3

Fungal pathogens and diseases

| | Fungal Taxonomy | Disease |
|---|---|---|
| 1 | Ascomycota (ascomycetes) | |
| 2 | Pezizomycotina | |
| 3 | Eurotiomycetes | |
| 4 | Eurotiales | |
| 5 | Trichocomaceae | |
| 6 | mitosporic Trichocomaceae | |
| 7 | *Aspergillus* | Aspergillosis |
| 8 | Onygenales | |
| 9 | Ajellomycetaceae | |
| 10 | *Ajellomyces* | |
| 11 | *Ajellomyces capsulatus* | |
| 12 | *Histoplasma capsulatum* | Histoplasmosis |
| 13 | *Blastomycoides dermatitidis* | Blastomycosis |
| 14 | Arthodermataceae | Ringworm |
| 15 | mitosporic Onygenales | |
| 16 | *Coccidiodes* | |
| 17 | *Coccidiodes immitis* | Coccidioidomycosis, Valley fever |
| 18 | *Paracoccidioides* | |
| 19 | *Paracoccidioides brasiliensis* | |

TABLE 3-continued

Fungal pathogens and diseases

| | Fungal Taxonomy | Disease |
|---|---|---|
| 20 | Sordariomycetes | |
| 21 | Sordariomycetidae | |
| 22 | Ophiostomatales | |
| 23 | Ophiostomataceae | |
| 24 | mitosporic Ophiostomataceae | |
| 25 | *Sporothrix schenckii* | Sporotrichosis |
| 26 | Pneumocystidomycetes | |
| 27 | Pneumocystidales | |
| 28 | Pneumocystidaceae | |
| 29 | Pneumocystis | |
| 30 | *Pneumocystis jiroveci* | PCP Infection |
| 31 | Saccharomycotina | |
| 32 | Saccharomycetes | |
| 33 | Saccharomycetales | |
| 34 | mitosporic Saccharomycetales | |
| 35 | Candida | |
| 36 | *Candida albicans* | Candidiasis, Thrush |
| 37 | *Basidiomycota (basidiomycetes)* | |
| 38 | Hymenomycetes | |
| 39 | Heterobasidiomycetes | |
| 40 | Tremellomycetidae | |
| 41 | Tremellales | |
| 42 | Tremellaceae | |
| 43 | Filobasidiella | |
| 44 | Filobasidiella neoformans | |
| 45 | *Cryptococcus neoformans* | Cryptococcosis |
| 46 | Metoza | |
| 47 | Eumetazoa | |
| 48 | Bilareria | |
| 49 | Acoelomata | |
| 50 | Platyhelminthes | |
| 51 | Trematoda | |
| 52 | Digenae | |
| 53 | Strigeidida | |
| 54 | Schistosomatidea | |
| 55 | *Schistosoma* | |
| 56 | *Schistosoma haematobium* | Schistosomiasis |
| 57 | *Schistosoma japonicum* | Schistosomiasis |
| 58 | *Schistosoma mansoni* | Schistosomiasis |
| 59 | Pseudocoelomata | |
| 60 | Nematoda | |
| 61 | Chromadorae | |
| 62 | Spirurida | |
| 63 | Filarioidea | |
| 64 | Onchocercidae | |
| 65 | *Brugia* | |
| 66 | *Brugia malayi* | Lymohatic filariasis |

More specifically, the present invention provides for an immunogenic composition and method of use, where the immunogenic composition comprises a PIKA adjuvant together with a parasitic antigen, wherein exemplary antigens include but are not limited to antigens of one or more of the parasites described in Table 4.

TABLE 4

Parasitic pathogens and diseases

| Parasite Taxonomy | Disease |
|---|---|
| Phylum Sarcomastigophora (the protozoa) | |
|   Subphylum Mastigophora (the flagellates) | |
|     Class Zoomastigophorea | |
|       Order Trichomonadida | |
|         *Dientamoeba fragilis* | *Dientamoeba fragilis* Infection |
|       Order Diplomonadida | |
|         *Giardia lamblia* (giardiasis) *Glardia intestinalis* | Giardiasis/*Giardia* Infection |
|       Order Kinetoplastida | |
|         *Leishmania* | Kala-Azar |
|         *Trypanosoma cruzi* | Chagas Disease |
|         *Trypanosoma brucei* | African Trypanosomiasis |
|   Subphylum Sarcodina (the amoebae) | |

TABLE 4-continued

Parasitic pathogens and diseases

| Parasite Taxonomy | Disease |
|---|---|
| Superclass Rhizopoda | |
|     Class Lobosea | |
|         Order Amoebida | |
|             *Entamoeba histolytica* | Amebiasis |
| Phylum Apicomplexa | |
|     Class Sporozoea | |
|         Subclass Coccidia | |
|             Order Eucoccidiorida | |
|                 Suborder Eimeriorina | |
|                       Family Eimeriina | |
|                           *Isospora belli* | *Isospora* Infection |
|                       Family Sarcocystidae | |
|                           *Toxoplasma gondii* (toxoplasmosis) | Toxoplasmosis |
|                       Family Cryptosporidiidae | |
|                           *Cryptosporidium parvum* (cryptosporidosis) | Cryptosporidiosis |
|                           *Cyclospora cayetanensis* | Cyclosporiasis |
|         Subclass Piroplasmasina | |
|             Family Babesiidae | |
|                 *Babesia* eg *Babesia microti* | *Babesia* Infection |
|                 and *Babesia divergens* | |
| Phylum Ciliophora (the ciliates) | |
|     Class Litostomatea | |
|         Order Vestibuliferida | |
|             *Balantidium coli* | *Balantidium* Infection |
| Phylum Plathyhelminthes (the flatworms) | |
|     Class Trematoda | |
|         Subclass Digenea (the digenetic trematodes) | |
|             Order Echinostomatiformes | |
|                 Family Fasciolidea | |
|                       *Fasciola hepatica* | Fascioliasis |
|                       *Fasciolopsis buski* | Fasciolopsiasis |
|             Order Strigeiformes | |
|                 Family Schistosomatidae | |
|                       *Schistosoma mansoni, S. haematobium,* | Schistosomiasis |
|                     and *S. japonicum* | |
|             Order Opisthorchiformes | |
|                 Family Opisthorchiidae | |
|                       *Clonorchis sinensis* | *Clonorchis* Infection |
|                 Family Heterophyidae | |
|                       *Heterophyes heterophyes* | *Heterophyes* Infection |
|             Order Plagiorchiformes | |
|                 Suborder Plagiorchiata | |
|                     Family Dicrocoeliidae | |
|                       *Platynostomum* sp. | Malaria |
|                 Suborder Troglotremata | |
|                     Family Troglotrematidae | |
|                       *Paragonimus* | Paragonimiasis |
|     Class Cestoidea | |
|         Subclass Eucestoda (the tapeworms) | |
|             Order Cyclophyllidea | |
|                     *Dipylidium caninum* | *Dipylidium* Infection |
|                     *Echinoccus multiloclaris* | Alveolar Hydatid Disease |
|                     *Hymenolepis nana* | Hymenolepiasis |
|                     *Taenia saginata* | Taeniasis, Cysticerosis |
|             Order Proteocephalata | |
|                 *Opisthorohis viverrini* | *Opisthorchis* Infection |
|             Order Pseudophyllidea | |
|                 *Diphyllobothrium latum* | *Diphyllobothrium* Infection |
| Phylum Nematoda (the roundworms) | |
|     Class Aphasmida (=Enoplea) | |
|         Order Trichurida | |
|             Family Capillaridae | |
|                 *Capillaria philippinensis* | *Capillaria* Infection |
|             Family Trichinellidae | |
|                 *Trichinella* | Trichinellosis/Trichinosis |
|             Family Trichuridae | |
|                 *Trichuris trichiura* | *Trichuriasis* |
|     Class Rhabditae | |
|         Order Rhabditidae | |
|             Strongyloides stercoralis | Strongyloidiasis |
|         Order Strongylida | |
|             Family Ancylostomidae | |
|                 *Ancylostoma duodenale* | Hookworm Infection |

TABLE 4-continued

| Parasitic pathogens and diseases | |
|---|---|
| Parasite Taxonomy | Disease |
|         *Angiostrongylus cantonensis* | Angiostrongyliasis |
|     Order Ascaridida | |
|         Ascaris | Ascaris Infection |
|         *Toxocara canis, T. cati* | Roundworm Infection, Intestinal |
|         *Baylisascaris* | *Baylisascaris* Infection |
|         *Anisakis simplex* and | Anisakiasis |
|         *Pseudoterranova decipiens* | |
|     Order Oxyurida | |
|         *Enterobius vermicularis* | Pinworm Infection |
|     Order Spirurida | |
|       Suborder Spirurina | |
|         Family Onchocercidae | |
|           *Onchocerca volvulus* (onchocerciasis, riverblindness) | Onchocerciasis |
|       Suborder Camallanina | |
|         Family Dracunculidae | |
|           *Dracunculus medinensis* | Guinea Worm Disease |
| Phylum Arthropoda | |
|   Subphylum Crustacea | |
|     Class Insecta | |
|       Order Anoplura | |
|         *Pediculus humanus capitis* | Pediculosis |
|   Subphylum Chelicerata | |
|     Class Arachnida | |
|       Order Acari | |
|         Suborder Astigmata | |
|           Sarcoptes scabiei | Scabies |

In a related embodiment, the present invention provides for an immunogenic composition and method of use, where the immunogenic composition comprises a PIMA adjuvant together with an allergy antigen ("allergen") or vaccine where the source of the antigen or vaccine is derived from or produced to emulate a pathogen from a human or animal allergy sources including; plants, animals, fungi, insects, food, drugs, dust, and mites and the like.

Allergens include but are not limited to environmental aeroallergens; plant pollens such as ragweed/hayfever; weed pollen allergens; grass pollen allergens; Johnson grass; tree pollen allergens; ryegrass; arachnid allergens, such as house dust mite allergens (e.g., Der p I, Der f I, etc.); storage mite allergens; Japanese cedar pollen/hay fever; mold spore allergens; animal allergens (e.g., dog, guinea pig, hamster, gerbil, rat, mouse, etc., allergens); food allergens (e.g., allergens of crustaceans; nuts, such as peanuts; citrus fruits); insect allergens; venoms: (Hymenoptera, yellow jacket, honey bee, wasp, hornet, fire ant); Other environmental insect allergens from cockroaches, fleas, mosquitoes, etc.; bacterial allergens such as streptococcal antigens; parasite allergens such as *Ascaris* antigen; viral antigens; fungal spores; drug allergens; antibiotics; penicillins and related compounds; other antibiotics; whole proteins such as hormones (insulin), enzymes (streptokinase); all drugs and their metabolites capable of acting as incomplete antigens or haptens; industrial chemicals and metabolites capable of acting as haptens and functioning as allergens (e.g., the acid anhydrides (such as trimellitic anhydride) and the isocyanates (such as toluene diisocyanate)); occupational allergens such as flour (e.g., allergens causing Baker's asthma), castor bean, coffee bean, and industrial chemicals described above; flea allergens; and human proteins in non-human animals.

Allergens include but are not limited to cells, cell extracts, proteins, polypeptides, peptides, polysaccharides, polysaccharide conjugates, peptide and non-peptide mimics of polysaccharides and other molecules, small molecules, lipids, glycolipids, and carbohydrates.

Examples of specific natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemiisfolia;* Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

In a related embodiment, the present invention provides for a polynucleotide adjuvant composition and method of use where the immunogenic composition comprises a PIKA adjuvant together with an autoimmune antigen or vaccine.

In a related embodiment, the present invention provides for an immunogenic composition and method of use, where the immunogenic composition comprises the PIKA adjuvant alone or together with a cancer antigen, wherein exemplary antigens include but are not limited to antigens of one or more of the cancers described in Table 5.

TABLE 5

Cancers
Cancer Taxonomy and Diseases

| | |
|---|---|
| 1 | Bone |
| 2 |   Ewing's Family of Tumors |
| 3 |   Osteosarcoma |
| 4 | Brain |
| 5 |   Brain Tumor |
| 6 |   Brain Stem Glioma |
| 7 |   Cerebellar Astrocytoma |
| 8 |   Cerebral Astrocytoma/Malignant Glioma |
| 9 |   Ependymoma |
| 10 |   Medulloblastoma |
| 11 |   Supratentorial Primitive Neuroectodermal Tumors and Pineoblastoma |
| 12 |   Visual Pathway and Hypothalamic Glioma |
| 13 | |
| 14 | Breast |
| 15 |   Breast Cancer |
| 16 | Digestive/Gastrointestinal |
| 17 |   Anal Cancer |
| 18 |   Bile Duct Cancer, Extrahepatic |
| 19 |   Carcinoid Tumor, Gastrointestinal |
| 20 |   Colon Cancer |
| 21 |   Esophageal Cancer |
| 22 |   Gallbladder Cancer |
| 23 |   Liver Cancer |
| 24 |   Pancreatic Cancer |
| 25 |   Rectal Cancer |
| 26 |   Small Intestine Cancer |
| 27 |   Stomach (Gastric) Cancer |
| 28 | Endocrine |
| 29 |   Adrenocortical Carcinoma |
| 30 |   Carcinoid Tumor, Gastrointestinal |
| 31 |   Islet Cell Carcinoma (Endocrine Pancreas) |
| 32 |   Parathyroid Cancer |
| 33 |   Pheochromocytoma |
| 34 |   Pituitary Tumor |
| 35 |   Thyroid Cancer |
| 36 | Eye |
| 37 |   Melanoma, Intraocular |
| 38 |   Retinoblastoma |
| 39 | Genitourinary |
| 40 |   Bladder Cancer |
| 41 |   Kidney (Renal Cell) Cancer |
| 42 |   Penile Cancer |
| 43 |   Prostate Cancer |
| 44 |   Renal Pelvis and Ureter Cancer, Transitional Cell |
| 45 |   Testicular Cancer |
| 46 |   Urethral Cancer |
| 47 |   Wilms' Tumor and Other Childhood Kidney Tumors |
| 48 | Germ Cell |
| 49 |   Extracranial Germ Cell Tumor |
| 50 |   Extragonadal Germ Cell Tumor |
| 51 |   Ovarian Germ Cell Tumor |
| 52 |   Testicular Cancer |
| 53 | Gynecologic |
| 54 |   Cervical Cancer |
| 55 |   Endometrial Cancer |
| 56 |   Gestational Trophoblastic Tumor |
| 57 |   Ovarian Epithelial Cancer |
| 58 |   Ovarian Germ Cell Tumor |
| 59 |   Ovarian Low Malignant Potential Tumor |
| 60 |   Uterine Sarcoma |
| 61 |   Vaginal Cancer |
| 62 |   Vulvar Cancer |
| 63 | |
| 64 | Head and Neck |
| 65 |   Hypopharyngeal Cancer |
| 66 |   Laryngeal Cancer |
| 67 |   Lip and Oral Cavity Cancer |
| 68 |   Metastatic Squamous Neck Cancer with Occult Primary |
| 69 |   Nasopharyngeal Cancer |
| 70 |   Oropharyngeal Cancer |
| 71 |   Paranasal Sinus and Nasal Cavity Cancer |
| 72 |   Parathyroid Cancer |
| 73 |   Salivary Gland Cancer |
| 74 | Hematologic/Blood |
| 75 |   Leukemia |
| 76 |   Acute Lymphoblastic Leukemia |
| 77 |   Acute Myeloid Leukemia |
| 78 |   Chronic Lymphocytic Leukemia |
| 79 |   Chronic Myelogenous Leukemia |
| 80 |   Hairy Cell Leukemia |
| 81 |   Lymphoma |
| 82 |   AIDS-Related Lymphoma |
| 83 |   Cutaneous T-Cell Lymphoma |
| 84 |   Hodgkin's Lymphoma |
| 85 |   Mycosis Fungoides |
| 86 |   Non-Hodgkin's Lymphoma |
| 87 |   Primary Central Nervous System Lymphoma |
| 88 |   Sezary Syndrome |
| 89 |   T-Cell Lymphoma, Cutaneous |
| 90 |   Waldenström's Macroglobulinemia |
| 91 | Other |
| 92 |   Chronic Myeloproliferative Disorders |
| 93 |   Multiple Myeloma/Plasma Cell Neoplasm |
| 94 |   Myelodysplastic Syndromes |
| 95 |   Myelodysplastic/Myeloproliferative Diseases |
| 96 | Lung |
| 97 |   Non-Small Cell Lung Cancer |
| 98 |   Small Cell Lung Cancer |
| 99 | Musculoskeletal |
| 100 |   Ewing's Family of Tumors |
| 101 |   Osteosarcoma/Malignant Fibrous Histiocytoma of Bone |
| 102 |   Rhabdomyosarcoma |
| 103 |   Soft Tissue Sarcoma |
| 104 |   Uterine Sarcoma |
| 105 | Neurologic |
| 106 |   Brain Tumor |
| 107 |   Brain Stem Glioma |
| 108 |   Cerebellar Astrocytoma |
| 109 |   Cerebral Astrocytoma/Malignant Glioma |
| 110 |   Ependymoma |
| 111 |   Medulloblastoma |
| 112 |   Supratentorial Primitive Neuroectodermal Tumors and Pineoblastoma |
| 113 |   Visual Pathway and Hypothalamic Glioma |
| 114 |   Neuroblastoma |
| 115 |   Pituitary Tumor |
| 116 |   Primary Central Nervous System Lymphoma |
| 117 | Respiratory/Thoracic |
| 118 |   Lung Cancer, Non-Small Cell |
| 119 |   Lung Cancer, Small Cell |
| 120 |   Malignant Mesothelioma |
| 121 |   Thymoma and Thymic Carcinoma |
| 122 | Skin |
| 123 |   Cutaneous T-Cell Lymphoma |
| 124 |   Kaposi's Sarcoma |
| 125 |   Melanoma |
| 126 |   Merkel Cell Carcinoma |
| 127 |   Skin Cancer |

In a related embodiment the source of the cancer antigen may be: 1) Viral proteins—for example hepatitis B virus (HBV), Epstein-Barr virus (EBV) and human papillomavirus (HPV)—are important in the development of hepatocellular carcinoma, lymphoma, and cervical cancer, respectively; 2). whole cancer cells that may be inactivated and/or nonpurified and/or semi-purified extract of these cells; 3). tumor-associated antigens (TAAs) such as the tumor specific oncogenic proteins, glycosylated proteins, gangliosides, glycolipide, mucins, peptide, carbohydrates and anti-idiotype monoclonal antibodies.

In a related embodiment, the use of the immunogenic composition comprising the polynucleotide adjuvant may be for the treatment of cancer tumors through the prevention of further growth of existing cancers, the prevention of the recurrence of treated cancers, or the elimination of cancer cells not killed by prior treatments. The treatment may be administered prior to, in conjunction with, or post other therapies provided to the individual and thus may form part of an overall combination therapy to treat the cancer.

In a related embodiment the cancer vaccine provides for therapies capable of inducing tumor specific immune responses against both a primary tumor and metastases. In addition, the induction of a strong immunity may lead to the establishment of immune memory, thereby reducing or inhibiting tumor recurrence. The cancer vaccine may induce specific antibodies against tumor-associated surface antigens and preferably to induce cellular immune response with preferably a bias toward a Th1 immune response.

Any of a variety of known tumor-specific antigens or tumor-associated antigens (TAA) can be included in a subject immunogenic composition. The entire TAA may be, but need not be, used. Instead, a portion of a TAA, e.g., an epitope, may be used. Tumor-associated antigens (or epitope-containing fragments thereof) which may be used into YFV include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, and p21ras. A synthetic analog of any TAA (or epitope thereof), including any of the foregoing, may be used. Furthermore, combinations of one or more TAAs (or epitopes thereof) may be included in the composition.

In some embodiments, a subject immunogenic composition comprises a polynucleotide adjuvant, and at least two different antigens, e.g., in some embodiments, a subject immunogenic composition comprises two antigens, three antigens, four antigens, five antigens, or more than five antigens.

Additional Agents

In some embodiments, a subject immunogenic composition comprises, in addition to a PIKA adjuvant and an antigen, one or more additional agents, e.g., immunomodulatory agents, carriers, and the like.

In an embodiment of particular interest, the present invention provides for an immunogenic composition and method of use, where the immunogenic composition comprises the PIKA adjuvant, an antigen or vaccine together with another immunomodulating substance, including adjuvants, where suitable immunomodulating substances include, but are not limited to: an aluminum composition such as aluminum hydroxide; oil-in-water emulsions compositions or emulsions comprising an immunogenic substances, including Complete Freund's Adjuvant; an oil-in-water emulsion containing dried, heat-killed *Mycobacterium tuberculosis* organisms; Incomplete Freund's Adjuvant; emulsions including mycobacterial cell wall components; emulsions including squalene (MF-59); detoxified endotoxins, lipid A derivatives including monophosphoryl lipid A-microbial (MPL); haptens; nitrocellulose-absorbed protein; saponins including particulate immunomodulators isolated from the bark of Quillaja Saponoria for example QS21; endogenous human immunomodulators; bacterial derived adjuvants including unmethylated CpG dinucleotides; oligodeoxynucleotides (e.g., synthetic oligonucleotides) containing unmethylated CpG dinucleotides; liposomes (e.g., liposomes made of biodegradable materials such as phospholipids); biodegradable polymer microspheres (e.g., microspheres made from a variety of polymers such as polylactic-co-glycolic acid (PLGA), polyphosphazene and polyanhydrides); Interlukin-2; *Bacillus* Calmette Guerin; Granulocyte Monocyte-Colony Stimulating Factor; Montanide ISA-51; Keyhole limpet hemocyanin; DNA; proteins; encapsulated antigens; immune stimulating complexes (ISCOM's); cholera toxin, choleral toxin derivatives; zonula occludens toxin; *escherichia coli* heat-labile enterotoxin; labile toxin, labile toxin derivatives; pertussis toxin, pertussis toxin derivatives; muramyl dipeptide derivatives; seppic series of montanide adjuvants; poly-di(carboxylatophenoky)phosphazene and *leishmania* elongation factor.

When the subject immunogenic composition is administered in conjunction with another adjuvant, the polynucleotide adjuvant can be administered before and/or after, and/or simultaneously with the other adjuvant. For example the polynucleotide adjuvant may be administered with the initial administration of the antigen, followed by a boost dose of vaccine comprising either or both of the adjuvants. Alternatively the initial dose of vaccine administered may exclude the polynucleotide adjuvants but an immunogenic substance comprising the polynucleotide adjuvant is subsequently administered to the patient.

In certain embodiments the subject immunogenic composition may be administered with cytokines or other co-stimulatory molecules for example: IL-1, IL-2, IL-4, IL-5, IL-6, IL-7, IL-10, IL-12, IL-15

In a related embodiment the present invention provides for an immunogenic substance comprising a PIKA adjuvant, an antigenic substance or substances, plus a suitable carrier. The carrier may be for example an oil-and-water emulsion, suspension, a lipid vehicle, aluminum salt, cochleates, ISCOMs, liposomes, live bacterial vectors, live viral vectors, microspheres, nucleic acid vaccines, polymers, polymer rings, sodium fluoride, transgenic plants, virosomes, virus like particles, and other delivery vehicles known in the art.

The polynucleotide adjuvant may be directly administered to the subject or may be administered in conjunction with a delivery complex. Where the delivery complex is a substance associated with a targeting means e.g. a molecule that results in higher affinity binding to target cell such as dendritic cell surfaces and/or increased cellular uptake by target cells. Examples of delivery complexes include but are not limited to; nucleic acid delivery acids associated with: a sterol (e.g. cholesterol), a lipid (e.g. cationic lipid, virosome or liposome), or a target cell specific binding agent (e.g. a ligand recognized by a target cell specific receptor). Preferred complexes may be sufficiently stable in vivo to prevent significant uncoupling prior to internalization by the target cell. However, the complex may be cleavable under appropriate conditions within the cell.

In one embodiment of interest, the composition comprising PIKA adjuvant does not include poly-L-lysine or a derivative thereof.

Kits

In certain embodiments, the invention provides a kit comprising a subject immunogenic composition. In certain embodiments, the invention provides a kit comprising a PIKA adjuvant and an antigen in separate formulations.

In a related embodiment, the invention provides for a kit comprising the polynucleotide adjuvant and an immunogenic compound where the immunogenic substance is an antigen.

In some embodiments, a subject kit comprises a subject immunogenic composition in a sterile liquid (e.g., aqueous) formulation, where the formulation is sterile, and is provided in a sterile container, a sterile vial, or a sterile syringe.

In some embodiments, a subject kit comprises a subject immunogenic composition formulated for injection. In some embodiments, a subject kit comprises a subject immunogenic composition in a sterile liquid formulation, contained within a sterile syringe; and a needle. In some embodiments, a subject kit comprises a subject immunogenic composition in a sterile liquid formulation in a unit dosage amount (e.g., a single dose), contained within a sterile syringe; and a needle.

In some embodiments, a subject kit comprises a subject immunogenic composition, lyophilized and in a sterile container; and a container comprising a sterile liquid for reconstitution of the lyophilized composition. In some embodiments, the kit further comprises instructions for reconstitution of the lyophilized composition.

In some embodiments a subject kit comprises an immunogenic composition formulated for administration rectally, vaginally, nasally, orally (including inhalation), opthamalically, topically, pulmonary, ocularly or transdermally and an appropriate delivery device for example, inhaler, suppository, applicator or the like, A subject kit in some embodiments will further include instructions for use, including e.g., dosage amounts and dosage frequencies. Instructions are in some embodiments printed directly on the kit. In other embodiments, instructions are printed material provided as a package insert. Instructions can also be provided in other media, e.g., electronically in digital or analog form, e.g., on an audio cassette, an audio tape, a compact disc, a digital versatile disk, and the like.

Formulations

A subject immunogenic composition is provided in any of a variety of formulations. For example, a subject immunogenic composition may be prepared as an injectable, dry power, liquid solution, for example: aqueous or saline solution or as: a suspension, cream, emulsion, tablet, coated tablet, microcapsule, suppository, drops, pill, granules, dragee, capsule, gel, syrup or slurry. The preparation of formulations of a desired immunogenic composition is generally described in Vaccine $4^{th}$ Edition by Stanley A Plotkin et al., W.B. Saunders Company; 4th edition 2003. Suitable formulations are also described in, e.g., A. Gennaro (2000) "Remington: The Science and Practice of Pharmacy," $20^{th}$ edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.; Methods in Molecular Medicine, Vol. 87: Vaccine Protocols, 2nd edition (2003), Humana Press; Mucosal Vaccines (1996), Kiyono et al., eds., Academic Press; and Vaccine Adjuvants: Preparation Methods and Research Protocols (2000) D. T. O'Hagan, Humana Press.

A subject immunogenic composition may be microencapsulated, encochleated, coated onto microscopic gold particles, contained in liposomes, nebulized aerosols, pellets for implantation into the skin, or dried onto a sharp object (e.g., a needle) to be scratched into the skin.

In a further embodiment the subject immunogenic substance may be delivered alone or in conjunction with a dispersion system. In some embodiments the dispersion system is selected from the group consisting of for example: macromolecular complexes, nanocapsules, microspheres, beads and lipid based systems. Lipid based systems optionally include oil-in-water emulsions, micelles, mixed micelles or liposomes.

In certain embodiments a subject immunogenic composition comprising the PIKA adjuvant is in the form of a pharmaceutically acceptable solution, which may routinely contain pharmaceutically acceptable concentrations of salt, buffering agents, preservatives, compatible carriers, adjuvants and optionally other therapeutic ingredients. The composition may contain additives for example: disintegrants, binders, coating agents, swelling agents, lubricants, flavorings, sweeteners or solubilizers and the like.

In certain embodiments a subject immunogenic composition comprising the PIKA adjuvant is administered in its neat for or in the form of a pharmaceutically acceptable salt.

The immunogenic composition of the present invention may be employed in such forms, both sterile and non-sterile, such as capsules, liquid solutions, liquid drops, emulsions, suspensions, elixirs, creams, suppositories, gels, soft capsules, sprays, inhalants, aerosols, powders, tablets, coated tablets, lozenges, microcapsules, suppositories, dragees, syrups, slurries, granules, enemas or pills. Any inert carrier can be used, such as saline, or phosphate buffered saline, stabilizers, propellants, encased in gelatin capsule or in a microcapsule or vector that aids administration or any such carrier in which the compounds used in the method of the present invention have suitable solubility properties for use in the methods of the present invention.

In certain embodiments, the PIKA adjuvant composition and an immunogenic composition comprising the PIKA adjuvant and antigenic compound is freeze-dried (lyophilized) for long term stability and storage in a solid form. The freeze-dried method is known to those skilled in the art.

In one aspect of particular interest, the invention provides for an adjuvant composition or immunogenic composition wherein the immunogenic composition, or the adjuvant composition contained in the immunogenic composition, is in a solid or liquid form or in solution or in suspension or in emulsion.

A subject immunogenic composition may be administered to an individual by means of a pharmaceutical delivery system for the inhalation route (oral, intratracheal, intranasal). Thus, a subject immunogenic composition may be formulated in a form suitable for administration by inhalation. The pharmaceutical delivery system is one that is suitable for respiratory therapy by topical administration of a subject bacterial composition to mucosal linings of the bronchi. This invention can utilize a system that depends on the power of a compressed gas to expel the bacteria from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the immunogenic composition, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a subject. Various types of propellants known to one of skill in the art can be utilized. Examples of suitable propellants include, but are not limited to, hydrocarbons or other suitable gas. In the case of the pressurized aerosol, the dosage unit may be determined by providing a value to deliver a metered amount.

There are several different types of inhalation methodologies which can be employed in connection with the present invention. A subject immunogenic composition can be formulated in basically three different types of formulations for inhalation. First, a subject immunogenic composition can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the subject as discussed within U.S. Pat. Nos. 5,404,871 and 5,542,410.

Alternatively, a subject immunogenic composition can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

Furthermore, a subject immunogenic composition can be formulated into dry powder formulations. Such formulations can be administered by simply inhaling the dry powder formulation after creating an aerosol mist of the powder. Technology for carrying such out is described within U.S. Pat. No. 5,775,320 and U.S. Pat. No. 5,740,794. Formulations suitable for intranasal administration include nasal sprays, nasal drops, aerosol formulations; and the like.

In some embodiments, a subject immunogenic composition is formulated as a sustained release (e.g. a controlled release formulation). For example, in some embodiments, a subject immunogenic composition is formulated into pellets or cylinders and implanted intramuscularly or subcutaneously as depot injections or as implants. Such implants will generally employ known inert materials such as biodegradable polymers. Injectable depot forms are made by forming microencapsule matrices of a subject immunogenic composition in biodegradable polymers such as polylactide-polyglycolide. Examples of other suitable biodegradable polymers include poly(orthoesters) and poly(anhydrides). Depot injectable formulations are also prepared by entrapping the composition in liposomes or microemulsions which are compatible with body tissue. Delivery release systems also include the following examples: polymer based systems, microcapsules, lipids, hydrogel release systems, sylastic systems, peptide systems, peptide based systems, wax coatings, compressed tablets, partially fused implants, Other forms of sustained release are known by those skilled in the art.

Methods

In one aspect of particular interest, the invention provides for a method for eliciting and/or enhancing immune responses to an antigenic compound, comprising administering to a host a subject immunogenic composition. In some embodiments, the host is a human. In other embodiments, the host is a non-human animal, e.g., a non-human mammal, an avian species, etc.

In certain embodiments, the polynucleotide adjuvant composition can be used in the context of a vaccine. Optionally, the vaccine composition contains additional adjuvants. Vaccines classes included are anti-infectious diseases, anti cancer, anti-allergy and anti-autoimmune diseases.

Furthermore, the present invention provides a method for enhancing immune responses to an antigenic compound by administering to a host a subject immunogenic composition. The host can be a human being or non-human animal.

In certain embodiments the adjuvant is administered together with the antigen. The further embodiments the adjuvant is administered prior to or post the administration of the antigen.

A subject immunogenic composition is in some embodiments delivered parenterally by injection, such as intramuscular, intraperitoneal, intravenous, subcutaneous or intradermal injection. In other embodiments the immunogenic composition is administered intradermally in ways other than by injection for example, without breaching the epithelial barrier by mechanical means. In other embodiments, the immunogenic composition is delivered rectally, vaginally, nasally, orally (including inhalation), opthamalically, ocularly, topically, pulmonary or transdermally.

The subject may be exposed to the antigen through environmental contact and therefore at risk of developing for example, an allergic reaction, an infectious disease, autoimmune disease or a cancer. In other embodiments the subject has for example an infectious disease, autoimmune disease, a cancer or allergy as a result of prior exposure to an antigen through environmental contact.

In certain embodiments, when the mode of administration of the immunogenic composition comprising a polynucleotide adjuvant is for the treatment of cancer tumors, the delivery is by injection directly into the tumor, or adjacent to the tumor. In some embodiments, the immunogenic composition is delivered evenly over or throughout the tumor to enhance the biodistribution and hence enhance the therapeutic benefit.

For parenteral administration in an aqueous solution, for example, the solution should be suitably buffered if necessary and the liquid diluent first rendered isotonic with sufficient saline or glucose. These particular aqueous solutions are especially suitable for intravenous and intraperitoneal administration. In this connection, sterile aqueous media which can be employed will be known to those of skill in the art in light of the present disclosure. Exemplary injection media which can be used in the present invention include a buffer with or without dispersing agents and/or preservatives, and edible oil, mineral oil, cod liver oil, squalene, mono-, di- or triglyceride, and a mixture thereof.

A subject immunogenic composition is administered in an "effective amount" that is, an amount of a subject immunogenic composition that is effective in a selected route of administration to elicit, induce, or enhance an immune response. In some embodiments, an immune response is elicited to antigens produced by a pathogenic microorganism. In some embodiments, the amount of a subject immunogenic composition is effective to limit an infection, and/or to eradicate an infection, and/or to reduce a symptom associated with infection, by a pathogenic organism.

For example, in some embodiments, administration of a subject immunogenic composition to an individual is effective to treat an infectious disease, where treating an infectious disease, encompasses one or more of reducing the number of pathogenic agents in the individual (e.g., reducing viral load, reducing bacterial load, reducing the number of protozoa, reducing the number of helminths) and/or reducing a parameter associated with the infectious disease, including, but not limited to, reduction of a level of a product produced by the infectious agent (e.g., a toxin, an antigen, and the like); and reducing an undesired physiological response to the infectious agent (e.g., fever, tissue edema, and the like).

The exact amount of such compositions required will vary from subject to subject, depending on the species, age, weight, and general conditions of the subject, the severity of the disease, infection, or condition that is being treated or prevented, the particular compound used, its mode administration, and the like. An appropriate amount may be determined by one of ordinary skill in the art using only routine experimentation given the teachings herein. Following an initial administration, subjects may receive one or several booster immunizations adequately spaced.

In some embodiments, serial doses of a subject immunogenic composition are administered. In these embodiments, the first dose of a subject immunogenic composition may be as a result of administering a vaccine. The second dose of a subject immunogenic composition is administered to the individual after the individual has been immunologically primed by exposure to the first dose. The booster may be administered days, weeks or months after the initial immunization, depending upon the patient's response and condition. For example, the booster dose is administered from about 2 days to about 12 months after the initial dose, e.g., from about 2 days to about 7 days, from about 1 week to about 2 weeks, from about 2 weeks to about 4 weeks, from about 4 weeks to about 8 weeks, from about 8 weeks to about 6 months, or from about 6 months to about 12 months after the initial dose. The present invention further contemplates the use of a third, fourth, fifth, sixth or subsequent booster immunization, using, e.g., a third, fourth, fifth, sixth, or subsequent dose.

In certain embodiments the means of administration may comprise a combination of alternative routes, for example: systemically administered dose (e.g. peritoneal, intra-muscular, subcutaneous or intradermal administration) may be followed by mucosally delivered dose (e.g. intranasal, inhalation) or vice versa.

In certain embodiments the polynucleotide adjuvant may be administered with either the first dose of antigen administered or any of the subsequent doses administered or all doses administered to the patient. At least one of the doses administered as part of the overall protocol would comprise the PIKA adjuvant.

In certain embodiments the composition of the administered immunogenic composition may vary between the original administration and the boost and/or between booster doses. By way of an example the original dose administered may comprise a DNA vaccine while the booster dose is in the form of a recombinant protein vaccine. At least one of the doses administered as part of the overall protocol would comprise the PIKA adjuvant.

Whether an antibody response to an antigen has been induced or enhanced in an individual is readily determined using standard assays. For example, immunological assays such as enzyme-linked immunosorbent assays (ELISA), radioimmunoassay (RIA), immunoprecipitation assays, and protein blot ("Western" blot) assays; and neutralization assays (e.g., neutralization of viral infectivity in an in vitro or in vivo assay); can be used to detect the presence of antibody specific for a microbial antigen in a bodily fluid or other biological sample, e.g., the serum, secretion, or other fluid, of an individual.

Whether a CD4 immune response to an antigen has been induced in an individual is readily determined using standard assays, e.g., fluorescence-activated cell sorting (FACS) (see, e.g., Waldrop et al. (1997) *J. Clin. Invest.* 99:1739-1750); intracellular cytokine assays that detect production of cytokines following antigen stimulation (see, e.g., Suni et al. (1998) *J. Immunol. Methods* 212:89-98; Nomura et al. (2000) *Cytometry* 40:60-68; Ghanekar et al. (2001) *Clin. Diagnostic Lab. Immunol.* 8:628-631); MHC-peptide multimer staining assays, e.g., use of detectably labeled (e.g., fluorescently labeled) soluble MHC Class II/peptide multimers (see, e.g., Bill and Kotzin (2002) *Arthritis Res.* 4:261-265; Altman et al. (1996) *Science* 274:94-96; and Murali-Krishna et al. (1998) *Immunity* 8:177-187); enzyme-linked immunospot (ELISPOT) assays (see, e.g., Hutchings et al. (1989) *J. Immunol. Methods* 120:1-8; and Czerkinsky et al. (1983) *J. Immunol. Methods* 65:109-121); and the like. As one non-limiting example of an intracellular cytokine assay, whole blood is stimulated with antigen and co-stimulating antibodies (e.g., anti-CD28, anti-CD49d) for 2 hours or more; Brefeldin A is added to inhibit cytokine secretion; and the cells are processed for FACS analysis, using fluorescently labeled antibodies to CD4 and to cytokines such as TNF-a, IFN-γ and IL-2.

Whether an antigen-specific CD8 (e.g., cytotoxic T cell; "CTL") response is induced to an antigen (e.g., to a pathogen) can be determined using any of a number of assays known in the art, including, but not limited to, measuring specific lysis by CTL of target cells expressing the antigen on their surface, which target cells have incorporated a detectable label which is released from target cells upon lysis, and can be measured, using, e.g., a $^{51}$Cr-release assay; a lanthanide fluorescence-based cytolysis assay; and the like.

Subjects Suitable for Treatment

Subjects suitable for treatment with a subject method of inducing an immune response to a microbial pathogen, and methods of treating or preventing an infection with a microbial pathogen, include individuals who have been infected with a pathogenic microorganism; individuals who are susceptible to infection by a pathogenic microorganism, but who have not yet been infected; and individuals who are at risk of becoming infected with a pathogenic microorganism, but who have not yet been infected. Suitable subjects include infants, children, adolescents, and adults.

Subjects suitable for treatment with a subject method of inducing an immune response to a microbial pathogen, and methods of treating or limiting an infection with a microbial pathogen, include pediatric target population, e.g., individuals between about 1 year of age and about 17 years of age, including infants (e.g., from about 1 month old to about 1 year old); children (e.g., from about 1 year old to about 12 years old); and adolescents (e.g., from about 13 years old to about 17 years old).

Subjects suitable for treatment with a subject method of inducing an immune response to a microbial pathogen, and methods of treating or limiting an infection with a microbial pathogen, include neonates, e.g., an individual (e.g., a human neonate) from one day to about 14 days old, e.g., from about 1 day to about 2 days old, from about two days to about 10 days old, or from about 10 days to about 14 days old.

In a particular embodiment, the subject is a human child about ten years or younger, e.g., about five years old or younger, and the immunogenic compositions are administered at any one or more of the following times: two weeks, one month, 2 months, 3 months, 4 months, 5 months, 6 months, 7 months, 8 months, 9 months, 10 months, 11 months, 12 months, 15 months, 18 months, or 21 months after birth, or at 2 years, 3 years, 4 years, 5 years, 6 years, 7 years, 8 years, 9 years, or 10 years of age. In some embodiments, a subject immunogenic composition is administered to an individual in the age range of from about 6 months to about 6 years, where the individual receives a first dose at about 6 months of age, and subsequent booster doses, e.g., 2-3 subsequent booster doses, at, e.g., 2 years of age, 4 years of age, and 6 years of age.

In a particular embodiment, the subject is a human adult from about 17 years old to 49 years old. In some embodiments, the subject is an elderly human adult from 50 to 65 years old, 65 to 75 years old, 75 to 85 years old or over 85 years old.

In some embodiments, a subject immunogenic composition is administered to an individual shortly after contact (e.g., shortly after confirmed or suspected contact) with an actual or potential source of the microbial pathogen, for example, an individual who is known to have or suspected to have an infection with a microbial pathogen. For example, in some embodiments, a subject immunogenic composition is administered to an individual within about 1 hour, within about 2 hours, within about 5 hours, within about 8 hours, within about 12 hours, within about 18 hours, within about 24 hours, within about 2 days, within about 4 days, within about 7 days, within about 2 weeks, or within about one month after contact with an individual who is known to have or suspected to have an infection with a microbial pathogen.

In some embodiments, a subject immunogenic composition is administered to an individual that is known or may be suspected of being a carrier or a microbial pathogen whether or not they are showing symptoms of the infection.

Subjects suitable for treatment with a subject method of inducing an immune response to a microbial pathogen, and methods of treating or limiting an infection with a microbial pathogen, include CD4+ T cell-deficient individuals ("CD4+-deficient" individuals), e.g., individuals who have lower than normal numbers of functional CD4+ T lymphocytes. As used herein, the term "normal individual" refers to an individual having CD4+ T lymphocyte levels and function(s) within the normal range in the population, for humans, typically 600 to 1500 CD4+ T lymphocytes per mm$^3$ blood. CD4+-deficient individuals include individuals who have an acquired immunodeficiency, or a primary immunodeficiency. An acquired immunodeficiency may be a temporary CD4+ deficiency, such as one caused by radiation therapy, or chemotherapy.

Also suitable for treatment with the methods of the invention are individuals with healthy, intact immune systems, but who are at risk for becoming CD4+ deficient ("at-risk" individuals). At-risk individuals include, but are not limited to, individuals who have a greater likelihood than the general population of becoming CD4+ deficient. Individuals at risk for becoming CD4+ deficient include, but are not limited to, individuals at risk for HIV infection due to sexual activity with HIV-infected individuals; intravenous drug users; individuals who may have been exposed to HIV-infected blood, blood products, or other HIV-contaminated body fluids; a baby who has passed through the birth canal of an HIV-infected individual; babies who are being nursed by HIV-infected mothers; and the like.

Subjects suitable for treatment with a subject method for treating cancer include individuals who have been infected with a carcinogenic substance, individuals who are susceptible to cancer but who have not yet been diagnosed with cancer; and individuals who are at risk of contracting cancer, but who have not yet been diagnosed with cancer. Suitable subjects include infants, children, adolescents, and adults.

Subjects suitable for treatment with a subject method for treating cancer include individuals who have been diagnosed with cancer; individuals who were previously treated for cancer, e.g., by chemotherapy or radiotherapy, and who are being monitored for recurrence of the cancer for which they were previously treated; and individuals who have undergone bone marrow transplantation or any other organ transplantation.

Subjects suitable for treatment with the formulations and methods of the instant invention for treating allergy include any individual who has been diagnosed as having an allergy. Subjects amenable to treatment using the methods and agents described herein include individuals who are known to have allergic hypersensitivity to one or more allergens. Subjects amenable to treatment include those who have any of the above-mentioned allergic disorders. Also amenable to treatment are subjects that are at risk of having an allergic reaction to one or more allergens. Also suitable are individuals who failed treatment with one or more standard therapies for treating an allergic disorder.

Subjects suitable for treatment include individuals living in industrialized nations; individuals living developing countries; individuals living in rural areas; individuals living in relatively isolated areas; and the like.

The target population for a subject immunogenic composition will vary, depending on the microbial pathogen The above disclosure generally describes the present invention. The following examples will be of assistance to the understanding of the present invention. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

PIKA in Combination with a Variety of Antigens Induces a Specific Immune Response This example involves use of PIKA in combination with a variety of antigens to elicit a specific immune response in vivo. The research was conducted in a series of independent experiments with a common protocol though using a different antigen each time. The antigens tested include: a recombinant protein hepatitis B surface antigen type adw, an inactivated split influenza vaccine (VAXIGRIP from Sanofi Pasteur), a synthesized HIV peptide antigen, a recombinant protein herpes simplex virus type 2 gD antigen, recombinant protective anthrax protein antigen, inactivated whole virus avian influenza antigen strain H5N1 and an inactivated whole virus Severe Acute Respiratory Syndrome (SARS) inactivated antigen.

The protocol for the individual experiment involves the inoculation of groups of Balb/c mice, three mice per group, with compositions of antigen alone, antigen with the PIKA adjuvant (a heterogeneous composition of PIKA molecules predominantly within a weight range distribution of about 66 kDa to 1,200 kDa), PIKA alone, a control comprising phosphate buffer solution (PBS).

Actual dosage quantities are provided for each antigen used. The mice were then given an identical booster vaccine ten to fourteen days after the initial injection. Ten to fourteen days after the booster injection a blood sample was taken, the mice were then sacrificed and tissue samples taken from the spleen. The results presented are the average of the test results of the individual mice within each group.

A suspension of spleen cells was prepared and a sample of the cell suspension from each mouse was put into 6-12 wells of the ELISPOT plate and cultured, Each well of the ELISPOT plate contained 200 ul of splenocyte suspension, approximately $2 \times 10^5$ to $1 \times 10^6$ cells/well (see details in tables below). For each mouse's sample of cultured splenocytes, half of wells containing the splenocytes were incubated with culture medium and the other half of wells were stimulated using the one of two different concentrations of particular antigen under evaluation. Plates are incubated at 37° C. for 20 hours in environmentally controlled conditions prior to final preparation and reading using a standard ELISPOT plate reader.

Standard ELISPOT tests, known to those skilled in the art, were used to detect the number of cells producing the cytokines IL-4, IL-2 and INF-γ.

Flow Cytometry analysis was used to detect INF-γ produced by CD4+ T cells. The use of Fluorescence-Activated Cell Sorter (FACS) is well known by those skilled in the art. In brief solutions of splenocytes at a concentration of $2.5 \times 10^6$ cells/ml were prepared and divided into individual tubes with 2 ml per sample. Samples stimulated with antigen were then prepared and after incubation at 37 C in environmentally controlled conditions for 5 hours. The samples then were washed and stained prior to reading in a standard FACS reader.

Standard ELISA tests known to those skilled in the art were use to detect the titer of specific antibodies in blood serum taken from the animal prior to sacrifice.

Example 1.1

Recombinant Hepatitis B Surface Antigen (HBSAg) adw

The results in table 6 below are the results of the ELISPOT test detecting the presence number of cells producing INF-γ, IL-2 and IL-4 using a recombinant protein hepatitis B surface antigen (HBsAg) type adw. The data in the table 6 (see also FIGS. 1, 2 and 3) represent the ELISPOT reading, the number of spot forming cells, that is, a direct measure the number of cells producing cytokine.

The distinct increase in the number of spot forming cells with the addition of the PIKA adjuvant (as compared with the antigen alone) demonstrates that the addition of the PIKA adjuvant to recombinant hepatitis B surface antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 6

ELISPOT detection of murine splenocytes producing cytokines after immunization with vaccines comprising PIKA and/or HBsAg adw

| | Groups of Mice | | | |
|---|---|---|---|---|
| | Group 1 HBsAg 4 ug + PIKA 50 ug | Group 2 HBsAg 4 ug | Group 3 PIKA 100 ug | Group 4 PBS |
| No. of cells producing IFN-γ/1 × 10$^6$ splenocytes | 539 | 26 | — | 2 |
| No. of cells producing IL-2/ 1 × 10$^6$ splenocytes | 347 | 60 | 3 | 10 |
| No. of cells producing IL-4/ 1 × 10$^6$ splenocytes | 210 | 82 | — | 1 |

Stimulation with HBsAg 2.0 ug/ml Unit: Splenocyte spot forming cells

Results of the ELISA test on the blood sample taken prior to sacrifice (Table 7 below and FIG. 4) demonstrate that the presence of PIKA significantly enhances the immune response and measured by the titer of specific antibodies detected in the serum.

TABLE 7

ELISA detection of specific IgG titers from murine serum after immunization with vaccines comprising PIKA and/or HBsAg adw

| | Groups of Mice | | | |
|---|---|---|---|---|
| | Group 1 HBsAg 4 ug + PIKA 50 ug | Group 2 HBsAg 4 ug | Group 3 PIKA 100 ug | Group 4 PBS |
| Optical density absorbance 405 nm at 400× dilution | 2.057 | 0.323 | 0.084 | 0.08 |

The conclusion drawn is that the addition of the PIKA adjuvant enhances the overall immune response to HBsAg, in particular the specific immune response, more particularly the adaptive immunity and more specifically predominant Th1 bias immune response and promote the cell mediated immune response.

Example 1.2

VAXIGRIP (Sanofi Pasteur), Inactivated and Purified Influenza Antigen Comprising; H1N1, H3N2 like Strains and b/Shanghai5/361/2002 Strain The results in table 8 below are the results of the ELISPOT test detecting the presence the number of cells producing INF-γ, IL-2 and IL-4 using VAXIGRIP vaccine a inactivated split human influenza vaccine produced by Sanofi Pasteur. The data in the table 8 (see also FIGS. 5, 6 and 7) represent the ELISPOT reading, the number of spot forming cells, that is, a direct measure of cytokine production.

The distinct increase in the number of spot forming cells with the addition of the PIKA adjuvant (as compared with the antigen alone) demonstrates that the addition of the PIKA adjuvant to the influenza antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 8

ELISPOT detection of murine splenocytes producing cytokines after immunization with vaccines comprising PIKA and/or inactivated split influenza antigen

| | | Groups of mice | | | | |
|---|---|---|---|---|---|---|
| | | Group 1 Flu 4.5 ug | Group 2 Flu 4.5 ug + PIKA 50 ug | Group 3 Flu 4.5 ug + PIKA 100 ug | Group 4 PIKA 100 ug | Group 5 PBS |
| No. of cells producing IFN-γ per 2.5 × 10$^5$ splenocytes | Not stimulated | 1 | — | 2 | 1 | — |
| | Stimulated with flu | 81 | 148 | 252 | 14 | 6 |
| No. of cells producing IL-2 per 2.5 × 10$^5$ splenocytes | Not stimulated | — | 1 | — | 1 | — |
| | Stimulated with flu | 23 | 85 | 122 | 1 | 1 |
| No. of cells producing IL-4 per 2.5 × 10$^5$ splenocytes | Not stimulated | 5 | 10 | 6 | 4 | 6 |
| | Stimulated with flu | 25 | 38 | 51 | 9 | 9 |

Unit: Splenocyte spot forming cells

Results of the ELISA test on the blood sample taken prior to sacrifice (Table 9 below and FIG. 8) demonstrate that the presence of PIKA significantly enhances the immune response and measured by the titer of specific antibodies detected in the serum.

antigen alone) demonstrates that the addition of the PIKA adjuvant to the HIV antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 10

ELISPOT detection of murine splenocytes producing cytokines after immunization with vaccines comprising PIKA and/or HIV gp 120 antigen

| | | Groups of mice | | | |
|---|---|---|---|---|---|
| | | Group 1 HIVgp 120 3 ug + PIKA 100 ug | Group 2 HIVgp 120 3 ug | Group 3 PIKA 100 ug | Group 4 NS |
| No. of cells producing IFN-γ/ 2.5 × 10⁵ splenocytes | Stimulate with HIV gp120 4 ug/ml | 121 | 16 | 2 | 5 |
| | Not stimulated | 1 | 1 | 2 | 1 |
| No. of cells producing IL-2/ 2.5 × 10⁵ splenocytes | Stimulate with HIV gp120 4 ug/ml | 166 | 56 | 4 | 5 |
| | Not stimulated | 1 | 3 | 2 | — |
| No. of cells producing IL-4/ 2.5 × 10⁵ splenocytes | Stimulate with HIV gp120 4 ug/ml | 68 | 78 | 5 | 6 |
| | Not stimulated | 11 | 5 | 5 | 3 |

Unit: Splenocyte spot forming cells

TABLE 9

ELISA detection of specific IgG titers from murine serum after immunization with vaccines comprising PIKA and/or inactivated split influenza vaccines

| | Groups of mice | | | | |
|---|---|---|---|---|---|
| | Group 1 Flu 4.5 ug | Group 2 Flu 4.5 ug + PIKA 50 ug | Group 3 Flu 4.5 ug + PIKA 100 ug | Group 4 PIKA 100 ug | Group 5 PBS |
| Optical density absorbance 405 nm at 900× dilution | 1.381 | 1.952 | 2.630 | 0.083 | 0.080 |

The conclusion drawn is that the addition of the PIKA adjuvant enhances the overall immune response to influenza antigen, in particular the specific immune response, more particularly the adaptive immunity and more specifically the cell mediated immune response.

The VAXIGRIP is an approved influenza vaccine recognized to significantly reduce the risk of contracting influenza. The addition of PIKA enhances the level of cytokines produced thereby indicating that a vaccine comprising VAXIGRIP and PIKA also elicits an immune response that significantly reduces the risk of contracting influenza.

Example 1.3

Synthesized HIV Peptide Antigen

The results in table 10 below are the results of the ELISPOT test detecting the presence number of cells producing INF-γ, IL-2 and IL-4 using an HIV peptide antigen. The data in the table 10 (see also FIGS. 9, 10 and 11) represent the ELISPOT reading, the number of spot forming cells, that is, a direct measure of cytokine production.

The distinct increase in the number of spot forming cells with the addition of the PIKA adjuvant (as compared with the The results of the FACS analysis are presented in table 11 below (see also FIG. 12). The presence of CD4+ T cells expressing INF-γ in only the formulations containing both PIKA and HIV antigen confirms the observation that the adaptive immune response has reach a stage of maturity and that PIKA was instrumental in this process.

TABLE 11

FACS analysis of murine splenocytes after immunization with vaccines comprising PIKA and/or HIV gp 120 antigen

| | Groups of mice | | | |
|---|---|---|---|---|
| | Group 1 HIVgp 120 3 ug + PIKA 100 ug | Group 2 HIVgp 120 3 ug | Group 3 PIKA 100 ug | Group 4 NS |
| % of CD4+ve cells producing interferon-γ | 0.194% | 0.017% | 0.012% | 0.014% |

The conclusion drawn is that the addition of the PIKA adjuvant with HIV antigen enhances the overall immune response, in particular the specific immune response, more particularly the adaptive immunity and more specifically the cell mediated immune response.

Example 1.4

Recombinant Anthrax Protective Antigen (rPA) from *Bacillus Anthracis*

The results in table 12 below are the results of the ELISPOT test detecting the presence of INF-γ, IL-2 and IL-4 using a recombinant anthrax. The data in the table 12 (see also FIGS. 13, 14 and 15) represent the ELISPOT reading, the number of spot forming cells, that is, a direct measure of cytokine production.

The distinct increase in the number of spot forming cells with the addition of the PIKA adjuvant (as compared with the antigen alone) demonstrates that the addition of the PIKA adjuvant to the anthrax antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 12

ELISPOT detection of murine splenocytes producing cytokines after immunization with vaccines comprising PIKA and/or anthrax rPA antigen

|  |  | Groups of mice | | | |
|---|---|---|---|---|---|
|  |  | Group 1 Anthrax rPA 3 ug + PIKA 100 ug | Group 2 Anthrax rPA 3 ug | Group 3 PIKA 100 ug | Group 4 NS |
| No. of cells producing IFN-γ/ 2.5 × 10⁵ splenocytes | Stimulation with anthrax rPA 4 ug/ml | 283 | 9 | 2 | 5 |
|  | Not stimulated | 135 | 3 | 2 | 1 |
| No. of cells producing IL-2/ 2.5 × 10⁵ splenocytes | Stimulation with anthrax rPA 4 ug/ml | 134 | 12 | 3 | 4 |
|  | Not stimulated | 47 | 2 | 2 | — |
| No. of cells producing IL-4/ 2.5 × 10⁵ splenocytes | Stimulation with anthrax rPA 4 ug/ml | 61 | 10 | 6 | 3 |
|  | Not stimulated | 9 | 4 | 5 | 3 |

Unit: Splenocyte spot forming cells

The results of the FACS analysis are presented in table 13 below (see also FIG. 16). The presence of CD4+ T cells expressing INF-γ in only the formulations containing both PIKA and rPA antigen confirms the observation that the adaptive immune response has reach a stage of maturity and that PIKA was instrumental in this process.

TABLE 13

FACS analysis of murine splenocytes after immunization with vaccines comprising PIKA and/or anthrax rPA antigen

|  | Groups of mice | | | |
|---|---|---|---|---|
|  | Group 1 Anthrax rPA 3 ug + PIKA 100 ug | Group 2 Anthrax rPA 3 ug | Group 3 PIKA 100 ug | Group 4 PBS |
| % of CD4+ve cells producing Interferon-γ | 0.746% | 0.003% | 0.010% | 0.004% |

Results of the ELISA test on the blood sample taken prior to sacrifice (Table 14 below and FIGS. 16 and 17) demonstrate that the presence of PIKA significantly enhances the immune response and measured by the titer of specific antibodies detected in the serum.

A consistent result was observed 16 weeks after the initial vaccination when blood samples from mice of the original groups A and B were evaluated for the presence of specific antibodies using a standard ELISA test. Again the presence of PIKA with the anthrax antigen induced a significantly higher immune response as measured by the specific antibody titer in the serum.

TABLE 14

ELISA detection of specific IgG titers from murine serum after immunization with vaccines comprising PIKA and/or anthrax rPA antigen

|  |  | Groups of mice | | | |
|---|---|---|---|---|---|
|  |  | Group 1 Anthrax rPA 3 ug + PIKA 100 ug | Group 2 Anthrax rPA 3 ug | Group 3 PIKA 100 ug | Group 4 PBS |
| Optical density absorbance 405 nm at 400× dilution | 4 weeks after immunization | 1.29 | 0.12 | 0.1 | 0.1 |

TABLE 14-continued

ELISA detection of specific IgG titers from murine serum after immunization with vaccines comprising PIKA and/or anthrax rPA antigen

|  |  | Groups of mice | | | |
|---|---|---|---|---|---|
|  |  | Group 1 Anthrax rPA 3 ug + PIKA 100 ug | Group 2 Anthrax rPA 3 ug | Group 3 PIKA 100 ug | Group 4 PBS |
| Optical density absorbance 405 nm at 300× dilution | 16 weeks after immunization | 1.03 |  |  | 0.09 |

The conclusion drawn is that the addition of the PIKA adjuvant enhances the overall immune response to rPA, in particular the specific immune response, more particularly the adaptive immunity and more specifically the cell mediated immune response.

Example 1.5

Recombinant Herpes Simplex Virus 2 gD Antigen

The results in table 15 below are the results of the ELISPOT test detecting the presence of INF-γ, IL-2 and IL-4 using a recombinant herpes simplex virus antigen. The data in the table 15 (see also FIGS. 19, 20 and 21) represent the ELISPOT reading, the number of spot forming cells, that is, a direct measure of cytokine production.

The distinct increase in the number of spot forming cells with the addition of the PIKA adjuvant (as compared with the antigen alone) demonstrates that the addition of the PIKA adjuvant to the herpes simplex virus antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 15

ELISPOT detection of murine splenocytes producing cytokines after immunization with vaccines comprising PIKA and/or HSV 2gD antigen

| | | Groups of mice | | | |
|---|---|---|---|---|---|
| | | Group 1 HSV2gD 3 ug + PIKA 100 ug | Group 2 HSV2gp 3 ug | Group 3 PIKA 100 ug | Group 4 PBS |
| No. of cells producing IFN-γ/ 2.5 × 10⁵ splenocytes | Stimulation with HSV2gD 2.5 ug/ml | 266 | 135 | 2 | 12 |
| | Not stimulated | 2 | 2 | — | 1 |
| No. of cells producing IL-2/ 2.5 × 10⁵ splenocytes | Stimulation with HSV2gD 2.5 ug/ml | 153 | 57 | 4 | 4 |
| | Not stimulated | 2 | 2 | — | — |
| No. of cells producing IL-4/ 2.5 × 10⁵ splenocytes | Stimulation with HSV2gD 2.5 ug/ml | 40 | 25 | 10 | 12 |
| | Not stimulated | 17 | 13 | 11 | 17 |

Unit: Splenocyte spot forming cells

The results of the FACS analysis are presented in table 16 below (see also FIG. 22). The presence of CD4+ T cells expressing INF-γ in only the formulations containing both PIKA and HSV antigen confirms the observation that the adaptive immune response has reach a stage of maturity and that PIKA was instrumental in this process.

TABLE 16

FACS analysis of murine splenocytes after immunization with vaccines comprising PIKA and/or HSV 2gD antigen

| | Groups of mice | | | |
|---|---|---|---|---|
| | Group 1 HSV2gp 3 ug + PIKA 100 ug | Group 2 HSV2gp 3 ug | Group 3 PIKA 100 ug | Group 4 NS |
| % of CD4+ve cells producing interferon-γ | 0.436% | 0.056% | 0.009% | 0.012% |

Results of the ELISA test on the blood sample taken prior to sacrifice (Table 17 below and FIG. 23) demonstrate that the presence of PIKA significantly enhances the immune response and measured by the titer of specific antibodies detected in the serum.

TABLE 17

ELISA detection of specific IgG titers from murine after immunization with PIKA and/or HSV2 gD vaccines

| | Groups of mice | | | |
|---|---|---|---|---|
| | Group 1 HSV2gD 3 ug + PIKA 100 ug | Group 2 HSV2gp 3 ug | Group 3 PIKA 100 ug | Group 4 PBS |
| Optical density absorbance 405 nm at 2,700× dilution | 2.116 | 0.554 | 0.085 | 0.087 |

The conclusion drawn is that the addition of the PIKA adjuvant enhances the overall immune response to HSV antigen, in particular the specific immune response, more particularly the adaptive immunity and more specifically the cell mediated immune response.

Example 1.6

Inactivated H5N1 Whole Virus (Avian Influenza) Antigen

The results in table 18 below are the results of the ELISPOT test detecting the presence of INF-γ, IL-2 and IL-4 using an inactivated non purified H5N1 antigen. The data in table 18 (see also FIGS. 24, 25 and 26) represent the ELISPOT reading, the number of spot forming cells, that is, a direct measure of cytokine production.

The distinct increase in the number of spot forming cells with the addition of the PIKA adjuvant (as compared with the antigen alone) demonstrates that the addition of the PIKA adjuvant to the H5N1 antigen enhances the expression of cytokines INF-γ, IL-2 and IL-4 by cultured spleen cells. The observed expression of cytokines indicates an enhanced adaptive immune response of both a humoral and cell mediated immunity induced by the presence of the PIKA adjuvant.

TABLE 18

ELISPOT detection of murine splenocytes producing cytokines after immunization with vaccines comprising PIKA and/or inactivated H5N1 antigen

|  |  | Groups of mice | | | |
| --- | --- | --- | --- | --- | --- |
|  |  | Group 1 H5N1 4 ul + PIKA 100 ug | Group 2 H5N1 4 ul | Group 3 PIKA 100 ug | Group 4 PBS |
| No. of cells producing interferon-γ/ 2.5 × $10^5$ splenocytes | Stimulated with H5N1 | 394 | 372 | 23 | 98 |
|  | Not stimulated | 3 | 1 | — | 1 |
| No. of cells producing IL-2/ 2.5 × $10^5$ splenocytes | Stimulated with H5N1 | 135 | 97 | 1 | 2 |
|  | Not stimulated | 2 | 2 | — | — |
| No. of cells producing IL-4/ 2.5 × $10^5$ splenocytes | Stimulated with H5N1 | 184 | 137 | 10 | 9 |
|  | Not stimulated | 9 | 11 | 11 | 17 |

Unit: Splenocyte spot forming cells

The results of the FACS analysis are presented in table 19 below (see also FIG. 27). The presence of CD4+ T cells expressing INF-γ in only the formulations containing both PIKA and H5N1 antigen confirms the observation that the adaptive immune response has reach a stage of maturity and that PIKA was instrumental in this process.

TABLE 19

FACS analysis of murine splenocytes after immunization with vaccines comprising PIKA and/or inactivated H5N1 antigen

|  | Groups of mice | | | |
| --- | --- | --- | --- | --- |
|  | Group 1 H5N1 4 ul + PIKA 100 ug | Group 2 H5N1 4 ul | Group 3 PIKA 100 ug | Group 4 NS |
| % CD4+ve cells producing interferon-γ | 1.147% | 0.263% | 0.005% | 0.011% |

Results of the ELISA test on the blood sample taken prior to sacrifice (Table 20 below and FIG. 28) demonstrate that the presence of PIMA significantly enhances the immune response and measured by the titer of specific antibodies detected in the serum.

TABLE 20

ELISA detection of specific IgG titers from murine serum after immunization with vaccines comprising PIKA and/or inactivated H5N1 antigen

|  | Groups of mice | | | |
| --- | --- | --- | --- | --- |
|  | Group 1 H5N1 4 ul + PIKA 100 ug | Group 2 H5N1 4 ul | Group 3 PIKA 100 ug | Group 4 PBS |
| Optical density absorbance 405 nm at 900× dilution | 1.033 | 0.656 | 0.09 | 0.079 |

The conclusion drawn is that the addition of the PIKA adjuvant enhances the overall immune response to H5N1 antigen, in particular the specific immune response, more particularly the adaptive immunity and more specifically the cell mediated immune response.

Example 2

Inactivated Whole Virus SARS Antigen

The objective of this experiment is to demonstrate that the addition of PIKA to a SARS antigen enhances the immune response and stimulates the host's immune system to produce protective SARS specific antibodies.

In this program of research six groups each comprising 4 Balb/c mice were inoculated (peritoneal injection) with a combination of SARS antigen, the antigen plus PIKA (a heterogeneous composition of PIKA molecules predominantly within a weight range of 66 kDa to 1,200,000 kDa), PIKA alone or a control, see table 21 below (see also FIG. 29).

Each group was administered an identical doses on day 0, day 14 and day 28. On week six a blood sample was extracted and the serum tested for the presence of IgG, being a measure of the presence of disease specific antibodies. The blood serum was diluted by a factor of 16,000 times then the presence of IgG was measured using an ELISA reader the procedure being familiar to those skilled in the art. The output being an optical density (O.D.) reading where the greater the value the greater the presence of IgG.

The average result for each group, presented in table 21, demonstrates a correlation between the presence of the PIKA adjuvant and an increase in the expression of IgG.

TABLE 21

ELISA detection of specific IgG titers from murine serum after immunization with vaccines comprising PIKA and/or whole inactivated SARS antigen

| | Groups of mice | | | | |
| --- | --- | --- | --- | --- | --- |
| | Group 1<br>SARS 10 ug | Group 2<br>SARS 10 ug +<br>PIKA 50 ug | Group 3<br>SARS 10 ug +<br>PIKA 250 ug | Group 4<br>PIKA 100 ug | Group 5<br>PBS |
| Optical density absorbtion 405 nm 16,000× dilution | 0.26 | 0.41 | 0.68 | 0.09 | 0.09 |

The conclusion is that the presence of PIKA with the SARS antigen increases the expression of IgG in a dose dependent manner thereby enhancing the immune response of the host.

Example 3

PIKA Vaccine Provides Immune Protection Against H5N1 Infection

The objective of this experiment is to demonstrate that an avian influenza vaccine comprising the PIKA adjuvant is able to protect chickens against live avian flu virus infection.

The research was conducted on two groups of 24 SPF chickens each. At ten days old the birds were inoculated subcutaneously in the neck with a 700 ul dose of vaccine comprising PIKA (a heterogeneous composition of PIKA molecules predominantly within a weight range of 66 kDa to 660 kDa) and two strains of avian influenza (H5N1 and H9N2). The composition included antigen and PIKA adjuvant at a ratio of approximately 2:1 antigen to the PIKA adjuvant.

Blood samples were taken from under the wing at 7, 14 and 21 days. The blood serum from each chicken was tested for the presence of specific H5 and H9 antibodies.

At 21 days the birds were challenged with the H5N1 live virus and then observed for an additional 14 days. The survival rate of the chickens after the 14 days exposure to the live H5N1 virus was recorded.

The average result for each group (Table 22 see also FIGS. 30 and 31) demonstrates that the presence of PIKA induces the production of specific antigen antibodies.

TABLE 22

ELISA detection of specific antibody titers from chicken serum after immunization with vaccines comprising PIKA and/or inactivated H5N1 antigen

| Antibody | Day 0 | Day 7 | Day 14 | Day 21 |
| --- | --- | --- | --- | --- |
| H5 | 0 | 1.2 | 1.44 | 2.4 |
| H9 | 0 | 1.7 | 2.3 | 3.9 |

Units: Optical density reading from ELISA analysis

Of the 24 chickens that were vaccinated with the antigen/PIKA composition 21 (83%) survived for 14 days after exposure to the live H5N1 virus. In the control group of 24 chickens that received no vaccine but were also exposed to the live H5N1 virus only 4 (17%) were alive after 14 days.

The conclusion drawn is that the PIKA vaccine confers a significant level of immune protection against the H5N1 virus.

Example 4

PIKA Vaccine Provides Immune Protection Against Rabies Infection

The objective of this research is to demonstrate that a rabies vaccine comprising the PIKA adjuvant is able to confer protection against a rabies infection.

Four groups (designated i, ii, iii and iv) of 20 Balb/c SPF Kunming mice were each challenged with 100 ul of wild rabies virus strain CQ92. Each group receive inoculations of different types of vaccine; i) a composition of PIKA (a heterogeneous composition of PIKA molecules predominantly within a weight range of 66 kDa to 660 kDa) and inactivated purified hamster kidney cell rabies antigen in a ratio of 1:4 by volume, ii) Sanofi-Aventis' Veroab vero cell inactivated rabies, vaccine iii) the inactivated purified hamster kidney cell rabies vaccine with an alum adjuvant and iv) control phosphate buffer solution. A 60 ul dose of vaccine was administered 30 to 40 minutes, 3 days, 6 days and 9 days after infection by subcutaneous injection into the thigh.

The survival rate of each groups presented in table 23. (see also FIG. 32).

TABLE 23

Survival rates of mice exposed to wild rabies virus and subsequent treatment with rabies vaccines

| | | Survival | |
| --- | --- | --- | --- |
| Vaccine | Mice | Number | % |
| IPHK plus PIKA | 20 | 16 | 80% |
| Verorab | 20 | 4 | 20% |
| IPHK plus alum | 20 | 3 | 15% |
| Control (PBS) | 20 | 2 | 10% |

The conclusion drawn is that the presence of PIKA significantly enhances the immune protection provided by the inactivated purified hamster kidney cell rabies antigen.

Example 5

PIKA Hepatitis B Vaccine Induces the Production of Specific Antibodies in Serum The protocol for the experiment involved the vaccination by subcutaneous injection of three groups of Balb/c mice (three mice per group) with compositions, of, group A, 4 ug of the hepatitis B surface antigen adw alone, group B, 4 ug of the antigen with 75 ug of the PIKA adjuvant (a heterogeneous composition of PIKA molecules predominantly within a weight range distribution of about 66 kDa to 1,200 kDa) and group C, 100 ug of PIKA alone.

The mice were then given an identical booster vaccine by subcutaneous injection ten to fourteen days after the initial injection. Ten to fourteen days after the booster injection a blood sample was taken and tested for the specific antibody titer using a standard ELISA test known to those skilled in the art.

The average results for each group presented in table 24 below (and FIG. 33) demonstrate that the presence of PIKA enhances the immune response to the hepatitis B antigen as measured by the titer of specific antibodies observed in the serum sample.

TABLE 24

ELISA detection of specific antibody titers from murine serum after immunization with vaccines comprising PIKA and/or HBsAg adw

| | Groups of mice | | | | | | |
|---|---|---|---|---|---|---|---|
| | Group 1<br>HBsAg 3 ug | Group 2<br>HBsAg 1 ug +<br>PIKA 80 ug | Group 3<br>HBsAg 2 ug +<br>PIKA 80 ug | Group 4<br>HBsAg 3 ug +<br>PIKA 80 ug | Group 5<br>HBsAg 6 ug +<br>PIKA 80 ug | Group 6<br>PIKA 80 ug | Group 7<br>PBS |
| Optical density absorbtion 405 nm at 12,800× dilution | 0.4160 | 1.9043 | 2.5040 | 2.8470 | 3.0240 | 0.0680 | 0.0747 |

The conclusion drawn from this example is that an immunogenic substance comprising PIKA and a hepatitis B antigen induces the production of a significant immune response as measured by the titer of specific antibodies in the blood serum.

Example 6

PIKA Influenza Vaccine Induces the Production of Specific Antibodies in Serum

The protocol for the experiment involved the vaccination by subcutaneous injection of two groups of Balb/c mice (three mice per group) with compositions of, group A, 4 ug of the Sanofi VAXIGRIP influenza vaccine alone, and group B, 4 ug of the antigen with 100 ug of the PIKA adjuvant (a heterogeneous composition of PIKA molecules predominantly within a weight range distribution of about 66 kDa to 1,200 kDa).

The mice were then given an identical booster vaccine by subcutaneous injection twenty days after the initial injection. Day 35 after the initial vaccination a blood sample was taken and tested for the specific antibody titer using a standard ELISA test known to those skilled in the art.

The average results for each group presented in table 25 below (and FIG. 34) demonstrate that the presence of PIKA enhances the immune response to the influenza vaccine antigens as measured by the titer of specific antibodies observed in the serum sample.

TABLE 25

ELISA detection of specific antibody titers from murine serum after immunization with vaccines comprising PIKA and/or inactivated split influenza antigen

| | Groups of mice | | |
|---|---|---|---|
| | Group 1<br>Flu 4 ug | Group 2<br>Flu 4 ug +<br>PIKA 100 ug | Group 3<br>PIKA 100 ug |
| Optical density absorbtion 405 nm at 10× dilution | 1.839 | 2.804 | 0.087 |

The conclusion drawn from this example is that an immunogenic substance comprising PIKA and an influenza antigen induces the production of a significant immune response as measured by the titer of specific antibodies in the blood serum.

Example 7

PIKA Hepatitis B (Surface Antigen Type adw) Vaccine Induces a Therapeutic Immune Response The protocol for the experiment involves the inoculation of groups of 4 Balb/c mice 6 to 10 weeks old with compositions of a commercially available HBsAg type adw with and without the PIKA adjuvant (a heterogeneous composition of PIKA molecules predominantly within a weight range distribution of about 66 kDa to 1,200 kDa), PIKA alone, a control comprising phosphate buffer solution (PBS).

The mice were administered a prime subcutaneous injection in both sides of the back 100 ul each side. Actual dosage quantities are provided in the tables of results below. The mice were then given an identical booster vaccine twenty one days after the initial injection. On day forty two a blood sample was taken, the mice were then sacrificed and tissue samples taken from the spleen for testing.

ELISPOT assays were conducted to enumerate the antigen-specific interferon-γ secreting T cells. A sample of splenocytes from each mouse was stimulated ex-vivo with either a CD8 T cell peptide epitope from HBsAg (IPQSLDSWWTSL) at a concentration of 5 ug/ml to measure the presence of IPQSLDSWWTSL-specific CD8+ cells.

A second sample of splenocytes were restimulated ex-vivo for six days with 2 ug/ml with the HBsAg peptide IPQSLDSWWTSL. A ELISPOT assay, using 5 ug/ml HBsAg peptide IPQSLDSWWTSL as an ex-vivo stimulant was conducted to detect interferon-γ. This assay was conducted to identify to evaluate the central memory cell response following immunization.

An ELISA assay was used to measure the presence of HBV antigen specific antibodies in the serum, specifically IgG1 and IgG2a antibodies. Nunc Immunoplate Maxisorp plates were coated overnight at 4 deg C. with HBsAg (6 ug/ml in PBS/0.01% Tween 20). The plates were washed with PBS/Tween and blocked for 2 hours with 5% FCS in PBS. After washing serum dilutions in PBS/Tween were added for 2 hours. After washing the either biotin conjugated rat anti-mouse IgG1 monoclonal antibody 1/3000 dilution or the biotin conjugated rat anti-mouse IgG2a monoclonal antibody 1/1500 dilution was added. After washing, streptavidin HRP was added (1/10,000 dilution in PBS/Tween) for 1 hour. After washing ABTS substrate was added with hydrogen peroxide (1000:1) for 20 minutes. The optical density (OD) was then measured at 405 nm the results presented are the average for each group.

The IgG1 response for mice immunized with HBsAg formulated with the PIKA adjuvant were approximately 5 fold higher than the response for mice immunized with HBsAg alone. The titer of IgG1 increased in a dose dependent manner (Table 26 FIG. 35).

TABLE 26

ELISA detection of specific IgG1 titers from murine serum after immunization with vaccines comprising PIKA and/or HBsAg

| HBsAg | PIKA | Group 1 50× | Group 2 150× | Group 3 450× | Group 4 1,350× | Group 5 4,050× | Group 6 12,150× | Group 7 36,450× | Group 8 109,350× |
|---|---|---|---|---|---|---|---|---|---|
| 3 ug | 50 ug | 3.285 | 3.279 | 3.324 | 3.307 | 3.307 | 3.083 | 2.434 | 1.383 |
| 3 ug | 100 ug | 3.387 | 3.416 | 3.448 | 3.486 | 3.559 | 3.368 | 2.924 | 1.917 |
| 3 ug | 200 ug | 3.358 | 3.365 | 3.424 | 3.474 | 3.563 | 3.351 | 3.008 | 2.170 |
| 3 ug | — | 3.065 | 3.065 | 3.135 | 2.966 | 2.814 | 2.362 | 1.546 | 0.790 |
| — | 100 ug | 0.493 | 0.248 | 0.157 | 0.113 | 0.109 | 0.120 | 0.102 | 0.101 |
| PBS 100 ul | | 0.136 | 0.101 | 0.086 | 0.075 | 0.080 | 0.077 | 0.082 | 0.087 |

Unit: Average optical density value

The IgG2a response for mice immunized with HBsAg formulated with the PIKA adjuvant were significantly greater than the response for mice immunized with HBsAg alone. The titer of IgG2a increased in a dose dependent manner, indicative of an increased Th1 biased immune response (Table 27 FIG. 36).

TABLE 27

ELISA detection of specific IgG1 titers from murine serum after immunization with vaccines comprising PIKA and/or HBsAg

| HBsAg | PIKA | Group 1 50× | Group 2 150× | Group 3 450× | Group 4 1,350× | Group 5 4,050× | Group 6 12,150× | Group 7 36,450× | Group 8 109,350× |
|---|---|---|---|---|---|---|---|---|---|
| 3 ug | 50 ug | 3.159 | 2.950 | 2.860 | 2.061 | 1.234 | 0.582 | 0.265 | 0.135 |
| 3 ug | 100 ug | 3.411 | 3.170 | 3.137 | 2.101 | 1.127 | 0.488 | 0.221 | 0.122 |
| 3 ug | 200 ug | 3.397 | 3.346 | 3.560 | 2.636 | 1.955 | 1.005 | 0.455 | 0.203 |
| 3 ug | — | 0.122 | 0.098 | 0.087 | 0.072 | 0.069 | 0.065 | 0.069 | 0.064 |
| — | 100 ug | 0.108 | 0.086 | 0.078 | 0.070 | 0.067 | 0.068 | 0.067 | 0.065 |
| PBS 100 ul | | 0.088 | 0.078 | 0.074 | 0.067 | 0.066 | 0.066 | 0.066 | 0.067 |

Unit: Average optical density value

The ELISPOT assay of the CD8 peptide epitope specific ex-vivo stimulation showed an undetectable response for the mice immunized with HBsAg alone. By contrast, cells expressing interferon-γ were readily detectable after immunization with HBsAg formulated with PIKA in a dose dependent manner indicating that PIKA enhances a therapeutic immune response (Table 28 FIG. 37).

TABLE 28

ELISPOT detection of murine splenocytes producing interferon-γ after immunization with vaccines comprising PIKA and/or HBsAg

| | | Group 1 | Group 2 | Group 3 | Group 4 | Group 5 |
|---|---|---|---|---|---|---|
| | | | | HBsAg | | |
| | | 3 ug | 3 ug | 3 ug | ug | — |
| | | | | PIKA | | |
| | | — | 50 ug | 100 ug | 200 ug | 100 ug |
| Stimulation with IPQ peptide 5 ug/ml | No long term stimulation | 209 | 229 | 490 | 535 | 21 |
| Stimulation with IPQ peptide 5 ug/ml | Restimulate for 6 days with 2 ug/ml IPQ peptide | 2 | 82 | 89 | 48 | 3 |

Unit: Splenocyte spot forming cells

Further the ELISPOT assay conducted after the cultivation of the splenocytes for six days demonstrated that the number of splenocytes producing interferon-γ from the mice vaccinated with formulations comprising HBsAg and the PIKA adjuvant were twice the number of splenocytes from mice administered the HBsAg alone. The results confirm that the presence of PIKA enhances the activation of central memory cells (Table 28 FIG. 38).

The invention claimed is:

1. An immunogenic composition suitable for human use, the immunogenic composition comprising:
    (a) a polynucleotide adjuvant composition comprising complexes of a polyriboinosinic-polyribocytidylic acid (PIC), kanamycin, and calcium, wherein the polynucleotide adjuvant composition comprises said complexes having sedimentation coefficients greater than 9.0 Svedbergs; and
    (b) at least one antigen.

2. The immunogenic composition according to claim 1, wherein the polynucleotide adjuvant composition comprises said complexes having sedimentation coefficients greater than 12.0 Svedbergs.

3. The immunogenic composition according to claim 1, wherein the antigen is an inactivated microorganism, attenuated microorganism, recombinant polypeptide, synthetic polypeptide, attenuated toxin, protein subunit, polysaccharide conjugate, tumor antigen, or recombinant DNA.

4. The immunogenic composition according to claim 1, wherein the antigen is a viral antigen.

5. The immunogenic composition according to claim 4, wherein the viral antigen is an antigen of adeniviridae, arenaviridae, astroviridae, bunyaviridae, caliciviridae, coronaviridae, flaviviridae, hepadnaviridae, hepatitis delta virus, hepeviridae, herpesviridae, mononegavirales, nidovirales, picornaviridae, orthomyxoviridae, papillomaviridae, paramyxoviridae, parvoviridae, polyomaviridae, poxviridae, rhabdoviridae, reoviridae, retroviridae or togaviridae.

6. The immunogenic composition according to claim 1, wherein the antigen is a bacterial antigen.

7. The immunogenic composition according to claim 6, wherein the bacterial antigen is an antigen of actinobacteria, chlamydiae, firmicutes, proteobacteria, or spirochaetes.

8. The immunogenic composition according to claim 1, wherein the antigen is a fungal antigen.

9. The immunogenic composition according to claim 8, wherein the fungal antigen is an antigen of ascomycota or basidiomycota.

10. The immunogenic composition according to claim 1, wherein the antigen is a parasitic antigen.

11. The immunogenic composition according to claim 10, wherein the parasitic antigen is an antigen of phylum sarcomastigophora, phuylum apiicomplexa, phylum ciliophora, phylum plathyhelminthes, phylum nematoda or phylum arthropoda.

12. The immunogenic composition according to claim 1, wherein the antigen is a cancer antigen.

13. The immunogenic composition according to claim 12, wherein the cancer antigen is an antigen of bone, brain, breast, digestive/gastrointestinal, endocrine, eye, genitourinary, germ cell, gynecologic, head and neck, hematological/blood, lung, musculoskeletal, neurologic, respiratory/thoracic or skin cancer.

14. The immunogenic composition according to claim 1, wherein the composition comprises two or more antigens.

15. The immunogenic composition according to claim 1, further comprising at least one immunomodulator.

16. A kit comprising the immunogenic composition of claim 1.

17. A method for eliciting an immune response to an antigen in a host, the method comprising:
    administering to the host the immunogenic composition of claim 1.

18. The method according to claim 17, wherein the host has an infectious disease and said antigen is from the pathogen causing the infectious disease.

19. The method according to claim 17, wherein said administering comprises parenteral injection, intramuscular injection, intraperitoneal injection, intravenous injection, subcutaneous injection, intranasal delivery, topical delivery, transdermal delivery or intradermal delivery.

* * * * *